US010336811B2

(12) United States Patent
Tavernier et al.

(10) Patent No.: US 10,336,811 B2
(45) Date of Patent: *Jul. 2, 2019

(54) MEMBRANE SPAN-KINASE FUSION PROTEIN AND THE USES THEREOF

(71) Applicants: VIB VZW, Ghent (BE); Universiteit Gent, Ghent (BE)

(72) Inventors: Jan Tavernier, Balegem (BE); Samuel Lievens, Aalter (BE)

(73) Assignees: VIB VZW, Ghent (BE); Universiteit Gent, Ghent (BE)

(*) Notice: Subject to any disclaimer, the term of this patent is extended or adjusted under 35 U.S.C. 154(b) by 140 days.

This patent is subject to a terminal disclaimer.

(21) Appl. No.: 14/381,502

(22) PCT Filed: Mar. 6, 2013

(86) PCT No.: PCT/EP2013/054507
§ 371 (c)(1),
(2) Date: Aug. 27, 2014

(87) PCT Pub. No.: WO2013/131957
PCT Pub. Date: Sep. 12, 2013

(65) Prior Publication Data
US 2015/0011417 A1 Jan. 8, 2015

(30) Foreign Application Priority Data
Mar. 6, 2012 (EP) .................................. 12158276

(51) Int. Cl.
*C12N 9/02* (2006.01)
*C07K 14/72* (2006.01)
*C12N 15/62* (2006.01)
*C07K 14/705* (2006.01)
*C12N 9/12* (2006.01)
*C12Q 1/66* (2006.01)
*G01N 33/58* (2006.01)
*G01N 33/74* (2006.01)

(52) U.S. Cl.
CPC .......... *C07K 14/723* (2013.01); *C07K 14/705* (2013.01); *C12N 9/0069* (2013.01); *C12N 9/12* (2013.01); *C12N 15/62* (2013.01); *C12Q 1/66* (2013.01); *C12Y 207/10002* (2013.01); *G01N 33/581* (2013.01); *G01N 33/74* (2013.01); *C07K 2319/42* (2013.01); *C07K 2319/61* (2013.01); *G01N 2333/726* (2013.01); *G01N 2333/90241* (2013.01); *G01N 2333/91205* (2013.01); *G01N 2500/02* (2013.01); *G01N 2500/10* (2013.01)

(58) Field of Classification Search
CPC ............................. G01N 33/581; G01N 33/78
See application file for complete search history.

(56) References Cited

U.S. PATENT DOCUMENTS

| 5,637,463 A | 6/1997 | Dalton et al. |
| 5,658,791 A * | 8/1997 | Wilks .................... C07K 16/40 435/331 |
| 5,776,689 A | 7/1998 | Karin et al. |

FOREIGN PATENT DOCUMENTS

| WO | 9002809 A1 | 3/1990 |
| WO | 9220791 A1 | 11/1992 |
| WO | 9710330 A1 | 3/1997 |
| WO | 9732017 A1 | 9/1997 |
| WO | 9834948 A1 | 8/1998 |
| WO | 0017221 A1 | 3/2000 |
| WO | 0017221 A9 | 6/2000 |
| WO | 0158923 A2 | 8/2001 |
| WO | 0190188 A2 | 11/2001 |
| WO | 0190188 A9 | 9/2002 |
| WO | 2004099419 A2 | 11/2004 |
| WO | 2012117031 A1 | 9/2012 |
| WO | 2013131957 A1 | 9/2013 |

OTHER PUBLICATIONS

Urech et al, Cell growth selection system to detect extracellular and transmembrane protein interactions. Biochimica et Biophysica Acta 1622 (2003) 117-127.*
Eyckerman et al, Design and application of a cytokinereceptor-based interaction trap. Nature Cell Biology vol. 3 Dec. 2001 p. 1114-1119.*
Constantinescu et al, Mining for JAK-STAT mutations in cancer. Trends in Biochemical Sciences 2008 vol. 33 No. 3 p. 122-131.*
Duhe et al, Characterization of the in vitro kinase activity of a partially purified soluble GST/JAK2 fusion protein. Molecular and Cellular Biochemistry 236: 23-35, 2002.*
Hanyaloglu et al, (2002) Homo- and hetero-oligomerization of thyrotropin-releasing hormone (TRH) receptor subtypes. Differential regulation of beta-arrestins 1 and 2. J. Biol. Chem. 277, 50,422-50,430.*
Oh et al, A receptor-independent, cell-based JAK activation assay for screening for JAK3-specific inhibitors. Journal of Immunological Methods 354 (2010) 45-52.*

(Continued)

*Primary Examiner* — Sheridan Swope
(74) *Attorney, Agent, or Firm* — Patent Law Works LLP

(57) ABSTRACT

The disclosure relates to a recombinant membrane span protein complex, comprising (1) a fusion protein, comprising a membrane span protein fused to a kinase domain, preferably a constitutive kinase and (2) a reporter construct comprising a polypeptide, interacting with the membrane span protein, fused to a reporter phosphorylation domain. The disclosure relates further to the uses of such membrane span protein complex for the detection of compounds that interact with the membrane span protein and for the screening and/or detection of inhibitors of the compound-membrane span protein interactions. In a preferred embodiment, the membrane span protein is a G protein coupled receptor (GPCR) and the method is used for the screening and/or detection of inhibitors of the ligand-receptor binding.

10 Claims, 9 Drawing Sheets
Specification includes a Sequence Listing.

(56) References Cited

OTHER PUBLICATIONS

Jin et al, Interaction of the mu-opioid receptor with GPR177 (Wntless) inhibits Wnt secretion: potential implications for opioid dependence. BMC Neurosci. Mar. 9, 2010;11:33. doi: 10.1186/1471-2202-11-33.*

Berchtold et al, Cytokine receptor-independent, constitutively active variants of STAT5. J Biol Chem. Nov. 28, 1997;272(48):30237-43.*

Cheng et al, Arsenic inhibition of the JAK-STAT pathway. Oncogene (2004) 23, 3603-3612.*

Bovijn et al., Identification of Interaction Sties for Dimerization and Adapter Recruitment in Toll/Interleukkn-1 Receptor (TIR) Domain of Toll-like Receptor 4, Journal of Biological Chemistry, Dec. 2, 2011, pp. 4088-4098, vol. 287, No. 6.

Tavernier et al., MAPPIT: a cytokine receptor-based two-hybrid method in mammalian cells, Clin Exp. Allergy, Jan. 1, 2002, pp. 1397-1404.

PCT International Search Report, PCT/EP2013/054507, dated May 17, 2013.

Kiu, Hiu, and Sandra E. Nicholson. "Biology and Significance of the Jak/stat Signalling Pathways." Growth Factors. 30.2 (2012): 88-106.

Lievens, Sam, Sarah Gerlo, Irma Lemmens, Clercq D. J. H. De, Martijn D. P. Risseeuw, Nele Vanderroost, Smet A.-S. De, Elien Ruyssinck, Eric Chevet, Calenbergh S. Van, and Jan Tavernier. "Kinase Substrate Sensor (kiss), a Mammalian<i>in Situ</i>protein Interaction Sensor." Molecular & Cellular Proteomics. 13.12 (2014): 3332-3342.

Nyfeler, B, S W. Michnick, and H.-P Hauri. "Capturing Protein Interactions in the Secretory Pathway of Living Cells." Proceedings of the National Academy of Sciences. 102.18 (2005): 6350-6355.

* cited by examiner

A

B

A

B

MEMBRANE SPAN-KINASE FUSION PROTEIN AND THE USES THEREOF

CROSS-REFERENCE TO RELATED APPLICATIONS

This application is a national phase entry under 35 U.S.C. § 371 of International Patent Application PCT/EP2013/054507, filed Mar. 6, 2013, designating the United States of America and published in English as International Patent Publication WO 2013/131957 A1 on Sep. 12, 2013, which claims the benefit under Article 8 of the Patent Cooperation Treaty to European Application Serial No. 12158276.1, filed Mar. 6, 2012.

TECHNICAL FIELD

The disclosure relates to a recombinant membrane span protein complex, comprising (1) a fusion protein, comprising a membrane span protein fused to a kinase domain, preferably a constitutive kinase and (2) a reporter construct comprising a polypeptide, interacting with the membrane span protein, fused to a reporter phosphorylation domain. The disclosure relates further to the uses of such membrane span protein complex for the detection of compounds that interact with the membrane span protein and for the screening and/or detection of inhibitors of the compound-membrane span protein interactions. In a preferred embodiment, the membrane span protein is a G protein coupled receptor (GPCR) and the method is used for the screening and/or detection of inhibitors of the ligand-receptor binding.

BACKGROUND

Several methods have been developed to detect protein-protein interactions, all with their advantages and limitations. Co-purification of proteins and co-immunoprecipitation were amongst the first techniques used. However, these methods are tedious and do not allow high throughput screening. Moreover, they require lysis corrupting the normal cellular context. A major breakthrough was obtained by the introduction of the genetic approaches, of which the yeast two-hybrid (Fields and Song, 1989) is the most important one. Although this technique became widely used, it has several drawbacks. The fusion proteins need to be translocated to the nucleus, which is not always evident. Proteins with intrinsic transcription activation properties may cause false positives. Moreover, interactions that are dependent upon secondary modifications of the protein such as phosphorylation cannot be easily detected.

Several alternative systems have been developed to solve one or more of these problems.

Approaches based on phage display do avoid the nuclear translocation. WO9002809 describes how a binding protein can be displayed on the surface of a genetic package, such as a filamentous phage, whereby the gene encoding the binding protein is packaged inside the phage. Phages, which bear the binding protein that recognizes the target molecule, are isolated and amplified. Several improvements of the phage display approach have been proposed, as described, e.g., in WO9220791, WO9710330 and WO9732017.

However, all these methods suffer from the difficulties that are inherent at the phage display methodology: the proteins need to be exposed at the phage surface and are so exposed to an environment that is not physiological relevant for the in vivo interaction. Moreover, when screening a phage library, there will be a competition between the phages that results in a selection of the high affinity binders.

U.S. Pat. No. 5,637,463 describes an improvement of the yeast two-hybrid system, whereby can be screened for modification dependent protein-protein interactions. However, this method relies on the co-expression of the modifying enzyme, which will exert its activity in the cytoplasm and may modify other enzymes than the one involved in the protein-protein interaction, which may on its turn affect the viability of the host organism.

An interesting evolution is described in U.S. Pat. No. 5,776,689, by the so-called protein recruitment system. Protein-protein interactions are detected by recruitment of a guanine nucleotide exchange factor (Sos) to the plasma membrane, where Sos activates a Ras reporter molecule. This results in the survival of the cell that otherwise would not survive in the culture conditions used. Although this method has certainly the advantage that the protein-protein interaction takes place under physiological conditions in the submembranary space, it has several drawbacks. Modification-dependent interactions cannot be detected. Moreover, the method is using the pleiotropic Ras pathway, which may cause technical complications. Most of these drawbacks were solved by the Mammalian Protein-Protein Interaction Trap (MAPPIT) described in WO0190188, using recruitment of a prey to a cytokine type of receptor, fused to a bait. However, although this method allows to study protein-protein interactions under physiological conditions, it is not suitable to study interactions involving integral membrane proteins, particularly multispan membrane proteins, including GPCR's.

Methods for studying the interaction of proteins with a GPCR are mainly focused on ligand-receptor binding. WO9834948 discloses a GPCR wherein the amino terminus is replaced by the amino-terminus of a self-activating receptor, and the use of this construct for the detection of agonists and antagonists. WO2004099419 discloses a ligand upregulatable GPCR, and the use of this construct to screen ligands. WO0158923 describes methods for detecting GPCR activity, methods for assaying GPCR activity and methods for screening GPCR ligands, G-protein-coupled receptor kinase activity and compounds that interact with the GPCR regulatory process, by an enzyme complementation assay. However, this system is rather insensitive, with a maximal window of a factor 2 at the highest concentrations of agonist or antagonist used. Moreover, the system needs a mutation in arrestin, to improve arrestin binding, in order to obtain the required sensitivity.

SUMMARY OF THE DISCLOSURE

Surprisingly, we found that by replacing the enzyme complementation by a detection system of a reporter phosphorylation polypeptide by a kinase, preferably a mutant kinase, even more preferably a constitutive mutant kinase, or an inactive mutant kinase that is activated by addition of an exogenous small molecule, the detection window could be increased significantly. Moreover, using a specific signaling pathway starting from the reporter phosphorylation site, several reporter systems can be used.

A first aspect of the disclosure is a recombinant membrane span protein complex, comprising (1) a first fusion protein, comprising a membrane span protein fused to either a kinase domain or a reporter phosphorylation domain, and (2) a second fusion protein comprising a polypeptide, interacting with the membrane span protein, fused to either a reporter phosphorylation domain or a kinase domain, complementary to the first fusion protein. "Complementary to the first fusion protein," as used herein, means that in case the first fusion protein is a fusion to a kinase domain, the second fusion protein is a fusion to a reporter phosphorylation domain and vice versa: if the first fusion protein is a fusion to a reporter phosphorylation domain, the second fusion protein is a fusion to a kinase domain. In the normal two hybrid technology, the membrane span protein acts as a first interaction protein and is indicated as "bait" and the second fusion protein acts as second interaction protein and is indicated as "prey." Preferably, the kinase domain is a mutant kinase domain. In one preferred embodiment, the mutant kinase domain is a constitutive mutant kinase domain. In another preferred embodiment, the mutant kinase domain is an inactive mutant kinase domain that is activated by addition of an exogenous small molecule. Several embodiments of the disclosure are represented in FIG. 1.

In one preferred embodiment, the kinase is a constitutive kinase mutant derived from Tyk2, such as, but not limited to, a constitutive Tyk2 deletion mutant or and/or a Tyk2 V678F mutant. Derived from Tyk2, as used herein, means that the kinase is a part of the human Tyk2 non-receptor tyrosine-protein kinase (Genbank accession number NP_003322; version NP_003322.3; SEQ ID NO:1) or a mutant or variant thereof wherein the part shows constitutive kinase activity. A variant, as a non-limiting example, is a homologue, paralogue or orthologue. "Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived. "Orthologues" and "paralogues" encompass evolutionary concepts used to describe the ancestral relationships of genes. "Paralogues" are genes within the same species that have originated through duplication of an ancestral gene; "orthologues" are genes from different organisms that have originated through speciation, and are also derived from a common ancestral gene. Preferably, the homologue, "orthologue" or "paralogue" has a sequence identity at protein level of at least 50%, 51%, 52%, 53%, 54% or 55%, 56%, 57%, 58%, 59%, preferably 60%, 61%, 62%, 63%, 64%, 65%, 66%, 67%, 68%, 69%, more preferably 70%, 71%, 72%, 73%, 74%, 75%, 76%, 77%, 78%, 79%, even more preferably 80%, 81%, 82%, 83%, 84%, 85%, 86%, 87%, 88%, 89% most preferably 90%, 91%, 92%, 93%, 94%, 95%, 96%, 97%, 98%, 99% or more as measured in a BLASTp (Altschul et al., 1997; Altschul et al., 2005). Variants and parts thereof, according to the disclosure, do show kinase activity. Preferably, the part is a part with constitutive kinase activity, preferably fragment 589-1187 of SEQ ID NO:1. Alternatively, the part is the part, corresponding to fragment 589-1187 of SEQ ID NO:1 in a homologue, paralogue or orthologue as defined above, wherein the part has constitutive kinase activity. In an alternative embodiment the constitutive kinase is a constitutive kinase derived from a Jak kinase, preferably from a Jak kinase selected from the group consisting of Jak 1 (Accession number P23458, version P23458.2), Jak2 (Accession number O60674, version O60674.2) and Jak3 (Accession number P52333, version P52333.2) or a mutant or variant thereof, as defined above. Preferably, the constitutive kinase is a constitutive Jak2 deletion mutant. In still another alternative embodiment, the constitutive kinase is a constitutive kinase derived from a Src kinase (Accession number NP_005408, version NP_005408.1) or a mutant or variant thereof, as defined above. Preferably, the Src derived kinase is a kinase as depicted in SEQ ID NO:8.

In another preferred embodiment, the mutant tyrosine kinase is an inactive mutant that is activated by addition of an exogenous small molecule. Such mutant kinase is known to the person skilled in the art, and has been described, as a non-limiting example, by Qiao et al., (2006) as a Src 388R/A mutant or a 391R/A mutation in the corresponding human Src protein (Accession number NP_938033, version NP_938033.1), or a mutant or variant thereof, as defined above. Alternatively, it may be a similar mutation in the Jak kinase family, such as, but not limited to, Tyk2 1027R/A, or a mutant or variant thereof.

A membrane span protein may be any membrane span protein known to the person skilled in the art. Membranes include, but are not limited to, the cellular membrane, the endoplasmatic reticulum and the mitochondrial membrane. A "membrane span" means that the protein crosses the membrane, while sticking out at both sides of the membrane. The "membrane span protein," as used herein, may contain a single membrane span, or multiple membrane spans. Preferably, the membrane span protein is a multiple membrane span protein, comprising at least two membrane spans, even more preferably, the membrane span protein is a cellular membrane multispan membrane protein, most preferably the membrane span protein is a GPCR. A GPCR chain, as used herein, means any polypeptide chain with 7 transmembrane spans that can function as a G-protein coupled receptor. In a preferred embodiment, it is a known GPCR; however, for the disclosure, the original GPCR may carry mutations, insertions and/or deletions, and/or extension at the amino terminal and/or carboxyterminal end, as long as the capacity of binding with a ligand is not inhibited by the mutations or modifications.

Preferably, the kinase domain is fused at, or in the cytoplasmic part of the membrane span protein. In one preferred embodiment, the kinase domain is fused in a cytoplasmic loop of a multispan membrane span protein, preferably in a cytoplasmic loop of a GPCR chain. In another preferred embodiment, the kinase domain is fused to the carboxyterminal end of the membrane span protein. The fusion may be direct, i.e., by direct coupling of the kinase domain to the carboxyterminal end of the membrane span protein chain, or it may be indirect, using a linker sequence between the membrane span protein chain and the kinase domain. In case of a fusion within the membrane span protein chain, the linker may be situated at one side of the kinase domain, or at both sides. Preferably, the linker is shorter than 20 amino acids, more preferably shorter than 10 amino acids, even more preferably between 5 and 10 amino acids, most preferably 6 amino acids.

A reporter phosphorylation domain can be any domain that comprises a tyrosine, wherein the tyrosine can be phosphorylated by a tyrosine kinase. Preferably, the reporter phosphorylation domain is derived from or comprises a fragment of gp130, even more preferably the reporter phosphorylation domain consists of a fragment of gp130. Most preferably, the reporter phosphorylation domain consists of SEQ ID NO:2

Another aspect of the disclosure is the use of a recombinant membrane span protein complex, according to the disclosure, to detect compound-protein interaction, preferably protein-protein interactions. Detection of the compound-protein or protein-protein interaction may be direct or indirect. Direct detection of an interaction is the detection of the interaction of a fusion protein (fused to a reporter phosphorylation domain or a kinase domain), recruited to the membrane span protein chain (fused to a kinase domain or a reporter phosphorylation domain, complementary to the recruited fusion protein) wherein the membrane span protein or a domain thereof act as first interaction protein. In this case, the interaction of the first and second interaction protein brings the reporter phosphorylation domain close to the kinase domain and the interaction is detected by phosphorylation of the reporter phosphorylation domain. Indirect detection of an interaction is the detection of the phosphorylation of the reporter phosphorylation domain, wherein the reporter phosphorylation domain is brought in contact to the kinase domain by recruitment of a fusion protein to the receptor upon a compound-protein interaction that induces the recruitment of the fusion protein. Such compound-protein interaction may be, as a non-limiting example, the ligand-receptor binding, wherein ligand means every compound that can bind to the extracellular domain of a receptor and that is able to initiate the signaling pathway by binding to the extracellular domain. Initiating, as used herein, means starting the events that normally directly follow the binding of the ligand to the extracellular domain of a receptor, e.g., multimerization for a multimerizing receptor, but it does not imply activation of the receptor and/or accomplishing of the signaling pathway. Compound means any chemical or biological compound, including simple or complex organic or inorganic molecules, peptides, peptido-mimetics, proteins, antibodies, carbohydrates, nucleic acids or derivatives thereof. In a special embodiment, the fusion protein that is recruited to the membrane span protein (fused to a reporter phosphorylation domain or a kinase domain) may be another membrane span protein fused to a kinase domain or a reporter phosphorylation domain, complementary to that of the recruiting fusion protein, allowing the detection of homodimerization, homomultimerization, heterodimerization or heteromultimerization of membrane span proteins.

The detection of the phosphorylation of the reporter phosphorylation domain can be by any method known to the person skilled in the art. In one preferred embodiment, the reporter phosphorylation is inducing a signaling pathway, preferably a STAT3 dependent pathway, resulting in the activation of a reporter gene, such as a luciferase gene. Alternatively, the phosphorylation of the reporter phosphorylation domain may be detected directly, e.g., by phosphorylation dependent binding of an antibody, or by detection of intermediates of the signaling pathway such as STAT3 dimers. Still another alternative reporter system consist of a protein complementation assay, wherein one part of the protein is incorporated in or associated with the cytoplasmic protein complex, according to the disclosure, and the second part of the protein is recruited to the phosphorylated reporter phosphorylation site, leading to a detectable activity of the reconstituted protein. Preferably, the readout of the receptor system has a window of at least a factor 4, preferably at least a factor 5, even more preferably at least a factor 10. The readout window is defined as the ration of the signal to the noise (negative control).

Still another aspect of the disclosure is the use of a recombinant membrane span protein complex, according to the disclosure, to screen inhibitors of a compound-protein interaction, preferably a protein-protein interaction. Indeed, it is clear for the person skilled in the art that, if the compound-protein interaction is giving a detectable signal, inhibitors of the compound-protein interactions can be screened by adding compounds to the test system and screening for those compounds that disturb the detectable signal.

The eukaryotic cell can be any eukaryotic cell capable of expressing a membrane span protein, including but not limited to, yeast cells, fungal cells and mammalian cells. Preferably, the cell is a mammalian cell. In one preferred embodiment, the eukaryotic host cells comprising the recombinant membrane span protein chain fused to a kinase domain (or a reporter phosphorylation domain) are transformed with a library of polypeptides, all fused to the reporter phosphorylation domain (or a kinase domain, if the membrane span protein is fused to a reporter phosphorylation domain). Cells, in which the reporter phosphorylation domain will be phosphorylated are comprising a prey-reporter phosphorylation domain construct that is capable of interacting with the membrane span protein chain. In another preferred embodiment, the eukaryotic host cell comprises a recombinant GPCR chain fused to a kinase domain (or a reporter phosphorylation domain) and the cell is transformed with a polypeptide, capable of interacting with the membrane span protein chain upon activation of the GPCR by ligand binding, wherein the polypeptide is fused to the reporter phosphorylation domain (or a kinase domain, respectively), and the cell is contacted with compounds that may act as ligand. Binding of such compound to the GPCR will induce the recruitment of the polypeptide-phosphorylation domain fusion and result in the phosphorylation of the reporter phosphorylation domain. Polypeptide, as used herein, means any proteinaceous structure, independent of the length and includes molecules such as peptides, phosphorylated proteins and glycosylated proteins. Polypeptide, as used herein, is not necessarily indicating an independent compound but can also be used to indicate a part of a bigger compound, such as a domain of a protein.

Another aspect of the disclosure, is a method to detect compound-protein interactions, the method comprising (1) transforming a eukaryotic host cell with a first fusion protein, comprising a recombinant membrane span protein chain, fused to either a kinase domain or a reporter phosphorylation domain (2) transforming the same host cell with at least one second fusion protein, comprising a polypeptide, fused to either a reporter phosphorylation domain or a kinase domain, complementary to the first fusion protein wherein the polypeptide is capable of interacting with the membrane span protein chain (3) adding the compound to be tested to the cell (4) optionally adding the ligand to the cell and (5) detecting the phosphorylation of the reporter phosphorylation domain. The sequence of the transformation steps may be inverted; a ligand is added in cases where the compound is not tested as a ligand; in this case, the steps of adding compound and ligand may be interchanged.

Still another aspect of the disclosure is a method to screen inhibitors of a compound-protein interaction, the method comprising 1) transforming a eukaryotic host cell with first fusion protein, comprising a recombinant membrane span protein chain, fused to a either kinase domain or a reporter phosphorylation domain (2) transforming the same host cell with at least one second fusion protein, comprising a polypeptide, fused to a either a reporter phosphorylation domain or a kinase domain, complementary to the first fusion protein, wherein the polypeptide is interacting with the membrane span protein chain (3) adding at least one possible inhibitor molecule (4) adding the ligand to the cell and (5) detecting the phosphorylation of the reporter phosphorylation domain. Preferably, the same set up without inhibitor is used as positive control for the protein-protein interaction. The sequence of the transformation steps may be inverted; the steps of adding inhibitor and ligand may be interchanged.

DEFINITIONS

The following definitions are set forth to illustrate and define the meaning and scope of various terms used to describe the disclosure herein.

Protein, as used herein, means a chain composed of amino acids, independent of the length. The terms "protein" and "polypeptide" are interchangeable. The protein can be modified by modifications such as, but not limited to, phosphorylation, glycosylation, ubiquitinilation and acetylation.

Domain, as used herein, is a part of a polypeptide, wherein the part may carry a specific function, such as, but not limited to, an enzymatic center or a phosphorylation site.

Protein complex, as used herein, means a structure that comprises at least two, non-covalently linked, protein molecules. Protein complexes can consist of more than two proteins, and include other molecules that are not proteins. Some non-limiting examples of such molecules are metal ions, ATP, or carbohydrate molecules.

A kinase, as used herein, is a polypeptide that can transfer a phosphate group to an amino acid of the same or another polypeptide. Preferably, the amino acid is a serine, a threonine or a tyrosine. Even more preferably, the amino acid is embedded in a phosphorylation site. A phosphorylation site, as used herein, is a pattern of several amino acids, preferably comprising a serine, threonine or a tyrosine, and determining the amino acid that will be phosphorylated by the kinase. Most kinases can occur in an inactive and in an active state, wherein the reporter phosphorylation site is only phosphorylated in the active state of the kinase. Kinases can be switched from the inactive from to the active form by phosphorylation, or by other modifications such as proteolysis, or by mutation. The phosphorylation can be autophosphorylation, crossphosphorylation (by a protein complex of identical kinases) or by action of another kinase.

Constitutive, as used herein, means that the kinase is continuously in the active state, normally as a consequence of a mutation, or by proteolytic cleavage removing an inhibitor. Constitutive kinases are known to the person skilled in the art and comprise, but are not limited to, truncated forms of Tyk2, truncated forms of Src kinase and point mutations such as Tyk2 (V678F), Jak1 (V658F) and Jak2 (V617F).

An inactive kinase mutant means that the mutant form shows a kinase activity that is significantly lower than the original non-mutated form. Preferably, the remaining activity is lower than 50% of the original activity, even more preferably lower than 20%, more preferably lower than 10%, most preferably lower than 5% of the original activity.

Activated by the addition an exogenous small compound, as used herein, means that the activity of the inactive kinase is partly or totally restored by addition of a small compound to the cells, whereby the small compound, exogenous to the cell, is taken up by the cell and activates the kinase as an intracellular exogenous compound. "Activated by the addition an exogenous small compound" is used to make a distinction with ligand-receptor induced activation, where a ligand is binding to the extracellular part of a receptor, and induces activation of the kinase. "Exogenous," as used herein, means that the compound is normally not present in the cell.

Reporter phosphorylation site is the site that is phosphorylated in the protein complex upon interaction of the first and the second interaction polypeptide; it is distinct from a possible phosphorylation site in the kinase domain that is autophosphorylated in the constitutive kinase.

First interaction polypeptide, as used herein, is a polypeptide of which one wants to study the interaction with one or more compounds. The first interaction polypeptide is normally referred to as a "bait" in the two hybrid terminology.

Second interaction polypeptide, as used herein, is a polypeptide that is presented to study its interaction with the first interaction polypeptide. The second interaction polypeptide is normally referred to as a "prey" in the two hybrid terminology. It is clear for the person skilled in the art that the first and the second interaction polypeptide are interchangeable in the disclosure, in this respect that either a "bait" or a "prey" may be fused to constitutive kinase, according to the disclosure. Indeed, the resulting protein complex will have an identical overall composition, composed of the four essential elements (first interaction polypeptide, second interaction polypeptide, constitutive kinase and reporter phosphorylation site), and independent whether the first interaction polypeptide is fused to the constitutive kinase or the reporter phosphorylation site (wherein the second interaction polypeptide is then fused to the reporter phosphorylation site, and the constitutive kinase, respectively), the interaction of the first with the second interacting polypeptide will lead to the formation of a cytoplasmic protein complex, according to the disclosure, and will result in the phosphorylation of the reporter phosphorylation site. In one preferred embodiment, the first and the second interaction protein are identical to study homodimerization or homomultimerization of a protein. In another preferred embodiment, the first and the second protein are different, allowing to study protein-protein interactions of heterodimers or heteromultimers.

Compound means any chemical or biological compound, including simple or complex organic or inorganic molecules, peptides, peptido-mimetics, proteins, antibodies, carbohydrates, nucleic acids or derivatives thereof.

Interaction means any interaction, be it direct or indirect. A direct interaction implies a contact between the interaction partners. An indirect interaction means any interaction whereby the interaction partners interact in a complex of more than two compounds. This interaction can be completely indirect, with the help of one or more bridging compounds, or partly indirect, where there is still a direct contact that is stabilized by the interaction of one or more compounds.

Figure 1:
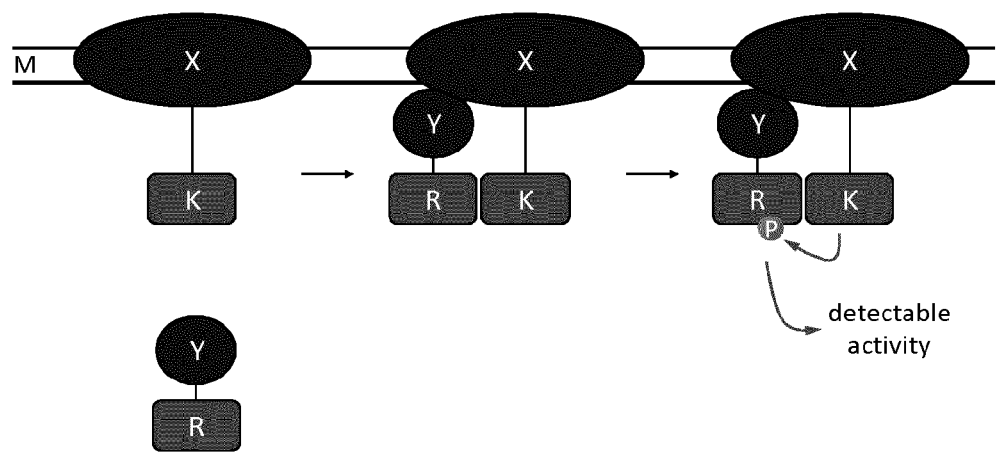
FIG. 1: Schematic representation of different embodiments of the recombinant membrane span protein complex, according to the disclosure. "M" depicts a membrane.
Figure 1:
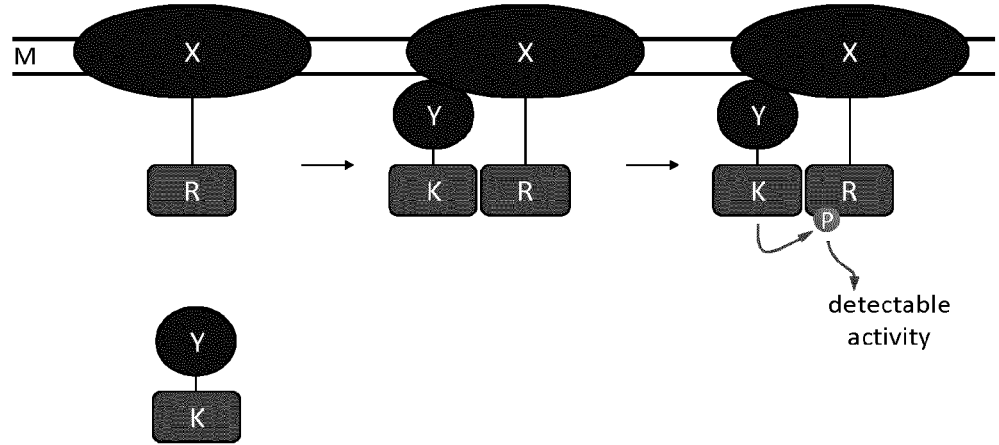
Figure 1:
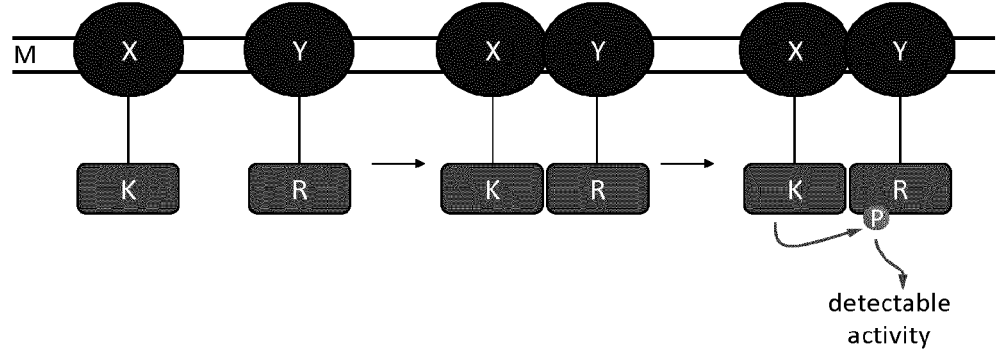

A. A membrane span protein (X) is fused to a constitutive kinase (K) and a polypeptide (Y) is fused to a reporter phosphorylation site (R). Interaction between the membrane span protein X and the polypeptide Y results in the reporter phosphorylation site being phosphorylated (P) by the constitutive kinase, leading to a detectable activity.

B. A membrane span protein (X) is fused to a reporter phosphorylation site (R) and a polypeptide (Y) is fused to a constitutive kinase (K). Interaction between the membrane span protein X and the polypeptide Y results in the reporter phosphorylation site being phosphorylated (P) by the constitutive kinase, leading to a detectable activity.

C. A membrane span protein (X) is fused to a constitutive kinase (K) and a second membrane span protein (Y) is fused to a reporter phosphorylation site (R). Interaction between the membrane span proteins X and Y results in the reporter phosphorylation site being phosphorylated (P) by the constitutive kinase, leading to a detectable activity.

FIG. 2: Detection of the ligand-dependent interaction between human somatostatin receptor 2 (SSTR2) and human beta arrestin 2 (ARRB2) in an assay variant that comprises mutant Tyk2 kinase fusion proteins.

A. Schematic overview of the assay. The membrane span protein (X) is fused to the C-terminal region of Tyk2 comprising the kinase domain, whereas the polypeptide interacting with the membrane span protein (Y) is fused to a fragment of gp130 which contains phosphorylation sites. When membrane span protein X and the polypeptide Y interact, the Tyk2 kinase domain phosphorylates the phosphorylation sites of gp130. STAT3 transcription factors are recruited to these phosphorylated sites and are in turn phosphorylated by the Tyk2 kinase domain, which results in their activation. Dimers of activated STAT3 transcription factors are able to bind the specific rPAPI promoter, which drives the expression of a firefly luciferase reporter gene. The activity of this reporter gene is measured as light production in a luciferase detection assay using a luminometer.

B. Application to the analysis of ligand-dependent interaction between SSTR2 and ARRB2. Cells were transfected with the indicated combination of plasmids, and either left untreated (NS) or treated with increasing doses (0.1-1-10 µM) of somatostatin:
 a) pMet7-HA-Tyk2(C)+pMG2-ARRB2+pXP2d2-rPAPI-luciferase
 b) pMet7-SSTR2-Tyk2(C)-HA+pMG2-SVT+pXP2d2-rPAPI-luciferase
 c) pMet7-SSTR2-Tyk2(C)-HA+pMG2-ARRB2+pXP2d2-rPAPI-luciferase Luciferase activity is shown as fold induction relative to the luciferase activity measured in untreated cells. Error bars indicate standard deviation.

C. Detection of the ligand-dependent interaction between SSTR2 and ARRB2 using an alternative expression vector. Cells were transfected with the indicated combination of plasmids, and either left untreated (NS) or treated with increasing doses (0.1-1-1004) of somatostatin:
 a) pSVSport-HA-Tyk2(C)+pMG2-ARRB2+pXP2d2-rPAPI-luciferase
 b) pSVSport-SSTR2-Tyk2(C)-HA+pMG2-SVT+pXP2d2-rPAPI-luciferase
 c) pSVSport-SSTR2-Tyk2(C)-HA+pMG2-ARRB2+pXP2d2-rPAPI-luciferase Luciferase activity is shown as fold induction relative to the luciferase activity measured in untreated cells. Error bars indicate standard deviation.

D. Dose-response curve of the ligand-dependent interaction between SSTR2 and ARRB2. Cells were transfected with a combination of the plasmids pMet7-SSTR2-Tyk2(C)-HA, pMG2-ARRB2 and pXP2d2-rPAPI-luciferase, and treated with increasing concentrations of somatostatin (SST-14). Luciferase activity is shown as relative light units (rlu). Error bars indicate standard deviation.

Figure 3:
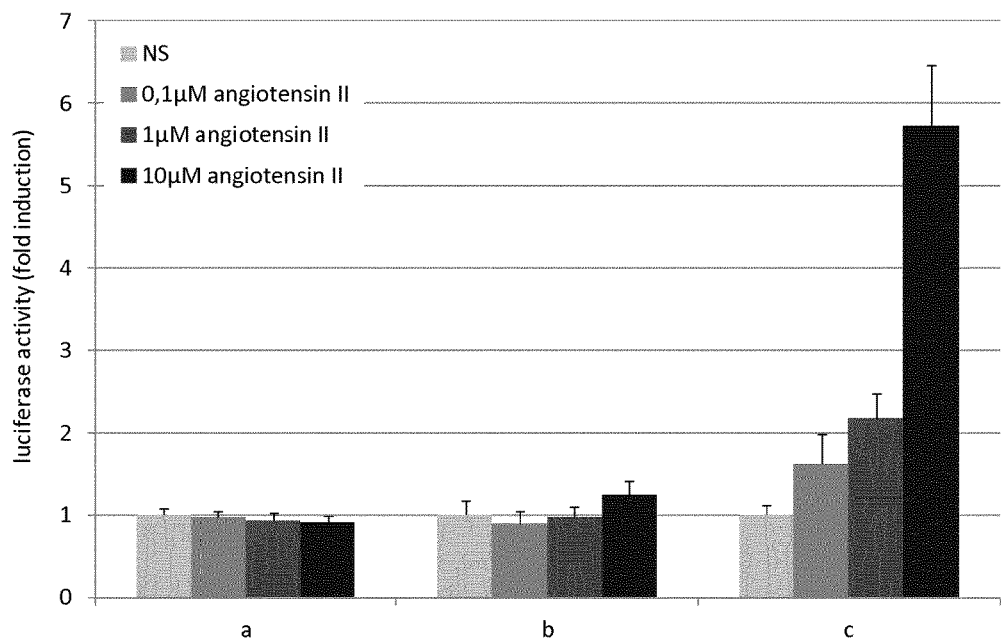
Figure 3:
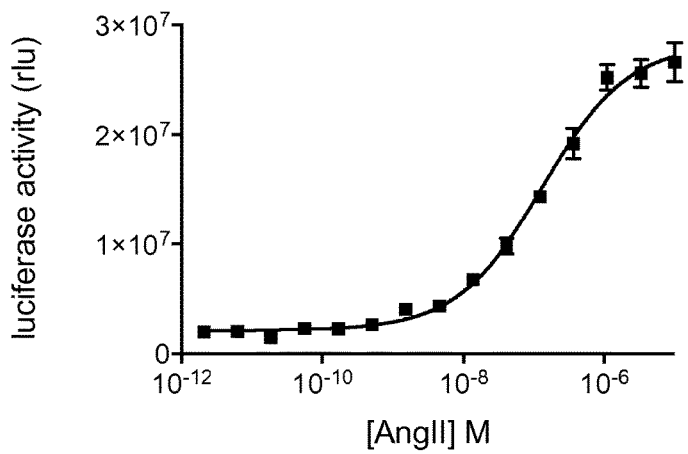

FIG. 3: Analysis of the interaction between human angiotensin receptor 1 (AGTR1) and ARRB2.

A. Detection of the ligand-dependent interaction between AGTR1 and ARRB2. Cells were transfected with the indicated combination of plasmids, and either left untreated (NS) or treated with increasing doses (0.1-1-10 µM) of angiotensin II:
 a) pMet7-HA-Tyk2(C)+pMG2-ARRB2+pXP2d2-rPAPI-luciferase
 b) pMet7-AGTR1-Tyk2(C)-HA+pMG2-SVT+pXP2d2-rPAPI-luciferase
 c) pMet7-AGTR1-Tyk2(C)-HA+pMG2-ARRB2+pXP2d2-rPAPI-luciferase Luciferase activity is shown as fold induction relative to the luciferase activity measured in untreated cells. Error bars indicate standard deviation.

B. Dose-response curve of the ligand-dependent interaction between AGTR1 and ARRB2. Cells were transfected with a combination of the plasmids pMet7-AGTR1-Tyk2(C)-HA, pMG2-ARRB2 and pXP2d2-rPAPI-luciferase, and treated with increasing concentrations of angiotensin II (AngII). Luciferase activity is shown as relative light units (rlu). Error bars indicate standard deviation.

Figure 4:
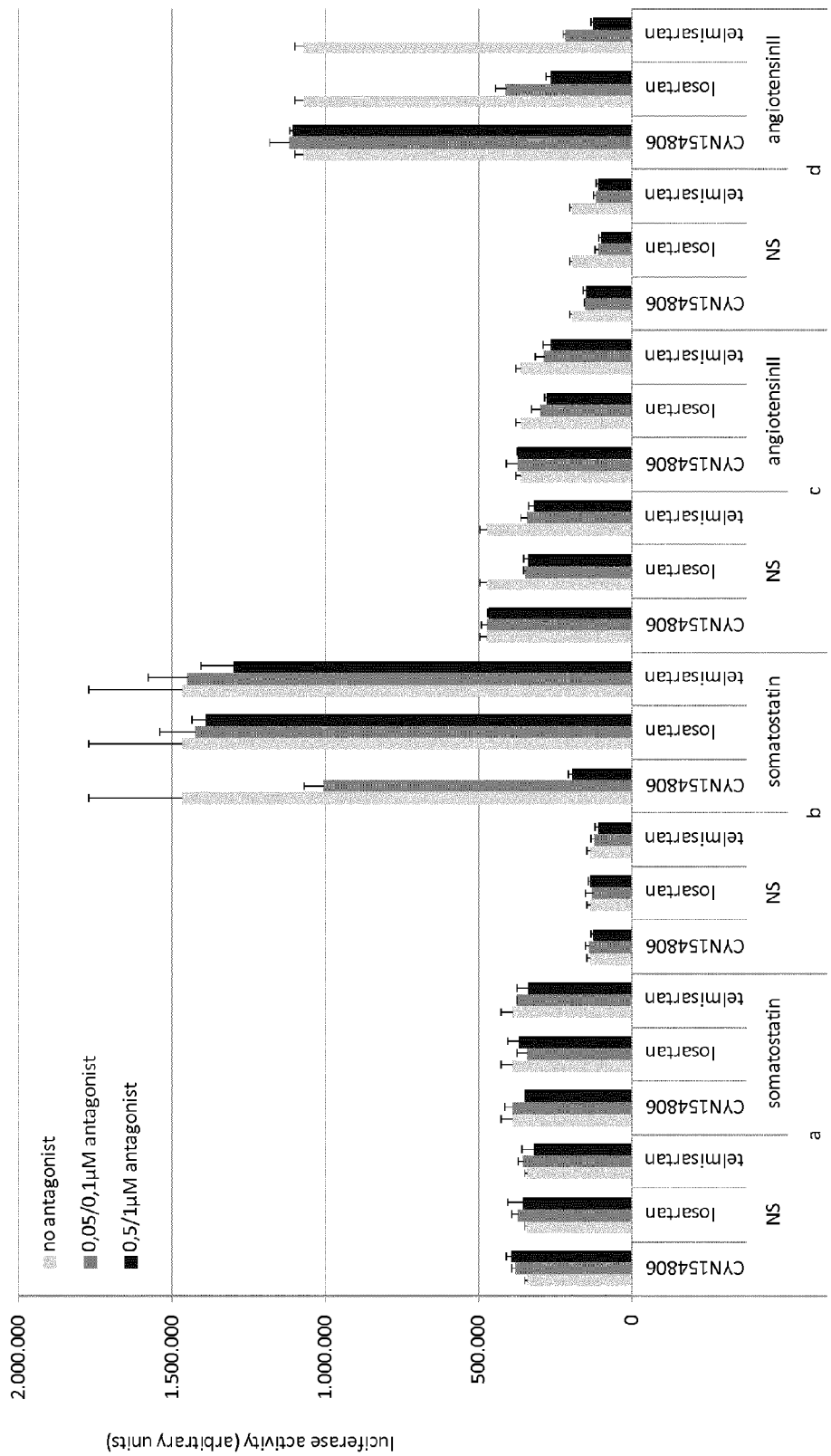

FIG. 4: Evaluation of the effect of GPCR antagonists on the interaction between GPCRs and ARRB2. Cells were transfected with the indicated combination of plasmids, and treated with the indicated combinations of GPCR ligand and antagonist (ligand: 1 µM somatostatin for transfections a and b, 10 µM angiotensin II for transfections c and d; antagonists: 0.05 or 0.5 µM CYN154806; 0.1 or 1 µM losartan or telmisartan):
 a) pMet7-SSTR2-Tyk2(C)-HA+pMG1-EFHA1+pXP2d2-rPAPI-luciferase
 b) pMet7-SSTR2-Tyk2(C)-HA+pMG2-ARRB2+pXP2d2-rPAPI-luciferase
 c) pMet7-AGTR1-Tyk2(C)-HA+pMG1-EFHA1+pXP2d2-rPAPI-luciferase
 d) pMet7-AGTR1-Tyk2(C)-HA+pMG2-ARRB2+pXP2d2-rPAPI-luciferase Luciferase activity is shown as arbitry light units. Error bars indicate standard deviation.

Figure 5:
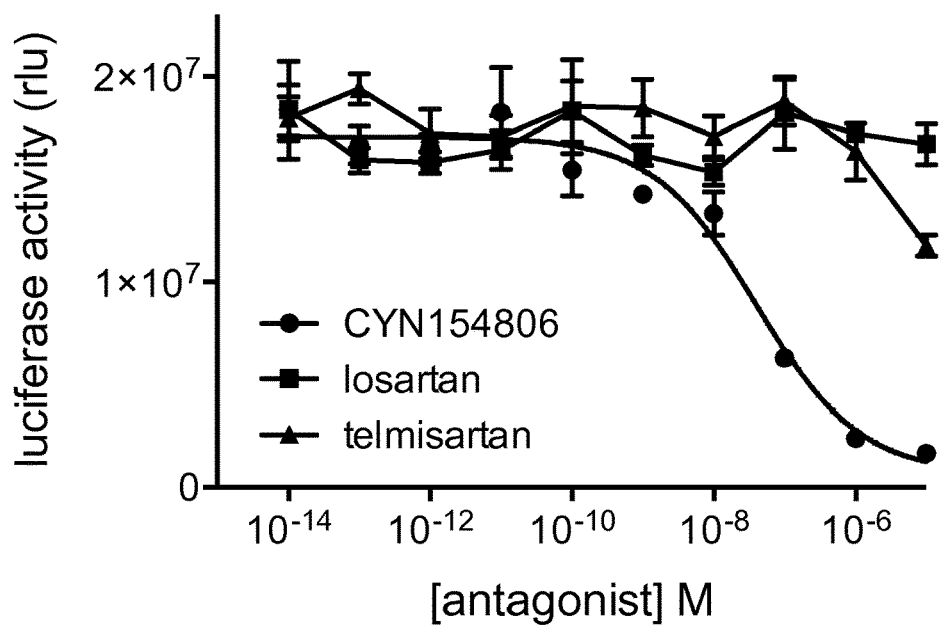
Figure 5:
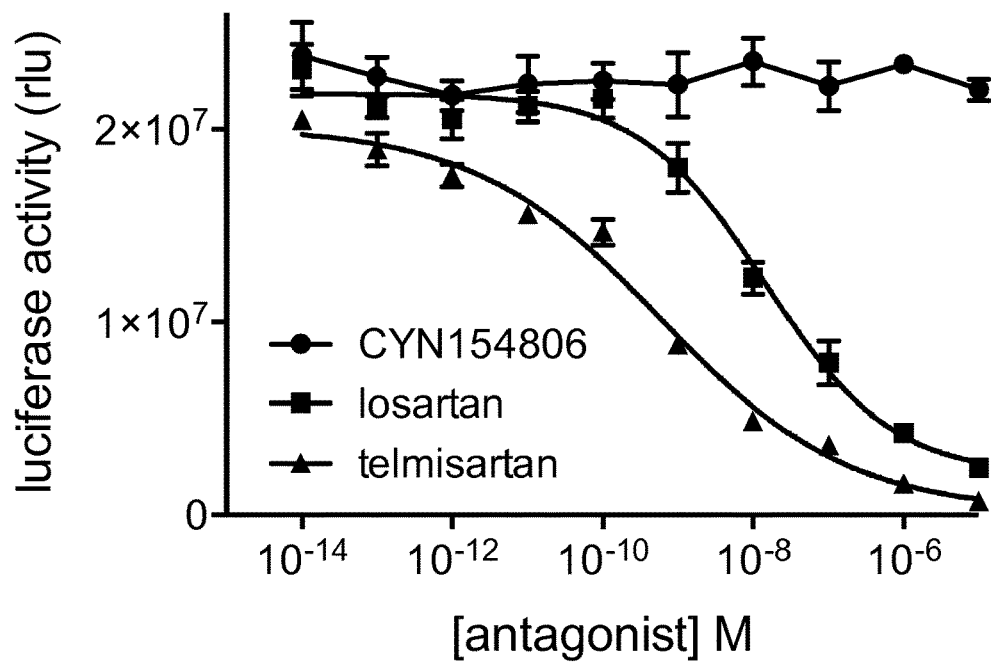

FIG. 5: Dose-dependent effect of GPCR antagonists on the detection of the interaction between GPCRs and ARRB2.

A. Analysis of the effect of GPCR antagonists in an assay measuring the interaction between SSTR2 and ARRB2. Cells were transfected with the following combination of plasmids: pMet7-SSTR2-Tyk2(C)-HA+pMG2-ARRB2+pXP2d2-rPAPI-luciferase. Cells were either left untreated, treated with 10 µM somatostatin or treated with a combination of 10 µM somatostatin and increasing doses ($10^{-13}$M up to $10^{-6}$M) of either GPCR antagonist (CYN154806, losartan, telmisartan). Luciferase activity is shown as relative light units (rlu). Error bars indicate standard deviation.

B. Analysis of the effect of GPCR antagonists in an assay measuring the interaction between AGTR1 and ARRB2. Cells were transfected with the following combination of plasmids: pMet7-AGTR1-Tyk2(C)-HA+pMG2-ARRB2+pXP2d2-rPAPI-luciferase. Cells were either left untreated, treated with 10 µM angiotensin II or treated with a combination of 10 µM angiotensin II and increasing doses ($10^{-13}$M up to $10^{-6}$M) of either GPCR antagonist (CYN154806, losartan, telmisartan). Luciferase activity is shown as relative light units (rlu). Error bars indicate standard deviation.

FIG. 6: Analysis of ERN1 dimerization.

A. Detection of ERN1 dimerization upon induction of ER (endoplasmatic reticulum)-stress by treatment with tunicamycin. Cells were transfected with the following plasmids:
 a) pcDNA5/FRT/TO-ERN1-Tyk2(C)-HA+pMG1+pXP2d2-rPAPI-luciferase
 b) pcDNA5/FRT/TO-ERN1-Tyk2(C)-HA+pMG2C-ERN1 pXP2d2-rPAPI-luciferase After transfection, cells were treated with 0-0.5-1-2 µg/ml tunicamycin, final concentration. Error bars indicate standard deviation.

B. Detection of ERN1 dimerization upon induction of ER-stress by treatment with tunicamycin. Cells were transfected with the following plasmids:

a) pcDNA5/FRT/TO-ERN1-Tyk2(C)-HA+pMG1+pXP2d2-rPAPI-luciferase b) pcDNA5/FRT/TO-ERN1-Tyk2(C)-HA+pMG2C-ERN1 pXP2d2-rPAPI-luciferase c) pcDNA5/FRT/TO-ERN1-Tyk2(C)-HA+pMG2C-ERN1cyt+pXP2d2-rPAPI-luciferase After transfection, cells were treated with increasing doses tunicamycin. Luciferase activity is shown as fold induction relative to the luciferase signal obtained in cells transfected with unfused gp130 (transfection a) and treated with the same concentration tunicamycin. Error bars indicate standard deviation. Expression of Tyk2(C) and gp130 fusion constructs was evaluated through Western blot applying anti-HA and anti-gp130 antibodies, respectively. Beta-actin expression was stained as a control for equal loading.

C. Analysis of ERN1 structure-function relationship. Cells were transfected with the pXP2d2-rPAPI-luciferase plasmid combined with the indicated Tyk2(C) fusion constructs (pcDNA5/FRT/TO-ERN1-Tyk2(C)-HA, pcDNA5/FRT/TO-ERN1(K599A)-Tyk2(C)-HA or pcDNA5/FRT/TO-ERN1(D123P)-Tyk2(C)-HA) and gp130 fusion constructs (pMG1, encoding unfused gp130 or pMG2C-ERN1 encoding ERN1-gp130), and treated with either tunicamycin or vehicle control (DMSO). Luciferase activity is shown as fold induction relative to the luciferase signal obtained in cells transfected with unfused gp130. Error bars indicate standard deviation. Expression of Tyk2(C) fusion constructs was evaluated through Western blot applying an anti-HA antibody. Beta-actin expression was stained as a control for equal loading.

D. Detection of disruptors of ERN1 dimerization. Cells were transfected with the following plasmids:

a) pcDNA5/FRT/TO-ERN1-Tyk2(C)-HA+pMG1+pXP2d2-rPAPI-luciferase b) pcDNA5/FRT/TO-ERN1-Tyk2(C)-HA+pMG2C-ERN1 pXP2d2-rPAPI-luciferase After transfection, cells were treated with tunicamycin or vehicle control (DMSO) combined with increasing doses of Irestatin 9389. Luciferase activity of cells transfected with gp130-fused ERN1 (transfection b) is shown as fold induction relative to the luciferase signal obtained in cells transfected with unfused gp130 (transfection a) and treated with the same concentration of vehicle or tunicamycin with Irestatin 9389. Error bars indicate standard deviation.

Figure 7:
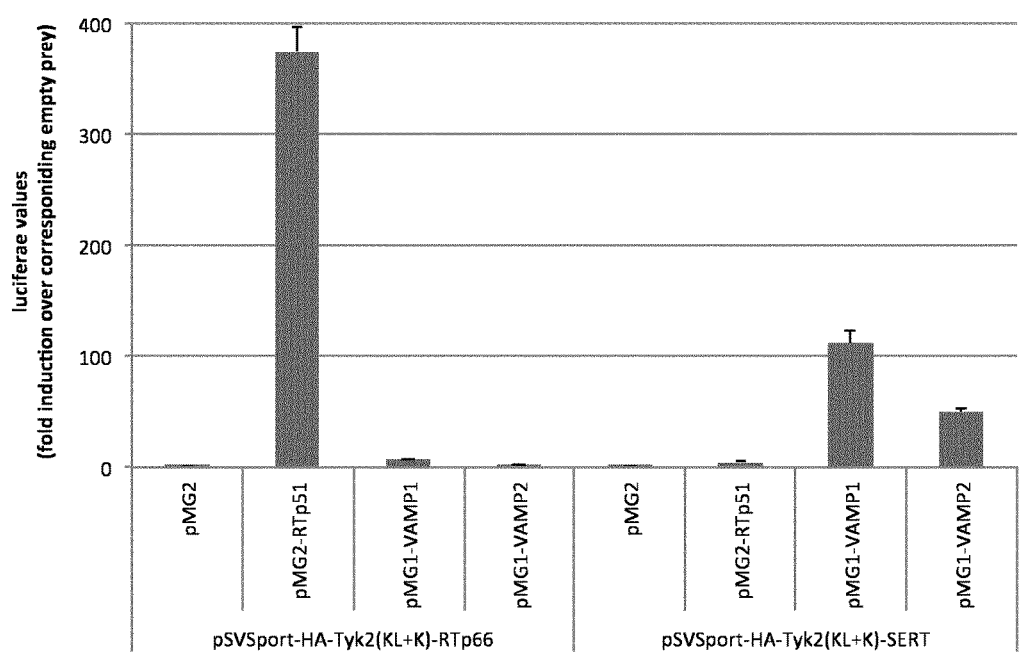

FIG. 7: Detection of the interaction between the serotonin transporter (SERT) and synaptobrevins 1 and 2 (VAMP1 and VAMP2). Cells were transfected with the pXP2d2-rPAPI-luciferase plasmid combined with the indicated Tyk2(C) and gp130 fusion constructs. Luciferase activity is shown as fold induction relative to the luciferase signal obtained in cells transfected with unfused gp130 (pMG2). Error bars indicate standard deviation.

EXAMPLES

Materials and Methods to the Disclosure
Plasmids Used in the Examples

A first type of plasmids express chimeric proteins consisting of an HA-tagged C-terminal portion of human Tyk2 fused at its N-terminus to the membrane span protein and are generated in the pMet7 vector, which contains a strong constitutive hybrid SRα promoter (Takebe et al., 1988). A pMet7-dest-Tyk2(C)-HA Gateway destination vector was constructed by first amplifying the Gateway cassette from the pMG1 Gateway destination vector (Lievens et al., 2009) using primers 1 and 2 (see Table below). These primers contained an AgeI and PspOMI restriction enzyme recognition site, respectively, and these enzymes were used to digest the PCR amplicon. Next, the sequence encoding the C-terminal end of human Tyk2 comprising the kinase domain (starting from amino acids 589 and omitting the stop codon) was amplified by PCR on cDNA from HEK293 cells with primers 3 and 4 (see Table below). The former primer contained a NotI restriction site, whereas the latter contained an HA-tag coding sequence as well as an XbaI restriction enzyme recognition site. The PCR amplicon was digested with NotI and XbaI and, together with the AgeI and PspOMI cut fragment described above, ligated in the AgeI-XbaI cut pMet7 vector to generate the pMet7-dest-Tyk2(C)-HA Gateway destination vector. The pMet7-SSTR2-Tyk2(C)-HA and pMet7-AGTR1-Tyk2(C)-HA plasmids were produced by Gateway recombination mediated transfer of the full length sequence of human SSTR2 and AGTR1, respectively, from entry vectors of the hORFeome collection (Lamesch et al., 2007) into the pMet7-dest-Tyk2(C)-HA Gateway destination vector. Using the restriction enzymes EcoRI and MluI, the SSTR2-Tyk2(C)-HA insert (SEQ ID NO:3) of pMet7-SSTR2-Tyk2(C)-HA was subcloned into pSVSport (Invitrogen) to generate pSVSport-SSTR2-Tyk2(C)-HA. The AGTR1-Tyk2-HA construct is depicted in SEQ ID NO:4.

The control plasmids pMet7-HA-Tyk2(C) and pSVSport-HA-Tyk2(C), which are made of the same C-terminal Tyk2 fragment as described above, an HA-tag at the 5' end and a multiple cloning site at the 3' end were generated by PCR amplification of the Tyk2 sequence on the pMet7-dest-Tyk2(C)-HA template vector using primers 5 and 6 (see Table below). These primers contain an MfeI site and an HA-tag coding sequence together with an XbaI restriction site, respectively. The MfeI-XbaI digested amplicon was ligated both in the EcoRI-XbaI digested pMet7 vector to result in pMet7-HA-Tyk2(C), and in the EcoRI-XbaI digested pSVSport vector (Invitrogen) to generate pSVSport-HA-Tyk2(C).

pSVSport-HA-Tyk2(C)-RTp66 was produced by transfer of the RTp66 insert from pMG2-RTp66 (Pattyn et al., 2008) to pSVSport-HA-Tyk2(C) using the EcoRI and NotI restriction sites. The HA-Tyk2(C)-RTp66 construct is depicted in SEQ ID NO:28. To generate the pSVSport-HA-Tyk2(C)-SERT plasmid, human SERT was amplified on a SERT containing plasmid template using primers 18 and 19, containing EcoRV and NotI restriction sites, respectively. The amplicon was digested with EcoRV, rendered blunt end by the use of Pfu DNA polymerase and subsequently cut with NotI. This fragment was ligated in pSVSport-HA-Tyk2(C) that was cut with EcoRI, rendered blunt end through Pfu DNA Polymerase treatment and subsequently cut with NotI. The HA-Tyk2(C)-SERT construct is shown in SEQ ID NO:29.

To generate the pcDNA5/FRT/TO-ERN1-Tyk2(C)-HA plasmid, human ERN1 was amplified with primers 9 and 10, containing HindIII and NotI restriction enzyme recognition sites, respectively, using an ERN1 entry clone from the hORFeome collection (Lamesch et al., 2007) as a template. The sequence encoding the C-terminal end of human Tyk2 comprising the kinase domain (starting from amino acids 589 and omitting the stop codon) was amplified by PCR on cDNA from HEK293 cells with primers 11 and 12. The former primer contained a NotI restriction site, whereas the latter contained an HA-tag coding sequence as well as an ApaI restriction enzyme recognition site. The PCR amplicon was digested with NotI and ApaI and, together with the HindIII and NotI cut ERN1 fragment described above, ligated into the HindIII-ApaI cut pcDNA5/FRT/TO vector (Invitrogen) to generate the pcDNA5/FRT/TO-ERN1-Tyk2 (C)-HA expression plasmid. The ERN1-Tyk2-HA fusion is depicted in SEQ ID NO:5. The pcDNA5/FRT/TO-ERN1 (K599A)-Tyk2(C)-HA plasmid was generated similarly, by amplifying ERN1 from a plasmid containing ERN1 (K599A) instead of WT ERN1. The pcDNA5/FRT/TO-ERN1(D123P)-Tyk2(C)-HA plasmid was generated through site-directed mutagenesis of the pcDNA5/FRT/TO-ERN1-Tyk2(C)-HA plasmid using primers 16 and 17. The amino acid sequence of the ERN1(K599A)-Tyk2(C)-HA en ERN1 (D123P)-Tyk2(K)-HA fusion proteins is depicted in SEQ ID NOS:30 and 31, respectively.

The plasmids encoding the fusions with the second interacting polypeptide were of the type also used in MAPPIT, designated pMG2 (WO0190188, Eyckerman et al., 2001; Lemmens et al., 2003). These plasmids encode fusion proteins of the second interacting polypeptide coupled to a fragment of the human gp130 cytokine receptor chain, which contains multiple tyrosine residues that, upon phosphorylation, make up recruitment sites for STAT3. The SV40 large T containing control plasmid pMG2-SVT was generated by transfer of the SVT insert from the previously described pMG1-SVT plasmid (Eyckerman et al., 2001) into the pMG2 vector using EcoRI and NotI restriction enzymes. Human ARRB2 was PCR amplified on an ARRB2 entry clone from the hORFeome collection (Lamesch et al., 2007) using primers 7 and 8 (see Table below) and exchanged with the SVT insert of pMG2-SVT using EcoRI and NotI restriction sites to generate pMG2-ARRB2. pMG1-EFHA1, pMG1-VAMP1 and pMG1-VAMP2 were generated by Gateway recombination mediated transfer of the full length sequences of human EFHA1, VAMP1 and VAMP2, respectively, from entry vectors of the hORFeome collection (Lamesch et al., 2007) into a Gateway compatible version of the pMG1 vector as described earlier (Lievens et al., 2009). The flag tag-gp130-ARRB2, flag tag-gp130-VAMP1 and flag tag-gp130-VAMP2 fusion constructs are depicted in SEQ ID NOS:6, 32 and 33, respectively.

The pMG2C-ERN1 plasmid encoding a fusion protein of the human ERN1 protein N-terminally coupled to a fragment of the human gp130 cytokine receptor chain was generated by PCR amplification of the ERN1 encoding sequence on an ERN1 entry clone from the hORFeome collection (Lamesch et al., 2007) using primers 13 and 14 and cloning this into a MAPPIT vector containing a gp130 encoding sequence at the 3' end of a Flag-tag encoding sequence and a multi-cloningsite (Pattyn et al., 2008) using EcoRI and XhoI restriction enzymes. The flag tag-ERN1-gp130 fusion construct is depicted in SEQ ID NO:7. The pMG2C-ERN1cyt plasmid encoding a fusion protein of the cytoplasmic portion of the human ERN1 protein fused N-terminally to the gp130 fragment was produced by amplifying the ERN1 cytoplasmic domain on an ERN1 entry clone (see higher) using primers 15 and 14 and cloning this into a MAPPIT vector containing a gp130 encoding sequence using EcoRI and XhoI restriction enzymes, similarly to described above. The flag-tag-ERN1cyt-gp130 fusion construct is depicted in SEQ ID NO:34.

pMG2-RTp51 has been described elsewhere (Pattyn et al., 2008). The flag tag-gp130-RTp51 fusion construct sequence is shown in SEQ ID NO:35. The pMG1 and pMG2 plasmids encoding an unfused gp130 receptor fragment were obtained by cutting out the MAPPIT prey insert of a pMG1 vector using EcoRI and XhoI or of a pMG2 vector using EcoRI and SalI, respectively, blunting the vector backbone through Pfu DNA Polymerase and self-ligation. The amino acid sequence of the polypeptide encoded by pMG1 and pMG2 is depicted in SEQ ID NOS:36 and 37, respectively.

The reporter plasmid pXP2d2-rPAPI-luciferase used in the examples contains the STAT3-dependent rPAPI (rat Pancreatitis-Associated Protein I) promoter driving a firefly luciferase reporter gene as described previously (WO0190188, Eyckerman et al., 2001).

Transfection Procedure

Transfections were carried out using a standard calcium phosphate method. HEK293-T cells were seeded in black tissue-culture treated 96-well plates at 10.000 cells/well in 100 µl culture medium (DMEM supplemented with 10% FCS). Twenty-four hours later, plasmid DNA mixes were prepared that contained plasmids encoding fusion proteins with the first and second interacting proteins and reporter plasmids. The DNA was supplemented with 5 µl 2.5M $CaCl_2$ and double distilled water to a final volume of 50 µl. This mixture was added drop wise to 50 µl 2xHeBS buffer (280 mM NaCl, 1.5 mM $Na_2HPO_4$, 50 mM Hepes; pH 7.05) while vigorously vortexing. After incubation at room temperature for 15 min. to allow DNA precipitates to form, the solution was added to the cells at 10 µl/well. Cells were incubated at 37° C., 8% CO2. Twenty-four hours after transfection, cells were treated with the indicated amounts of ligand, either alone or combined with the indicated amount of antagonist. In the case of Irestatin 9389, cells were pre-treated with the antagonist before adding vehicle (DMSO) or tunicamycin. Another twenty-four hours later, luciferase activity was measured using the Luciferase Assay System kit (Promega) on a TopCount luminometer (Perkin-Elmer). Each transfection was done in triplicate and the average of the luciferase activity readings was used in the calculations.

Induction of Dimerization

Tunicamycin (Sigma T7765; 2 mg/ml stock in DMSO) was diluted in culture medium and added to the cells 24 h prior to luciferase signal read-out.

(Ant)Agonists Applied in the Examples

Somatostatin (Sigma 51763) and angiotensin II (Sigma A9525) were solubilized in PBS to make stock concentrations of 500 µM and 10 mM, respectively. CYN154806 trifluoroacetate salt (Sigma C2490) and losartan potassium (Fluka 61188) were dissolved in PBS at a final concentration of 500 µM and 10 mM, respectively. Telmisartan (Sigma T8949) was dissolved in DMSO at a concentration of 10 mM. Irestatin 9389 (Axxon Medchem) was dissolved in DMSO at a concentration of 50 mM.

Western Blotting

Cells were lysed in 1 xCCLR buffer (25 mM Tris—phosphate (pH 7.8), 2 mM DTT, 2 mM CDTA (trans-1,2-diaminocyclo-hexane-N,N,N,N-tetra acetic acid), 10% glycerol, 1% Triton X-100). Lysates were centrifuged and supernatants were separated by SDS-PAGE. Proteins were detected by immunoblotting using rat anti-HA (Roche), rabbit anti-gp130 (Santa Cruz Biotechnology) or mouse anti-beta-actin (Sigma) antibodies.

| Oligonucleotide primer | Sequence (5' > 3') |
|---|---|
| 1 | CCCACCGGTCCGGAATTGACAAGTTTGTACAAAAAAGC (SEQ ID NO: 9) |
| 2 | GGGGGGCCCCAACCACTTTGTACAAGAAAGC (SEQ ID NO: 10) |
| 3 | CCCGCGGCCGCTGGCGGTTCGATCACCCAGCTGTCCCACTTGG (SEQ ID NO: 11) |
| 4 | TCTAGACTAAGCATAATCTGGAACATCATATGGATACTCGAGGC ACACGCTGAACACTGA AGG (SEQ ID NO: 12) |
| 5 | CCCCAATTGACCATGTATCCATATGATGTTCCAGATTATGCTTTA ATTAAAATCACCCAGCTGTCCCACTTGG (SEQ ID NO: 13) |
| 6 | GGGTCTAGAGCGGCCGCACCGGTCTTAATTAAGTCGACGAATTC GCACACGCTGAACACT GAAG (SEQ ID NO: 14) |
| 7 | CCCAAGCTTGAATTCACCATGGGGGAGAAACCCGGGAC (SEQ ID NO: 15) |
| 8 | GGGGCGGCCGCCTAGCAGAGTTGATCATCATAG (SEQ ID NO: 16) |
| 9 | CCCAAGCTTGGTACCACCATGCCGGCCCGGCGGCTGCTG (SEQ ID NO: 17) |
| 10 | CCCGCGGCCGCGCTAGCGAGGGCGTCTGGAGTCACTGG (SEQ ID NO: 18) |
| 11 | CCCGCGGCCGCTGGCGGTTCGATCACCCAGCTGTCCCACTTGG (SEQ ID NO: 19) |
| 12 | GGGCCCCTAAGCATAATCTGGAACATCATATGGATACTCGAGGC ACACGCTGAACACTGA AGG (SEQ ID NO: 20) |
| 13 | CCCGAATTCATGCCGGCCCGGCGGCTGCTG (SEQ ID NO: 21) |
| 14 | CCCCTCGAGGGGAGGGCGTCTGGAGTCACTGG (SEQ ID NO: 22) |
| 15 | CCCGAATTCTTCTGTCCCAAGGATGTCCTG (SEQ ID NO: 23) |
| 16 | GGGTAAAAAGCAGCCCATCTGGTATGTTATTGACC (SEQ ID NO: 24) |
| 17 | GGTCAATAACATACCAGATGGGCTGCTTTTTACCC (SEQ ID NO: 25) |
| 18 | CCCGATATCTATGGAGACGACGCCCTTGAA (SEQ ID NO: 26) |
| 19 | GGGGCGGCCGCTTACACAGCATTCAAGCGGA (SEQ ID NO: 27) |

Example 1

Detection of the Ligand-Dependent Interaction Between SSTR2 and ARRB2

G-protein coupled receptors (GPCRs) are integral membrane proteins that contain 7 transmembrane domains. Upon binding of the appropriate ligand GPCRs are activated, leading to the recruitment of cytoplasmic beta arrestin proteins. In order to determine whether the assay can detect the somatostatin-dependent interaction between the GPCR SSTR2 and ARRB2, the following combinations of plasmids were transfected (FIG. 2A; 250 ng of the Tyk2(C) fusion construct, 250 ng of the gp130 fusion construct and 50 ng of the luciferase reporter construct) according to the methods described above:

a) pMet7-HA-Tyk2(C)+pMG2-ARRB2+pXP2d2-rPAPI-luciferase b) pMet7-SSTR2-Tyk2(C)-HA+pMG2-SVT+pXP2d2-rPAPI-luciferase c) pMet7-SSTR2-Tyk2(C)-HA+pMG2-ARRB2+pXP2d2-rPAPI-luciferase Transfected cells were either left untreated (NS) or treated with increasing doses (0.1-1-1004) of the SSTR2 agonist somatostatin. The fold induction for each sample was calculated as the ratio of the measured luciferase activity relative to the luciferase activity for the untreated sample of the same transfection. The results (FIG. 2B) show a clear ligand dose-dependent signal specifically in the cells co-transfected with both the SSTR2-Tyk2(C) and gp130-ARRB2 fusion constructs (transfection c). No signal was observed when either of the fusion constructs was transfected in combination with a negative control fusion construct (gp130-ARRB2 fusion construct combined with an unfused Tyk2(C) construct in transfection a, or SSTR2-Tyk2(C) fusion construct together with a fusion of gp130 to a fragment of the SV40 large T protein in b).

The assay was further optimized by transferring the Tyk2(C) fusion construct into another vector system (pSVSport) and testing the resulting constructs in a similar experiment as described above. The following combinations of plasmids were transfected (500 ng of the Tyk2(C) fusion construct, 250 ng of the gp130 fusion construct and 50 ng of the luciferase reporter construct) according to the methods described above:

a) pSVSport-HA-Tyk2(C)+pMG2-ARRB2+pXP2d2-rPAPI-luciferase
    b) pSVSport-SSTR2-Tyk2(C)-HA+pMG2-SVT+pXP2d2-rPAPI-luciferase
    c) pSVSport-SSTR2-Tyk2(C)-HA+pMG2-ARRB2+pXP2d2-rPAPI-luciferase Transfected cells were either left untreated (NS) or treated with increasing doses (0.1-1-10 µM) of the SSTR2 agonist somatostatin, and signals were calculated as indicated above. The resulting graph (FIG. 2C) shows strong and specific ligand dose-dependent signals up to 30-fold stronger compared to untreated samples.

Figure 2A:
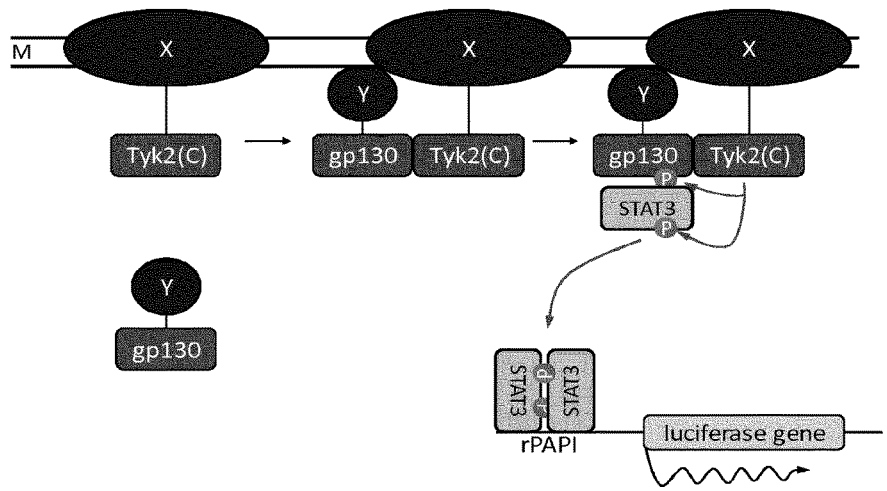
Figure 2B:
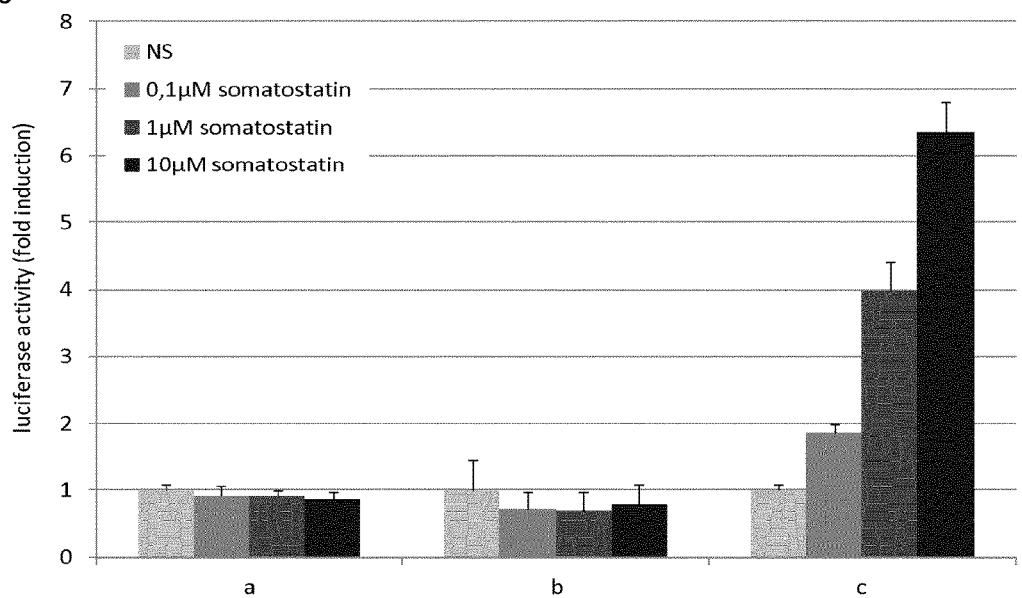
Figure 2C:
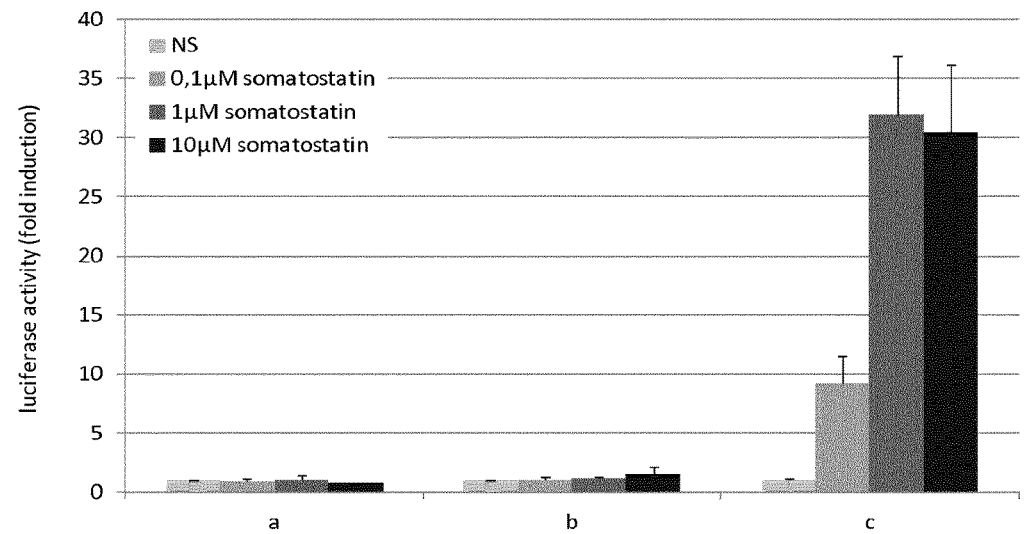
Figure 2D:
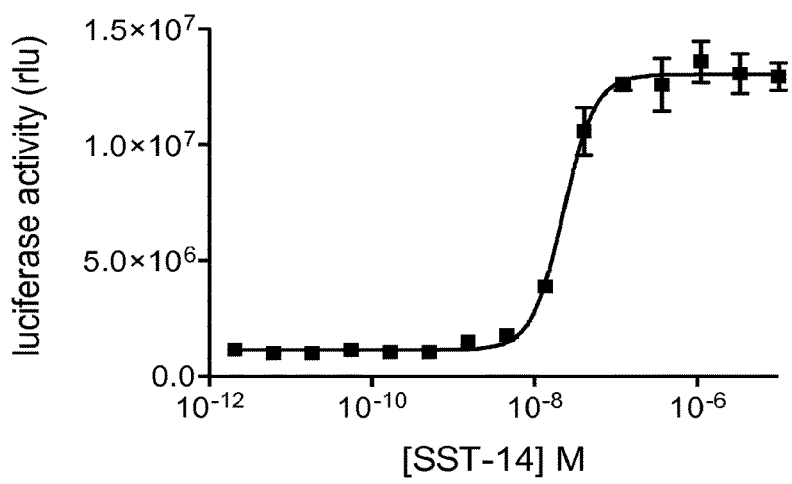

In another experiment, cells were transfected with 31 ng of the pMet7-SSTR2-Tyk2(C)-HA plasmid, 250 ng of the pMG2-ARRB2 plasmid and 50 ng of the pXP2d2-rPAPI-luciferase plasmid, and transfected cells were treated with a concentration gradient of somatostatin (a ⅓ serial dilution series down from 10 µM). The resulting dose-response curve is shown in FIG. 2D.

Together, these data illustrate that the method is able to detect ARRB2 recruitment to the SSTR2 integral membrane GPCR induced by treatment with the SSTR2 agonist somatostatin.

Example 2

Detection of the Ligand-Dependent Interaction Between AGTR1 and ARRB2

Likewise as in example 1, the ligand-induced recruitment of ARRB2 to another GPCR family member, AGTR1, was tested by transfecting the following combinations of plasmids (250 ng of the Tyk2(C) fusion construct, 250 ng of the gp130 fusion construct and 50 ng of the luciferase reporter construct) according to the methods described above:

a) pMet7-HA-Tyk2(C)+pMG2-ARRB2+pXP2d2-rPAPI-luciferase
    b) pMet7-AGTR1-Tyk2(C)-HA+pMG2-SVT+pXP2d2-rPAPI-luciferase
    c) pMet7-AGTR1-Tyk2(C)-HA+pMG2-ARRB2+pXP2d2-rPAPI-luciferase Transfected cells were either left untreated (NS) or treated with increasing doses (0.1-1-10 µM) of angiotensin II, an AGTR1 agonist. The fold induction for each sample was calculated as the ratio of the measured luciferase activity relative to the luciferase activity for the untreated sample of the same transfection. The results (FIG. 3A) show a clear ligand dose-dependent signal specifically in the cells cotransfected with both the AGTR1-Tyk2(C) and gp130-ARRB2 fusion constructs (transfection c). No signal was observed when either of the fusion constructs was transfected in combination with a negative control fusion construct (gp130-ARRB2 fusion construct combined with an unfused Tyk2(C) construct in transfection a, or AGTR1-Tyk2(C) fusion construct together with a fusion of gp130 to a fragment of the SV40 large T protein in b).

In another experiment, cells were transfected with 62 ng of the pMet7-AGTR1-Tyk2(C)-HA plasmid, 250 ng of the pMG2-ARRB2 plasmid and 50 ng of the pXP2d2-rPAPI-luciferase plasmid, and transfected cells were treated with a concentration gradient of angiotensin II (a ⅓ serial dilution series down from 10 µM). The resulting dose-response curve is shown in FIG. 3B.

These results confirm the method's ability to detect the interaction between the AGTR1 integral membrane protein and ARRB2, in a ligand-dependent manner.

Example 3

Effect of GPCR Antagonists on the Detection of the Interaction Between GPCRs and ARRB2

In order to test whether the assay allows evaluating the effect of GPCR antagonists, GPCR ligands were combined with specific antagonists of SSTR2 and AGTR1 in the assay for detection of their interaction with ARRB2. A peptide antagonist that specifically inhibits SSTR2 activation was tested (CYN154806), together with two small molecule AGTR1-selective antagonists (losartan and telmisartan).

Cells were transfected with the following combinations of plasmids (250 ng of the Tyk2(C) fusion construct, 250 ng of the gp130 fusion construct and 50 ng of the luciferase reporter construct) according to the methods described above:

a) pMet7-SSTR2-Tyk2(C)-HA+pMG1-EFHA1+pXP2d2-rPAPI-luciferase
    b) pMet7-SSTR2-Tyk2(C)-HA+pMG2-ARRB2+pXP2d2-rPAPI-luciferase
    c) pMet7-AGTR1-Tyk2(C)-HA+pMG1-EFHA1+pXP2d2-rPAPI-luciferase
    d) pMet7-AGTR1-Tyk2(C)-HA+pMG2-ARRB2+pXP2d2-rPAPI-luciferase One day after transfection, cells were treated with combinations of GPCR ligand and antagonist (ligand: 1 µM somatostatin for transfections a and b, 10 µM angiotensin II for transfections c and d; antagonists: 0.05 or 0.5 µM CYN154806; 0.1 or 1 µM losartan or telmisartan), and luciferase was measured one day after treatment. The results are shown in FIG. 4 and clearly indicate the specific inhibition by the corresponding antagonist of the GPCR-ARRB2 interactions. The interaction between SSTR2 and ARRB2 (transfection b) can be specifically inhibited by the SSTR2-selective antagonist CYN154806, whereas the AGTR1-specific antagonists losartan and telmisartan have no effect. Conversely, AGTR1-ARRB2 interaction as detected by the assay (transfection d) can be selectively inhibited by the AGTR1-specific antagonists losartan and telmisartan, whereas the SSTR2-selective antagonist CYN154806 has no effect. In both cases, the inhibition through application of the antagonists goes down to background levels observed for cells that had not been treated with GPCR ligand (NS). The inhibitory effect is specific for the GPCR-ARRB2 interaction, as the signal obtained for control interactions of the GPCR-Tyk2(C) fusion construct with a positive control gp130 fusion construct containing EFHA1 (which binds to Tyk2(C) itself), are not affected by the GPCR antagonists.

In a second experiment (shown in FIG. 5), a dose-response curve was generated for the different GPCR antagonists. Cells were transfected with 125 ng of the pMet7-SSTR2-Tyk2(C)-HA or pMet7-AGTR1-Tyk2(C)-HA fusion construct, 250 ng of the pMG2-ARRB2 gp130 fusion construct and 50 ng of the pXP2d2-rPAPI-luciferase reporter plasmid, according to the methods described above. Cells were either left untreated, treated with 10 µM of the appropriate ligand (somatostatin in the case of SSTR2 and angiotensin II in the case of AGTR1) or treated with a combination of the cognate ligand and increasing doses ($10^{-13}$ M up to $10^{-6}$ M) of either GPCR antagonist (CYN154806, losartan, telmisartan). The results are presented in FIG. 5A (for the interaction between SSTR2 and ARRB2) and FIG. 5B (for the interaction between AGTR1 and ARRB2). Again, these data clearly indicate the specific inhibition by the corresponding antagonist of the GPCR-ARRB2 interactions. The interaction between SSTR2 and ARRB2 can be specifically and completely inhibited by the SSTR2-selective antagonist CYN154806, whereas the AGTR1-specific antagonists losartan and telmisartan have no effect. Conversely, AGTR1-ARRB2 interaction as detected by the assay can be selectively and completely inhibited by the AGTR1-specific antagonists losartan and telmisartan, whereas the SSTR2-selective antagonist CYN154806 has no effect. It is of note that the observed stronger effect of telmisartan compared to losartan in this assay corresponds with the reported higher binding affinity of telmisartan versus losartan towards AGTR1 (Kakuta et al., 2005).

Together, these results confirm the specificity of the GPCR-ARRB2 interactions as detected by the assay and indicate that the assay can be applied to identify inhibitors of these interactions.

Example 4

Detection of Context-Dependent Dimerization of a Transmembrane Protein

To support the ability of the method to detect protein-protein interactions under physiological conditions, we studied dimerization of ERN1. ERN1 is a single-span transmembrane protein involved in the cellular response to ER-stress. The ERN1 protein is able to sense unfolded proteins in the ER through its N-terminal domain which is exposed to the ER lumen. This leads to its dimerization and activation of the kinase and endoribonuclease enzymatic domains in its C-terminal moiety exposed towards the cytoplasm. To mimic ER-stress, tunicamycin was applied to the cells, an inhibitor of protein glycosylation which is generally used to induce ER-stress.

Figure 6A:
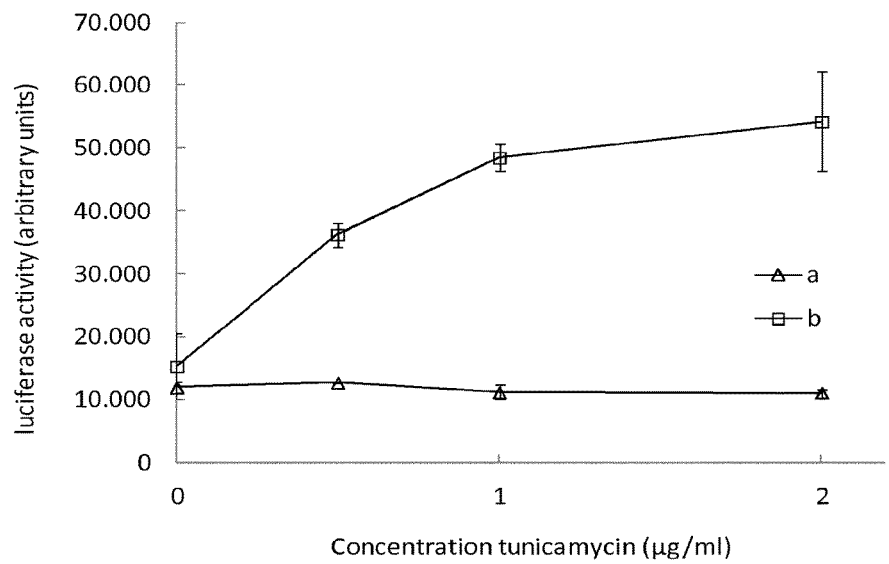
Figure 6B:
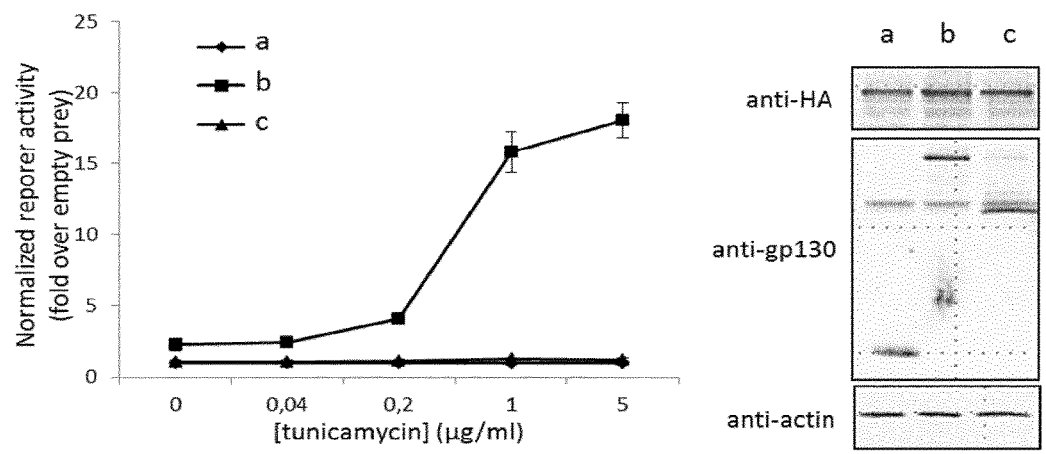
Figure 6C:
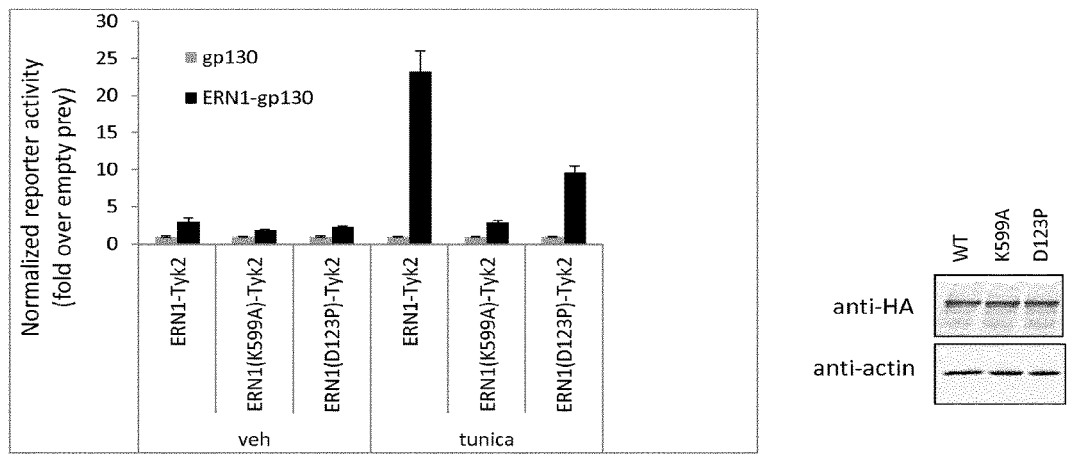
Figure 6D:
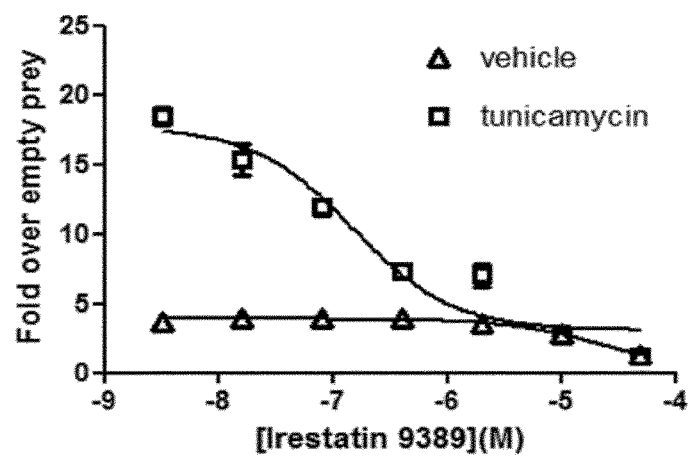

In a first experiment, cells were transfected with the following combinations of plasmids (500 ng of the kinase fusion construct, 100 ng of the gp130 fusion construct and 50 ng of the luciferase reporter construct) according to the methods described above:
 a) pcDNA5/FRT/TO-ERN1-Tyk2(C)-HA+pMG1+pXP2d2-rPAPI-luciferase
 b) pcDNA5/FRT/TO-ERN1-Tyk2(C)-HA+pMG2C-ERN1+pXP2d2-rPAPI-luciferase After transfection, cells were treated with 0-0.5-1-2 µg/ml tunicamycin, final concentration. The results shown in FIG. 6A show a dose-dependent signal upon addition of tunicamycin, only in cells expressing both ERN1-Tyk2(C) and ERN1-gp130 fusion constructs (transfection b). No signal was observed when the ERN1-Tyk2(C) fusion construct was combined with an unfused gp130 fragment (transfection a).

In a second experiment (FIG. 6B), cells were transfected with the following combinations of plasmids (62.5 ng of the kinase fusion construct, 125 ng of the gp130 fusion construct and 50 ng of the luciferase reporter construct) according to the methods described herein:
 a) pcDNA5/FRT/TO-ERN1-Tyk2(C)-HA+pMG1+pXP2d2-rPAPI-luciferase
 b) pcDNA5/FRT/TO-ERN1-Tyk2(C)-HA+pMG2C-ERN1+pXP2d2-rPAPI-luciferase
 c) pcDNA5/FRT/TO-ERN1-Tyk2(C)-HA+pMG2C-ERN1cyt+pXP2d2-rPAPI-luciferase After transfection, cells were treated with 0-0.04-0.2-1-5 µg/ml tunicamycin, final concentration. The luciferase data are presented as fold induction relative to the signal obtained in cells transfected with unfused gp130 (empty prey; transfection a) and treated with the same concentration tunicamycin. Expression of the different fusion proteins was confirmed using Western blot. These data show that in accordance with the requirement of the ERN1 lumenal domain to sense ER stress, no signal is produced upon overexpression of full length ERN1 kinase fusion and a gp130 fusion containing only the cytoplasmic portion of ERN1 (transfection c).

In a next experiment (FIG. 6C), cells were transfected with combinations of the pXP2d2-rPAPI-luciferase construct (50 ng), a WT or mutant ERN1 kinase fusion construct (62.5 ng) and either unfused or ERN1-fused gp130 construct (125 ng). After transfection, cells were either vehicle (DMSO) treated or treated with 1 µg/ml tunicamycin (final concentration). The mutant ERN1 kinase fusions have mutations in either the luminal domain (D123P) or cytoplasmic ATP-binding pocket (K599A). Both mutations are expected to block ERN1 oligomerization. As evident from FIG. 6C we indeed find that both mutations block the interaction with full length ERN1 gp130 fusion, despite equal expression and similar (aspecific) interaction signals with unfused gp130 constructs.

In another experiment (FIG. 6D), cells were transfected with combinations of the pXP2d2-rPAPI-luciferase construct (50 ng), the ERN1 kinase fusion construct (62.5 ng) and either unfused or ERN1-fused gp130 construct (125 ng). After transfection, cells were treated with tunicamycin (1 µg/ml tunicamycin final concentration) or vehicle (DMSO) combined with increasing doses of Irestatin 9389. This molecule was recently reported to inhibit ERN1 endonuclease activity (Feldman and Koong, 2007). Although the molecular mode of action of Irestatin 9389 was not reported, the molecule induced a dose-dependent disruption of ERN1 dimerization in the assay described herein.

Together, these data indicate that the method is able to specifically detect the ER-stress-induced dimerization of the ERN1 protein and to analyze the structure-function relationship of this protein and pharmacological interference with dimerization of the protein in more detail.

Example 5

Detection of Heterologous Interactions Among Transmembrane Proteins

To further corroborate the ability of the assay to analyze protein-protein interactions involving integral membrane proteins, heterologous interactions between transmembrane proteins were analyzed. Serotonin transporter (SERT) is a multispan integral membrane protein that transports serotonin from the synaptic spaces into presynaptic neurons, this way terminating the action of serotonin and recycling it. In this example, we show its interaction with the synaptobrevins VAMP 1 and VAMP2, which are transmembrane proteins involved in fusion of synaptic vesicles with the pre-synaptic membrane.

Cells were transfected with combinations of the pXP2d2-rPAPI-luciferase construct (50 ng), a SERT or RTp66 kinase fusion construct (1000 ng) and either unfused (pMG2) or one of the indicated gp130 fusion constructs (pMG2-RTp51, pMG1-VAMP1 or pMG2-VAMP2; 500 ng). Luciferase activity is shown as fold induction relative to the luciferase signal obtained in cells transfected with unfused gp130 (pMG2).

The results (FIG. 7) show a clear signal when VAMP1 and VAMP2 gp130 fusion constructs were transfected in combination with the SERT kinase fusion construct, and not when combined with the HIV-1 RTp66 (reverse transcriptase subunit p66) fusion construct. The strong signal obtained for the co-transfection of the RTp66 kinase and the RTp51 gp130 fusion constructs, which has been previously described (WO2012117031), is included as a control for proper expression and functioning of the RTp66 kinase fusion.

REFERENCES

Eyckennan, S., Verhee, A., Van der Heyden, J., Lemmens, I., Van Ostade, X., Vandekerckhove, J., and Tavernier, J. (2001). Design and application of a cytokine-receptor-based interaction trap. Nature Cell Biology 3, 1114-1119.

Feldman, D., and Koong, A. (2007). Irestatin, a potent inhibitor of ERN1α and the unfolded protein response, is a hypoxia-selective cytotoxin and impairs tumor growth. J Clin Oncol 25, 3514.

Kakuta, H., Sudoh, K., Sasamata, M., and Yamagishi, S. (2005). Telmisartan has the strongest binding affinity to angiotensin II type 1 receptor: comparison with other angiotensin II type 1 receptor blockers. Int J Clin Pharmacol Res 25, 41-46.

Lamesch, P., Li, N., Milstein, S., Fan, C., Hao, T., Szabo, G., Hu, Z., Venkatesan, K., Bethel, G., Martin, P., et al., (2007). hORFeome v3.1: a resource of human open reading frames representing over 10,000 human genes. Genomics 89, 307-315.

Lemmens, I., Eyckerman, S., Zabeau, L., Catteeuw, D., Vertenten, E., Verschueren, K., Huylebroeck, D., Vandekerckhove, J., and Tavernier, J. (2003). Heteromeric MAPPIT: a novel strategy to study modification-dependent protein-protein interactions in mammalian cells. Nucleic Acids Research 31.

Lievens, S., Vanderroost, N., Van der Heyden, J., Gesellchen, V., Vidal, M., and Tavernier, J. (2009). Array MAPPIT: high-throughput interactome analysis in mammalian cells. J Proteome Res 8, 877-886.

Pattyn, E., Lavens, D., Van der Heyden, J., verhee, A., Lievens, S., Lemmens, I., Hallenberger, S., Jochmans, D and Tavernier, J. (2008). MAPPIT (Mammalian Protein-Protein Interaction Trap) as a tool to study HIV reverse transcriptase dimerization in intact human cells. J. Virol. Methods 153, 7-15.

Takebe, Y., Seiki, M., Fujisawa, J., Hoy, P., Yokota, K., Arai, K., Yoshida, M., and Arai, N. (1988). SR alpha promoter: an efficient and versatile mammalian cDNA expression system composed of the simian virus 40 early promoter and the R-U5 segment of human T-cell leukemia virus type 1 long terminal repeat. Mol Cell Biol 8, 466-472.

The invention claimed is:

1. A recombinant protein complex comprising:
a first fusion protein consisting of a membrane spanning domain fused to a tyrosine kinase domain, wherein the tyrosine kinase domain has at least 95% sequence identity to amino acids 589-1187 of SEQ ID NO: 1, and
a second fusion protein consisting of an interaction domain fused to a reporter phosphorylation domain, wherein the phosphorylation domain has the amino acid sequence of SEQ ID NO: 2, and
wherein the tyrosine kinase domain can phosphorylate the tyrosine of the reporter phosphorylation domain upon the formation of a recombinant protein complex via an interaction between the membrane spanning domain and the interaction domain.

2. The recombinant protein complex of claim 1, wherein the tyrosine kinase domain is a mutant kinase domain.

3. The recombinant protein complex of claim 2, wherein said mutant kinase domain is a constitutive mutant kinase domain.

4. The recombinant protein complex of claim 1, wherein the tyrosine kinase domain is a TYK2 tyrosine kinase domain or a constitutive TYK2 tyrosine kinase domain mutant.

5. The recombinant protein complex of claim 1, wherein the tyrosine kinase domain is a Jak kinase tyrosine kinase domain.

6. The recombinant protein complex of claim 1, wherein the domain fused to the membrane spanning domain of the first fusion protein is fused to the carboxyterminal end of the membrane spanning domain.

7. The recombinant protein complex of claim 1, wherein the membrane spanning domain is a multispan membrane spanning domain.

8. The recombinant protein complex of claim 7, wherein said multispan membrane spanning domain is a G protein coupled receptor.

9. The recombinant protein complex of claim 1, wherein the tyrosine kinase domain is the Tyk2 domain comprised in SEQ ID NO: 3, SEQ ID NO: 4, SEQ ID NO:5 or SEQ ID NO:29.

10. The recombinant protein complex of claim 2, wherein the mutant kinase domain is an inactive mutant kinase domain that can be activated by the addition of an exogenous small molecule.

* * * * *

UNITED STATES PATENT AND TRADEMARK OFFICE
CERTIFICATE OF CORRECTION

PATENT NO. : 10,336,811 B2
APPLICATION NO. : 14/381502
DATED : July 2, 2019
INVENTOR(S) : Jan Tavernier and Samuel Lievens Page 1 of 1

It is certified that error appears in the above-identified patent and that said Letters Patent is hereby corrected as shown below:

In the Specification

In Column 4, Line 17, please replace "endoplasmatic" with --endoplasmic--

In Column 10, Line 31, please replace "arbitry" with --arbitrary--

In Column 10, Line 57, please replace "endoplasmatic" with --endoplasmic--

In Column 13, Line 11, please replace "en" with --and--

In Column 20, Line 35, please replace "aspecific" with --non-specific--

In Column 21, Line 25, please replace "Eyckennan" with --Eyckerman--

Signed and Sealed this
Twenty-seventh Day of August, 2019

Andrei Iancu
*Director of the United States Patent and Trademark Office*

SEQUENCE LISTING

```
<160> NUMBER OF SEQ ID NOS: 37

<210> SEQ ID NO 1
<211> LENGTH: 1187
<212> TYPE: PRT
<213> ORGANISM: Homo sapiens

<400> SEQUENCE: 1

Met Pro Leu Arg His Trp Gly Met Ala Arg Gly Ser Lys Pro Val Gly
1               5                   10                  15

Asp Gly Ala Gln Pro Met Ala Ala Met Gly Gly Leu Lys Val Leu Leu
            20                  25                  30

His Trp Ala Gly Pro Gly Gly Gly Glu Pro Trp Val Thr Phe Ser Glu
        35                  40                  45

Ser Ser Leu Thr Ala Glu Glu Val Cys Ile His Ile Ala His Lys Val
    50                  55                  60

Gly Ile Thr Pro Pro Cys Phe Asn Leu Phe Ala Leu Phe Asp Ala Gln
65                  70                  75                  80

Ala Gln Val Trp Leu Pro Pro Asn His Ile Leu Glu Ile Pro Arg Asp
                85                  90                  95

Ala Ser Leu Met Leu Tyr Phe Arg Ile Arg Phe Tyr Phe Arg Asn Trp
            100                 105                 110

His Gly Met Asn Pro Arg Glu Pro Ala Val Tyr Arg Cys Gly Pro Pro
        115                 120                 125

Gly Thr Glu Ala Ser Ser Asp Gln Thr Ala Gln Gly Met Gln Leu Leu
    130                 135                 140

Asp Pro Ala Ser Phe Glu Tyr Leu Phe Glu Gln Gly Lys His Glu Phe
```

```
              145                 150                 155                 160
Val Asn Asp Val Ala Ser Leu Trp Glu Leu Ser Thr Glu Glu Ile
                    165                 170                 175
His His Phe Lys Asn Glu Ser Leu Gly Met Ala Phe Leu His Leu Cys
                    180                 185                 190
His Leu Ala Leu Arg His Gly Ile Pro Leu Glu Glu Val Ala Lys Lys
                    195                 200                 205
Thr Ser Phe Lys Asp Cys Ile Pro Arg Ser Phe Arg Arg His Ile Arg
    210                 215                 220
Gln His Ser Ala Leu Thr Arg Leu Arg Leu Arg Asn Val Phe Arg Arg
225                 230                 235                 240
Phe Leu Arg Asp Phe Gln Pro Gly Arg Leu Ser Gln Gln Met Val Met
                    245                 250                 255
Val Lys Tyr Leu Ala Thr Leu Glu Arg Leu Ala Pro Arg Phe Gly Thr
                    260                 265                 270
Glu Arg Val Pro Val Cys His Leu Arg Leu Leu Ala Gln Ala Glu Gly
                    275                 280                 285
Glu Pro Cys Tyr Ile Arg Asp Ser Gly Val Ala Pro Thr Asp Pro Gly
    290                 295                 300
Pro Glu Ser Ala Ala Gly Pro Pro Thr His Glu Val Leu Val Thr Gly
305                 310                 315                 320
Thr Gly Gly Ile Gln Trp Trp Pro Val Glu Glu Val Asn Lys Glu
                    325                 330                 335
Glu Gly Ser Ser Gly Ser Ser Gly Arg Asn Pro Gln Ala Ser Leu Phe
                    340                 345                 350
Gly Lys Lys Ala Lys Ala His Lys Ala Val Gly Gln Pro Ala Asp Arg
                    355                 360                 365
Pro Arg Glu Pro Leu Trp Ala Tyr Phe Cys Asp Phe Arg Asp Ile Thr
                    370                 375                 380
His Val Val Leu Lys Glu His Cys Val Ser Ile His Arg Gln Asp Asn
385                 390                 395                 400
Lys Cys Leu Glu Leu Ser Leu Pro Ser Arg Ala Ala Leu Ser Phe
                    405                 410                 415
Val Ser Leu Val Asp Gly Tyr Phe Arg Leu Thr Ala Asp Ser Ser His
                    420                 425                 430
Tyr Leu Cys His Glu Val Ala Pro Pro Arg Leu Val Met Ser Ile Arg
                    435                 440                 445
Asp Gly Ile His Gly Pro Leu Leu Glu Pro Phe Val Gln Ala Lys Leu
    450                 455                 460
Arg Pro Glu Asp Gly Leu Tyr Leu Ile His Trp Ser Thr Ser His Pro
465                 470                 475                 480
Tyr Arg Leu Ile Leu Thr Val Ala Gln Arg Ser Gln Ala Pro Asp Gly
                    485                 490                 495
Met Gln Ser Leu Arg Leu Arg Lys Phe Pro Ile Glu Gln Gln Asp Gly
                    500                 505                 510
Ala Phe Val Leu Glu Gly Trp Gly Arg Ser Phe Pro Ser Val Arg Glu
                    515                 520                 525
Leu Gly Ala Ala Leu Gln Gly Cys Leu Leu Arg Ala Gly Asp Asp Cys
                    530                 535                 540
Phe Ser Leu Arg Arg Cys Cys Leu Pro Gln Pro Gly Glu Thr Ser Asn
545                 550                 555                 560
Leu Ile Ile Met Arg Gly Ala Arg Ala Ser Pro Arg Thr Leu Asn Leu
                    565                 570                 575
```

```
Ser Gln Leu Ser Phe His Arg Val Asp Gln Lys Glu Ile Thr Gln Leu
            580                 585                 590

Ser His Leu Gly Gln Gly Thr Arg Thr Asn Val Tyr Glu Gly Arg Leu
            595                 600                 605

Arg Val Glu Gly Ser Gly Asp Pro Glu Gly Lys Met Asp Asp Glu
610                 615                 620

Asp Pro Leu Val Pro Gly Arg Asp Arg Gly Gln Glu Leu Arg Val Val
625                 630                 635                 640

Leu Lys Val Leu Asp Pro Ser His His Asp Ile Ala Leu Ala Phe Tyr
                645                 650                 655

Glu Thr Ala Ser Leu Met Ser Gln Val Ser His Thr His Leu Ala Phe
            660                 665                 670

Val His Gly Val Cys Val Arg Gly Pro Glu Asn Ile Met Val Thr Glu
            675                 680                 685

Tyr Val Glu His Gly Pro Leu Asp Val Trp Leu Arg Arg Glu Arg Gly
690                 695                 700

His Val Pro Met Ala Trp Lys Met Val Val Ala Gln Gln Leu Ala Ser
705                 710                 715                 720

Ala Leu Ser Tyr Leu Glu Asn Lys Asn Leu Val His Gly Asn Val Cys
                725                 730                 735

Gly Arg Asn Ile Leu Leu Ala Arg Leu Gly Leu Ala Glu Gly Thr Ser
            740                 745                 750

Pro Phe Ile Lys Leu Ser Asp Pro Gly Val Gly Leu Gly Ala Leu Ser
            755                 760                 765

Arg Glu Glu Arg Val Glu Arg Ile Pro Trp Leu Ala Pro Glu Cys Leu
770                 775                 780

Pro Gly Gly Ala Asn Ser Leu Ser Thr Ala Met Asp Lys Trp Gly Phe
785                 790                 795                 800

Gly Ala Thr Leu Leu Glu Ile Cys Phe Asp Gly Glu Ala Pro Leu Gln
                805                 810                 815

Ser Arg Ser Pro Ser Glu Lys Glu His Phe Tyr Gln Arg Gln His Arg
            820                 825                 830

Leu Pro Glu Pro Ser Cys Pro Gln Leu Ala Thr Leu Thr Ser Gln Cys
            835                 840                 845

Leu Thr Tyr Glu Pro Thr Gln Arg Pro Ser Phe Arg Thr Ile Leu Arg
850                 855                 860

Asp Leu Thr Arg Leu Gln Pro His Asn Leu Ala Asp Val Leu Thr Val
865                 870                 875                 880

Asn Pro Asp Ser Pro Ala Ser Asp Pro Thr Val Phe His Lys Arg Tyr
                885                 890                 895

Leu Lys Lys Ile Arg Asp Leu Gly Glu Gly His Phe Gly Lys Val Ser
            900                 905                 910

Leu Tyr Cys Tyr Asp Pro Thr Asn Asp Gly Thr Gly Glu Met Val Ala
            915                 920                 925

Val Lys Ala Leu Lys Ala Asp Cys Gly Pro Gln His Arg Ser Gly Trp
930                 935                 940

Lys Gln Glu Ile Asp Ile Leu Arg Thr Leu Tyr His Glu His Ile Ile
945                 950                 955                 960

Lys Tyr Lys Gly Cys Cys Glu Asp Gln Gly Glu Lys Ser Leu Gln Leu
                965                 970                 975

Val Met Glu Tyr Val Pro Leu Gly Ser Leu Arg Asp Tyr Leu Pro Arg
            980                 985                 990
```

His Ser Ile Gly Leu Ala Gln Leu Leu Phe Ala Gln Gln Ile Cys
        995                 1000                1005

Glu Gly Met Ala Tyr Leu His Ala Gln His Tyr Ile His Arg Asp
    1010                1015                1020

Leu Ala Ala Arg Asn Val Leu Leu Asp Asn Asp Arg Leu Val Lys
    1025                1030                1035

Ile Gly Asp Phe Gly Leu Ala Lys Ala Val Pro Glu Gly His Glu
    1040                1045                1050

Tyr Tyr Arg Val Arg Glu Asp Gly Asp Ser Pro Val Phe Trp Tyr
    1055                1060                1065

Ala Pro Glu Cys Leu Lys Glu Tyr Lys Phe Tyr Tyr Ala Ser Asp
    1070                1075                1080

Val Trp Ser Phe Gly Val Thr Leu Tyr Glu Leu Leu Thr His Cys
    1085                1090                1095

Asp Ser Ser Gln Ser Pro Pro Thr Lys Phe Leu Glu Leu Ile Gly
    1100                1105                1110

Ile Ala Gln Gly Gln Met Thr Val Leu Arg Leu Thr Glu Leu Leu
    1115                1120                1125

Glu Arg Gly Glu Arg Leu Pro Arg Pro Asp Lys Cys Pro Cys Glu
    1130                1135                1140

Val Tyr His Leu Met Lys Asn Cys Trp Glu Thr Glu Ala Ser Phe
    1145                1150                1155

Arg Pro Thr Phe Glu Asn Leu Ile Pro Ile Leu Lys Thr Val His
    1160                1165                1170

Glu Lys Tyr Gln Gly Gln Ala Pro Ser Val Phe Ser Val Cys
    1175                1180                1185

<210> SEQ ID NO 2
<211> LENGTH: 158
<212> TYPE: PRT
<213> ORGANISM: Homo sapiens

<400> SEQUENCE: 2

Thr Val Val His Ser Gly Tyr Arg His Gln Val Pro Ser Val Gln Val
1               5                   10                  15

Phe Ser Arg Ser Glu Ser Thr Gln Pro Leu Leu Asp Ser Glu Glu Arg
                20                  25                  30

Pro Glu Asp Leu Gln Leu Val Asp His Val Asp Gly Gly Asp Gly Ile
            35                  40                  45

Leu Pro Arg Gln Gln Tyr Phe Lys Gln Asn Cys Ser Gln His Glu Ser
        50                  55                  60

Ser Pro Asp Ile Ser His Phe Glu Arg Ser Lys Gln Val Ser Ser Val
65                  70                  75                  80

Asn Glu Glu Asp Phe Val Arg Leu Lys Gln Gln Ile Ser Asp His Ile
                85                  90                  95

Ser Gln Ser Cys Gly Ser Gly Gln Met Lys Met Phe Gln Glu Val Ser
                100                 105                 110

Ala Ala Asp Ala Phe Gly Pro Gly Thr Glu Gly Gln Val Glu Arg Phe
            115                 120                 125

Glu Thr Val Gly Met Glu Ala Ala Thr Asp Glu Gly Met Pro Lys Ser
        130                 135                 140

Tyr Leu Pro Gln Thr Val Arg Gln Gly Gly Tyr Met Pro Gln
145                 150                 155

<210> SEQ ID NO 3

<211> LENGTH: 985
<212> TYPE: PRT
<213> ORGANISM: Artificial Sequence
<220> FEATURE:
<223> OTHER INFORMATION: SSTR2-Tyk2(C) fusion construct

<400> SEQUENCE: 3

```
Met Asp Met Ala Asp Glu Pro Leu Asn Gly Ser His Thr Trp Leu Ser
1               5                   10                  15

Ile Pro Phe Asp Leu Asn Gly Ser Val Val Ser Thr Asn Thr Ser Asn
            20                  25                  30

Gln Thr Glu Pro Tyr Tyr Asp Leu Thr Ser Asn Ala Val Leu Thr Phe
        35                  40                  45

Ile Tyr Phe Val Val Cys Ile Ile Gly Leu Cys Gly Asn Thr Leu Val
50                  55                  60

Ile Tyr Val Ile Leu Arg Tyr Ala Lys Met Lys Thr Ile Thr Asn Ile
65                  70                  75                  80

Tyr Ile Leu Asn Leu Ala Ile Ala Asp Glu Leu Phe Met Leu Gly Leu
                85                  90                  95

Pro Phe Leu Ala Met Gln Val Ala Leu Val His Trp Pro Phe Gly Lys
            100                 105                 110

Ala Ile Cys Arg Val Val Met Thr Val Asp Gly Ile Asn Gln Phe Thr
        115                 120                 125

Ser Ile Phe Cys Leu Thr Val Met Ser Ile Asp Arg Tyr Leu Ala Val
130                 135                 140

Val His Pro Ile Lys Ser Ala Lys Trp Arg Arg Pro Arg Thr Ala Lys
145                 150                 155                 160

Met Ile Thr Met Ala Val Trp Gly Val Ser Leu Leu Val Ile Leu Pro
                165                 170                 175

Ile Met Ile Tyr Ala Gly Leu Arg Ser Asn Gln Trp Gly Arg Ser Ser
            180                 185                 190

Cys Thr Ile Asn Trp Pro Gly Glu Ser Gly Ala Trp Tyr Thr Gly Phe
        195                 200                 205

Ile Ile Tyr Thr Phe Ile Leu Gly Phe Leu Val Pro Leu Thr Ile Ile
210                 215                 220

Cys Leu Cys Tyr Leu Phe Ile Ile Lys Val Lys Ser Ser Gly Ile
225                 230                 235                 240

Arg Val Gly Ser Ser Lys Arg Lys Lys Ser Glu Lys Lys Val Thr Arg
                245                 250                 255

Met Val Ser Ile Val Val Ala Val Phe Ile Phe Cys Trp Leu Pro Phe
            260                 265                 270

Tyr Ile Phe Asn Val Ser Ser Val Ser Met Ala Ile Ser Pro Thr Pro
        275                 280                 285

Ala Leu Lys Gly Met Phe Asp Phe Val Val Val Leu Thr Tyr Ala Asn
290                 295                 300

Ser Cys Ala Asn Pro Ile Leu Tyr Ala Phe Leu Ser Asp Asn Phe Lys
305                 310                 315                 320

Lys Ser Phe Gln Asn Val Leu Cys Leu Val Lys Val Ser Gly Thr Asp
                325                 330                 335

Asp Gly Glu Arg Ser Asp Ser Lys Gln Asp Lys Ser Arg Leu Asn Glu
            340                 345                 350

Thr Thr Glu Thr Gln Arg Thr Leu Leu Asn Gly Asp Leu Gln Thr Ser
        355                 360                 365

Ile Ala Ala Ala Gly Gly Ser Ile Thr Gln Leu Ser His Leu Gly Gln
370                 375                 380
```

```
Gly Thr Arg Thr Asn Val Tyr Glu Gly Arg Leu Arg Val Glu Gly Ser
385                 390                 395                 400

Gly Asp Pro Glu Glu Gly Lys Met Asp Asp Glu Asp Pro Leu Val Pro
            405                 410                 415

Gly Arg Asp Arg Gly Gln Glu Leu Arg Val Val Leu Lys Val Leu Asp
            420                 425                 430

Pro Ser His His Asp Ile Ala Leu Ala Phe Tyr Glu Thr Ala Ser Leu
            435                 440                 445

Met Ser Gln Val Ser His Thr His Leu Ala Phe Val His Gly Val Cys
            450                 455                 460

Val Arg Gly Pro Glu Asn Ser Met Val Thr Glu Tyr Val Glu His Gly
465                 470                 475                 480

Pro Leu Asp Val Trp Leu Arg Arg Glu Arg Gly His Val Pro Met Ala
                485                 490                 495

Trp Lys Met Val Val Ala Gln Leu Ala Ser Ala Leu Ser Tyr Leu
                500                 505                 510

Glu Asn Lys Asn Leu Val His Gly Asn Val Cys Gly Arg Asn Ile Leu
            515                 520                 525

Leu Ala Arg Leu Gly Leu Ala Glu Gly Thr Ser Pro Phe Ile Lys Leu
530                 535                 540

Ser Asp Pro Gly Val Gly Leu Gly Ala Leu Ser Arg Glu Glu Arg Val
545                 550                 555                 560

Glu Arg Ile Pro Trp Leu Ala Pro Glu Cys Leu Pro Gly Gly Ala Asn
                565                 570                 575

Ser Leu Ser Thr Ala Met Asp Lys Trp Gly Phe Gly Ala Thr Leu Leu
            580                 585                 590

Glu Ile Cys Phe Asp Gly Glu Ala Pro Leu Gln Ser Arg Ser Pro Ser
            595                 600                 605

Glu Lys Glu His Phe Tyr Gln Arg Gln His Arg Leu Pro Glu Pro Ser
            610                 615                 620

Cys Pro Gln Leu Ala Thr Leu Thr Ser Gln Cys Leu Thr Tyr Glu Pro
625                 630                 635                 640

Thr Gln Arg Pro Ser Phe Arg Thr Ile Leu Arg Asp Leu Thr Arg Val
                645                 650                 655

Gln Pro His Asn Leu Ala Asp Val Leu Thr Val Asn Arg Asp Ser Pro
            660                 665                 670

Ala Val Gly Pro Thr Thr Phe His Lys Arg Tyr Leu Lys Lys Ile Arg
            675                 680                 685

Asp Leu Gly Glu Gly His Phe Gly Lys Val Ser Leu Tyr Cys Tyr Asp
            690                 695                 700

Pro Thr Asn Asp Gly Thr Gly Glu Met Val Ala Val Lys Ala Leu Lys
705                 710                 715                 720

Ala Asp Cys Gly Pro Gln His Arg Ser Gly Trp Lys Gln Glu Ile Asp
            725                 730                 735

Ile Leu Arg Thr Leu Tyr His Glu His Ile Ile Lys Tyr Lys Gly Cys
            740                 745                 750

Cys Glu Asp Gln Gly Glu Lys Ser Leu Gln Leu Val Met Glu Tyr Val
            755                 760                 765

Pro Leu Gly Ser Leu Arg Asp Tyr Leu Pro Arg His Ser Ile Gly Leu
            770                 775                 780

Ala Gln Leu Leu Leu Phe Ala Gln Gln Ile Cys Glu Gly Met Ala Tyr
785                 790                 795                 800
```

Leu His Ala His Asp Tyr Ile His Arg Asp Leu Ala Ala Arg Asn Val
            805                 810                 815

Leu Leu Asp Asn Asp Arg Leu Val Lys Ile Gly Asp Phe Gly Leu Ala
            820                 825                 830

Lys Ala Val Pro Glu Gly His Glu Tyr Tyr Arg Val Arg Glu Asp Gly
            835                 840                 845

Asp Ser Pro Val Phe Trp Tyr Ala Pro Glu Cys Leu Lys Glu Tyr Lys
    850                 855                 860

Phe Tyr Tyr Ala Ser Asp Val Trp Ser Phe Gly Val Thr Leu Tyr Glu
865                 870                 875                 880

Leu Leu Thr His Cys Asp Ser Ser Gln Ser Pro Pro Thr Lys Phe Leu
            885                 890                 895

Glu Leu Ile Gly Ile Ala Gln Gly Gln Met Thr Val Leu Arg Leu Thr
            900                 905                 910

Glu Leu Leu Glu Arg Gly Glu Arg Leu Pro Arg Pro Asp Lys Cys Pro
            915                 920                 925

Cys Glu Val Tyr His Leu Met Lys Asn Cys Trp Glu Thr Glu Ala Ser
    930                 935                 940

Phe Arg Pro Thr Phe Glu Asn Leu Ile Pro Ile Leu Lys Thr Val His
945                 950                 955                 960

Glu Lys Tyr Gln Gly Gln Ala Pro Ser Val Phe Ser Val Cys Leu Glu
            965                 970                 975

Tyr Pro Tyr Asp Val Pro Asp Tyr Ala
            980                 985

<210> SEQ ID NO 4
<211> LENGTH: 975
<212> TYPE: PRT
<213> ORGANISM: Artificial Sequence
<220> FEATURE:
<223> OTHER INFORMATION: AGTR1-Tyk2(C) fusion construct

<400> SEQUENCE: 4

Met Ile Leu Asn Ser Ser Thr Glu Asp Gly Ile Lys Arg Ile Gln Asp
1               5                   10                  15

Asp Cys Pro Lys Ala Gly Arg His Asn Tyr Ile Phe Val Met Ile Pro
            20                  25                  30

Thr Leu Tyr Ser Ile Ile Phe Val Val Gly Ile Phe Gly Asn Ser Leu
        35                  40                  45

Val Val Ile Val Ile Tyr Phe Tyr Met Lys Leu Lys Thr Val Ala Ser
    50                  55                  60

Val Phe Leu Leu Asn Leu Ala Leu Ala Asp Leu Cys Phe Leu Leu Thr
65                  70                  75                  80

Leu Pro Leu Trp Ala Val Tyr Thr Ala Met Glu Tyr Arg Trp Pro Phe
            85                  90                  95

Gly Asn Tyr Leu Cys Lys Ile Ala Ser Ala Ser Val Ser Phe Asn Leu
            100                 105                 110

Tyr Ala Ser Val Phe Leu Leu Thr Cys Leu Ser Ile Asp Arg Tyr Leu
        115                 120                 125

Ala Ile Val His Pro Met Lys Ser Arg Leu Arg Arg Thr Met Leu Val
    130                 135                 140

Ala Lys Val Thr Cys Ile Ile Ile Trp Leu Leu Ala Gly Leu Ala Ser
145                 150                 155                 160

Leu Pro Ala Ile Ile His Arg Asn Val Phe Phe Ile Glu Asn Thr Asn
            165                 170                 175

```
Ile Thr Val Cys Ala Phe His Tyr Glu Ser Gln Asn Ser Thr Leu Pro
            180                 185                 190

Ile Gly Leu Gly Leu Thr Lys Asn Ile Leu Gly Phe Leu Phe Pro Phe
        195                 200                 205

Leu Ile Ile Leu Thr Ser Tyr Thr Leu Ile Trp Lys Ala Leu Lys Lys
    210                 215                 220

Ala Tyr Glu Ile Gln Lys Asn Lys Pro Arg Asn Asp Ile Phe Lys
225                 230                 235                 240

Ile Ile Met Ala Ile Val Leu Phe Phe Phe Ser Trp Ile Pro His
                245                 250                 255

Gln Ile Phe Thr Phe Leu Asp Val Leu Ile Gln Leu Gly Ile Ile Arg
        260                 265                 270

Asp Cys Arg Ile Ala Asp Ile Val Asp Thr Ala Met Pro Ile Thr Ile
        275                 280                 285

Cys Ile Ala Tyr Phe Asn Asn Cys Leu Asn Pro Leu Phe Tyr Gly Phe
    290                 295                 300

Leu Gly Lys Lys Phe Lys Arg Tyr Phe Leu Gln Leu Leu Lys Tyr Ile
305                 310                 315                 320

Pro Pro Lys Ala Lys Ser His Ser Asn Leu Ser Thr Lys Met Ser Thr
                325                 330                 335

Leu Ser Tyr Arg Pro Ser Asp Asn Val Ser Ser Ser Thr Lys Lys Pro
        340                 345                 350

Ala Pro Cys Phe Glu Val Glu Ala Ala Gly Ser Ile Thr Gln
        355                 360                 365

Leu Ser His Leu Gly Gln Gly Thr Arg Thr Asn Val Tyr Glu Gly Arg
    370                 375                 380

Leu Arg Val Glu Gly Ser Gly Asp Pro Glu Glu Gly Lys Met Asp Asp
385                 390                 395                 400

Glu Asp Pro Leu Val Pro Gly Arg Asp Arg Gly Gln Glu Leu Arg Val
                405                 410                 415

Val Leu Lys Val Leu Asp Pro Ser His His Asp Ile Ala Leu Ala Phe
        420                 425                 430

Tyr Glu Thr Ala Ser Leu Met Ser Gln Val Ser His Thr His Leu Ala
    435                 440                 445

Phe Val His Gly Val Cys Val Arg Gly Pro Glu Asn Ser Met Val Thr
    450                 455                 460

Glu Tyr Val Glu His Gly Pro Leu Asp Val Trp Leu Arg Arg Glu Arg
465                 470                 475                 480

Gly His Val Pro Met Ala Trp Lys Met Val Val Ala Gln Gln Leu Ala
                485                 490                 495

Ser Ala Leu Ser Tyr Leu Glu Asn Lys Asn Leu Val His Gly Asn Val
        500                 505                 510

Cys Gly Arg Asn Ile Leu Leu Ala Arg Leu Gly Leu Ala Glu Gly Thr
    515                 520                 525

Ser Pro Phe Ile Lys Leu Ser Asp Pro Gly Val Gly Leu Gly Ala Leu
    530                 535                 540

Ser Arg Glu Glu Arg Val Glu Arg Ile Pro Trp Leu Ala Pro Glu Cys
545                 550                 555                 560

Leu Pro Gly Gly Ala Asn Ser Leu Ser Thr Ala Met Asp Lys Trp Gly
                565                 570                 575

Phe Gly Ala Thr Leu Leu Glu Ile Cys Phe Asp Gly Glu Ala Pro Leu
        580                 585                 590

Gln Ser Arg Ser Pro Ser Glu Lys Glu His Phe Tyr Gln Arg Gln His
```

```
                595             600             605
Arg Leu Pro Glu Pro Ser Cys Pro Gln Leu Ala Thr Leu Thr Ser Gln
610             615             620

Cys Leu Thr Tyr Glu Pro Thr Gln Arg Pro Ser Phe Arg Thr Ile Leu
625             630             635             640

Arg Asp Leu Thr Arg Val Gln Pro His Asn Leu Ala Asp Val Leu Thr
            645             650             655

Val Asn Arg Asp Ser Pro Ala Val Gly Pro Thr Thr Phe His Lys Arg
            660             665             670

Tyr Leu Lys Lys Ile Arg Asp Leu Gly Glu Gly His Phe Gly Lys Val
            675             680             685

Ser Leu Tyr Cys Tyr Asp Pro Thr Asn Asp Gly Thr Gly Glu Met Val
            690             695             700

Ala Val Lys Ala Leu Lys Ala Asp Cys Gly Pro Gln His Arg Ser Gly
705             710             715             720

Trp Lys Gln Glu Ile Asp Ile Leu Arg Thr Leu Tyr His Glu His Ile
            725             730             735

Ile Lys Tyr Lys Gly Cys Cys Glu Asp Gln Gly Glu Lys Ser Leu Gln
            740             745             750

Leu Val Met Glu Tyr Val Pro Leu Gly Ser Leu Arg Asp Tyr Leu Pro
            755             760             765

Arg His Ser Ile Gly Leu Ala Gln Leu Leu Phe Ala Gln Gln Ile
770             775             780

Cys Glu Gly Met Ala Tyr Leu His Ala His Asp Tyr Ile His Arg Asp
785             790             795             800

Leu Ala Ala Arg Asn Val Leu Asp Asn Asp Arg Leu Val Lys Ile
            805             810             815

Gly Asp Phe Gly Leu Ala Lys Ala Val Pro Glu Gly His Glu Tyr Tyr
            820             825             830

Arg Val Arg Glu Asp Gly Asp Ser Pro Val Phe Trp Tyr Ala Pro Glu
            835             840             845

Cys Leu Lys Glu Tyr Lys Phe Tyr Tyr Ala Ser Asp Val Trp Ser Phe
850             855             860

Gly Val Thr Leu Tyr Glu Leu Leu Thr His Cys Asp Ser Ser Gln Ser
865             870             875             880

Pro Pro Thr Lys Phe Leu Glu Leu Ile Gly Ile Ala Gln Gly Gln Met
            885             890             895

Thr Val Leu Arg Leu Thr Glu Leu Leu Glu Arg Gly Glu Arg Leu Pro
            900             905             910

Arg Pro Asp Lys Cys Pro Cys Glu Val Tyr His Leu Met Lys Asn Cys
            915             920             925

Trp Glu Thr Glu Ala Ser Phe Arg Pro Thr Phe Glu Asn Leu Ile Pro
            930             935             940

Ile Leu Lys Thr Val His Glu Lys Tyr Gln Gly Gln Ala Pro Ser Val
945             950             955             960

Phe Ser Val Cys Leu Glu Tyr Pro Tyr Asp Val Pro Asp Tyr Ala
            965             970             975

<210> SEQ ID NO 5
<211> LENGTH: 1593
<212> TYPE: PRT
<213> ORGANISM: Artificial Sequence
<220> FEATURE:
<223> OTHER INFORMATION: ERN1-Tyk2(C) fusion construct
```

<400> SEQUENCE: 5

```
Met Pro Ala Arg Arg Leu Leu Leu Leu Thr Leu Leu Pro Gly
1               5                   10                  15
Leu Gly Ile Phe Gly Ser Thr Ser Val Thr Leu Pro Glu Thr Leu
            20                  25                  30
Leu Phe Val Ser Thr Leu Asp Gly Ser Leu His Ala Val Ser Lys Arg
        35                  40                  45
Thr Gly Ser Ile Lys Trp Thr Leu Lys Glu Asp Pro Val Leu Gln Val
    50                  55                  60
Pro Thr His Val Glu Glu Pro Ala Phe Leu Pro Asp Pro Asn Asp Gly
65              70                  75                  80
Ser Leu Tyr Thr Leu Gly Ser Lys Asn Asn Glu Gly Leu Thr Lys Leu
                85                  90                  95
Pro Phe Thr Ile Pro Glu Leu Val Gln Ala Ser Pro Cys Arg Ser Ser
            100                 105                 110
Asp Gly Ile Leu Tyr Met Gly Lys Lys Gln Asp Ile Trp Tyr Val Ile
        115                 120                 125
Asp Leu Leu Thr Gly Glu Lys Gln Gln Thr Leu Ser Ser Ala Phe Ala
    130                 135                 140
Asp Ser Leu Cys Pro Ser Thr Ser Leu Leu Tyr Leu Gly Arg Thr Glu
145                 150                 155                 160
Tyr Thr Ile Thr Met Tyr Asp Thr Lys Thr Arg Glu Leu Arg Trp Asn
                165                 170                 175
Ala Thr Tyr Phe Asp Tyr Ala Ala Ser Leu Pro Glu Asp Asp Val Asp
            180                 185                 190
Tyr Lys Met Ser His Phe Val Ser Asn Gly Asp Gly Leu Val Val Thr
        195                 200                 205
Val Asp Ser Glu Ser Gly Asp Val Leu Trp Ile Gln Asn Tyr Ala Ser
    210                 215                 220
Pro Val Val Ala Phe Tyr Val Trp Gln Arg Glu Gly Leu Arg Lys Val
225                 230                 235                 240
Met His Ile Asn Val Ala Val Glu Thr Leu Arg Tyr Leu Thr Phe Met
                245                 250                 255
Ser Gly Glu Val Gly Arg Ile Thr Lys Trp Lys Tyr Pro Phe Pro Lys
            260                 265                 270
Glu Thr Glu Ala Lys Ser Lys Leu Thr Pro Thr Leu Tyr Val Gly Lys
        275                 280                 285
Tyr Ser Thr Ser Leu Tyr Ala Ser Pro Ser Met Val His Glu Gly Val
    290                 295                 300
Ala Val Val Pro Arg Gly Ser Thr Leu Pro Leu Leu Glu Gly Pro Gln
305                 310                 315                 320
Thr Asp Gly Val Thr Ile Gly Asp Lys Gly Glu Cys Val Ile Thr Pro
                325                 330                 335
Ser Thr Asp Val Lys Phe Asp Pro Gly Leu Lys Ser Lys Asn Lys Leu
            340                 345                 350
Asn Tyr Leu Arg Asn Tyr Trp Leu Leu Ile Gly His His Glu Thr Pro
        355                 360                 365
Leu Ser Ala Ser Thr Lys Met Leu Glu Arg Phe Pro Asn Asn Leu Pro
    370                 375                 380
Lys His Arg Glu Asn Val Ile Pro Ala Asp Ser Glu Lys Lys Ser Phe
385                 390                 395                 400
Glu Glu Val Ile Asn Leu Val Asp Gln Thr Ser Glu Asn Ala Pro Thr
                405                 410                 415
```

```
Thr Val Ser Arg Asp Val Glu Lys Pro Ala His Ala Pro Ala Arg
            420                 425             430
Pro Glu Ala Pro Val Asp Ser Met Leu Lys Asp Met Ala Thr Ile Ile
        435                 440                 445
Leu Ser Thr Phe Leu Leu Ile Gly Trp Val Ala Phe Ile Ile Thr Tyr
    450                 455                 460
Pro Leu Ser Met His Gln Gln Gln Leu Gln His Gln Gln Phe Gln
465                 470                 475                 480
Lys Glu Leu Glu Lys Ile Gln Leu Leu Gln Gln Gln Gln Gln Leu
                485                 490                 495
Pro Phe His Pro Pro Gly Asp Thr Ala Gln Asp Gly Glu Leu Leu Asp
            500                 505                 510
Thr Ser Gly Pro Tyr Ser Glu Ser Ser Gly Thr Ser Ser Pro Ser Thr
            515                 520                 525
Ser Pro Arg Ala Ser Asn His Ser Leu Cys Ser Gly Ser Ser Ala Ser
    530                 535                 540
Lys Ala Gly Ser Ser Pro Ser Leu Glu Gln Asp Asp Gly Asp Glu Glu
545                 550                 555                 560
Thr Ser Val Val Ile Val Gly Lys Ile Ser Phe Cys Pro Lys Asp Val
                565                 570                 575
Leu Gly His Gly Ala Glu Gly Thr Ile Val Tyr Arg Gly Met Phe Asp
            580                 585                 590
Asn Arg Asp Val Ala Val Lys Arg Ile Leu Pro Glu Cys Phe Ser Phe
    595                 600                 605
Ala Asp Arg Glu Val Gln Leu Leu Arg Glu Ser Asp Glu His Pro Asn
            610                 615                 620
Val Ile Arg Tyr Phe Cys Thr Glu Lys Asp Arg Gln Phe Gln Tyr Ile
625                 630                 635                 640
Ala Ile Glu Leu Cys Ala Ala Thr Leu Gln Glu Tyr Val Glu Gln Lys
                645                 650                 655
Asp Phe Ala His Leu Gly Leu Glu Pro Ile Thr Leu Leu Gln Gln Thr
            660                 665                 670
Thr Ser Gly Leu Ala His Leu His Ser Leu Asn Ile Val His Arg Asp
    675                 680                 685
Leu Lys Pro His Asn Ile Leu Ile Ser Met Pro Asn Ala His Gly Lys
            690                 695                 700
Ile Lys Ala Met Ile Ser Asp Phe Gly Leu Cys Lys Lys Leu Ala Val
705                 710                 715                 720
Gly Arg His Ser Phe Ser Arg Arg Ser Gly Val Pro Gly Thr Glu Gly
                725                 730                 735
Trp Ile Ala Pro Glu Met Leu Ser Glu Asp Cys Lys Glu Asn Pro Thr
            740                 745                 750
Tyr Thr Val Asp Ile Phe Ser Ala Gly Cys Val Phe Tyr Tyr Val Ile
    755                 760                 765
Ser Glu Gly Ser His Pro Phe Gly Lys Ser Leu Gln Arg Gln Ala Asn
            770                 775                 780
Ile Leu Leu Gly Ala Cys Ser Leu Asp Cys Leu His Pro Glu Lys His
785                 790                 795                 800
Glu Asp Val Ile Ala Arg Glu Leu Ile Glu Lys Met Ile Ala Met Asp
                805                 810                 815
Pro Gln Lys Arg Pro Ser Ala Lys His Val Leu Lys His Pro Phe Phe
            820                 825                 830
```

-continued

```
Trp Ser Leu Glu Lys Gln Leu Gln Phe Phe Gln Asp Val Ser Asp Arg
            835                 840                 845

Ile Glu Lys Glu Ser Leu Asp Gly Pro Ile Val Lys Gln Leu Glu Arg
        850                 855                 860

Gly Gly Arg Ala Val Val Lys Met Asp Trp Arg Glu Asn Ile Thr Val
865                 870                 875                 880

Pro Leu Gln Thr Asp Leu Arg Lys Phe Arg Thr Tyr Lys Gly Gly Ser
                885                 890                 895

Val Arg Asp Leu Leu Arg Ala Met Arg Asn Lys Lys His His Tyr Arg
            900                 905                 910

Glu Leu Pro Ala Glu Val Arg Glu Thr Leu Gly Ser Leu Pro Asp Asp
        915                 920                 925

Phe Val Cys Tyr Phe Thr Ser Arg Phe Pro His Leu Leu Ala His Thr
    930                 935                 940

Tyr Arg Ala Met Glu Leu Cys Ser His Glu Arg Leu Phe Gln Pro Tyr
945                 950                 955                 960

Tyr Phe His Glu Pro Pro Glu Pro Gln Pro Val Thr Pro Asp Ala
                965                 970                 975

Leu Ala Ala Ala Gly Gly Ser Ile Thr Gln Leu Ser His Leu Gly Gln
            980                 985                 990

Gly Thr Arg Thr Asn Val Tyr Glu  Gly Arg Leu Arg Val  Glu Gly Ser
        995                 1000                1005

Gly Asp  Pro Glu Glu Gly Lys  Met Asp Asp Glu Asp  Pro Leu Val
    1010                1015                1020

Pro Gly  Arg Asp Arg Gly Gln  Glu Leu Arg Val Val  Leu Lys Val
    1025                1030                1035

Leu Asp  Pro Ser His His Asp  Ile Ala Leu Ala Phe  Tyr Glu Thr
    1040                1045                1050

Ala Ser  Leu Met Ser Gln Val  Ser His Thr His Leu  Ala Phe Val
    1055                1060                1065

His Gly  Val Cys Val Arg Gly  Pro Glu Asn Ser Met  Val Thr Glu
    1070                1075                1080

Tyr Val  Glu His Gly Pro Leu  Asp Val Trp Leu Arg  Arg Glu Arg
    1085                1090                1095

Gly His  Val Pro Met Ala Trp  Lys Met Val Val Ala  Gln Gln Leu
    1100                1105                1110

Ala Ser  Ala Leu Ser Tyr Leu  Glu Asn Lys Asn Leu  Val His Gly
    1115                1120                1125

Asn Val  Cys Gly Arg Asn Ile  Leu Leu Ala Arg Leu  Gly Leu Ala
    1130                1135                1140

Glu Gly  Thr Ser Pro Phe Ile  Lys Leu Ser Asp Pro  Gly Val Gly
    1145                1150                1155

Leu Gly  Ala Leu Ser Arg Glu  Glu Arg Val Glu Arg  Ile Pro Trp
    1160                1165                1170

Leu Ala  Pro Glu Cys Leu Pro  Gly Gly Ala Asn Ser  Leu Ser Thr
    1175                1180                1185

Ala Met  Asp Lys Trp Gly Phe  Gly Ala Thr Leu Leu  Glu Ile Cys
    1190                1195                1200

Phe Asp  Gly Glu Ala Pro Leu  Gln Ser Arg Ser Pro  Ser Glu Lys
    1205                1210                1215

Glu His  Phe Tyr Gln Arg Gln  His Arg Leu Pro Glu  Pro Ser Cys
    1220                1225                1230

Pro Gln  Leu Ala Thr Leu Thr  Ser Gln Cys Leu Thr  Tyr Glu Pro
```

```
                    1235                1240                1245

Thr Gln Arg Pro Ser Phe Arg Thr Ile Leu Arg Asp Leu Thr Arg
    1250                1255                1260

Val Gln Pro His Asn Leu Ala Asp Val Leu Thr Val Asn Arg Asp
    1265                1270                1275

Ser Pro Ala Val Gly Pro Thr Thr Phe His Lys Arg Tyr Leu Lys
    1280                1285                1290

Lys Ile Arg Asp Leu Gly Glu Gly His Phe Gly Lys Val Ser Leu
    1295                1300                1305

Tyr Cys Tyr Asp Pro Thr Asn Asp Gly Thr Gly Glu Met Val Ala
    1310                1315                1320

Val Lys Ala Leu Lys Ala Asp Cys Gly Pro Gln His Arg Ser Gly
    1325                1330                1335

Trp Lys Gln Glu Ile Asp Ile Leu Arg Thr Leu Tyr His Glu His
    1340                1345                1350

Ile Ile Lys Tyr Lys Gly Cys Cys Glu Asp Gln Gly Glu Lys Ser
    1355                1360                1365

Leu Gln Leu Val Met Glu Tyr Val Pro Leu Gly Ser Leu Arg Asp
    1370                1375                1380

Tyr Leu Pro Arg His Ser Ile Gly Leu Ala Gln Leu Leu Leu Phe
    1385                1390                1395

Ala Gln Gln Ile Cys Glu Gly Met Ala Tyr Leu His Ala His Asp
    1400                1405                1410

Tyr Ile His Arg Asp Leu Ala Ala Arg Asn Val Leu Leu Asp Asn
    1415                1420                1425

Asp Arg Leu Val Lys Ile Gly Asp Phe Gly Leu Ala Lys Ala Val
    1430                1435                1440

Pro Glu Gly His Glu Tyr Tyr Arg Val Arg Glu Asp Gly Asp Ser
    1445                1450                1455

Pro Val Phe Trp Tyr Ala Pro Glu Cys Leu Lys Glu Tyr Lys Phe
    1460                1465                1470

Tyr Tyr Ala Ser Asp Val Trp Ser Phe Gly Val Thr Leu Tyr Glu
    1475                1480                1485

Leu Leu Thr His Cys Asp Ser Ser Gln Ser Pro Pro Thr Lys Phe
    1490                1495                1500

Leu Glu Leu Ile Gly Ile Ala Gln Gly Gln Met Thr Val Leu Arg
    1505                1510                1515

Leu Thr Glu Leu Leu Glu Arg Gly Glu Arg Leu Pro Arg Pro Asp
    1520                1525                1530

Lys Cys Pro Cys Glu Val Tyr His Leu Met Lys Asn Cys Trp Glu
    1535                1540                1545

Thr Glu Ala Ser Phe Arg Pro Thr Phe Glu Asn Leu Ile Pro Ile
    1550                1555                1560

Leu Lys Thr Val His Glu Lys Tyr Gln Gly Gln Ala Pro Ser Val
    1565                1570                1575

Phe Ser Val Cys Leu Glu Tyr Pro Tyr Asp Val Pro Asp Tyr Ala
    1580                1585                1590
```

<210> SEQ ID NO 6
<211> LENGTH: 612
<212> TYPE: PRT
<213> ORGANISM: Artificial Sequence
<220> FEATURE:
<223> OTHER INFORMATION: gp130-ARRB2 fusion construct

<400> SEQUENCE: 6

```
Met Asp Tyr Lys Asp Asp Asp Lys Ile Ser Thr Val Val His Ser
1               5                   10                  15

Gly Tyr Arg His Gln Val Pro Ser Val Gln Val Phe Ser Arg Ser Glu
            20                  25                  30

Ser Thr Gln Pro Leu Leu Asp Ser Glu Glu Arg Pro Glu Asp Leu Gln
        35                  40                  45

Leu Val Asp His Val Asp Gly Gly Asp Gly Ile Leu Pro Arg Gln Gln
    50                  55                  60

Tyr Phe Lys Gln Asn Cys Ser Gln His Glu Ser Ser Pro Asp Ile Ser
65                  70                  75                  80

His Phe Glu Arg Ser Lys Gln Val Ser Ser Val Asn Glu Glu Asp Phe
                85                  90                  95

Val Arg Leu Lys Gln Gln Ile Ser Asp His Ile Ser Gln Ser Cys Gly
            100                 105                 110

Ser Gly Gln Met Lys Met Phe Gln Glu Val Ser Ala Ala Asp Ala Phe
        115                 120                 125

Gly Pro Gly Thr Glu Gly Gln Val Glu Arg Phe Glu Thr Val Gly Met
    130                 135                 140

Glu Ala Ala Thr Asp Glu Gly Met Pro Lys Ser Tyr Leu Pro Gln Thr
145                 150                 155                 160

Val Arg Gln Gly Gly Tyr Met Pro Gln Gly Gly Ser Glu Leu Ser Thr
                165                 170                 175

Ser Leu Tyr Lys Lys Ala Gly Tyr Leu Pro Gln Thr Val Arg Gln Gly
            180                 185                 190

Gly Tyr Met Pro Gln Gly Gly Ser Glu Phe Thr Met Gly Glu Lys Pro
    195                 200                 205

Gly Thr Arg Val Phe Lys Lys Ser Ser Pro Asn Cys Lys Leu Thr Val
    210                 215                 220

Tyr Leu Gly Lys Arg Asp Phe Val Asp His Leu Asp Lys Val Asp Pro
225                 230                 235                 240

Val Asp Gly Val Val Leu Val Asp Pro Asp Tyr Leu Lys Asp Arg Lys
                245                 250                 255

Val Phe Val Thr Leu Thr Cys Ala Phe Arg Tyr Gly Arg Glu Asp Leu
            260                 265                 270

Asp Val Leu Gly Leu Ser Phe Arg Lys Asp Leu Phe Ile Ala Thr Tyr
        275                 280                 285

Gln Ala Phe Pro Pro Val Pro Asn Pro Pro Arg Pro Pro Thr Arg Leu
    290                 295                 300

Gln Asp Arg Leu Leu Arg Lys Leu Gly Gln His Ala His Pro Phe Phe
305                 310                 315                 320

Phe Thr Ile Pro Gln Asn Leu Pro Cys Ser Val Thr Leu Gln Pro Gly
                325                 330                 335

Pro Glu Asp Thr Gly Lys Ala Cys Gly Val Asp Phe Glu Ile Arg Ala
            340                 345                 350

Phe Cys Ala Lys Ser Leu Glu Glu Lys Ser His Lys Arg Asn Ser Val
        355                 360                 365

Arg Leu Val Ile Arg Lys Val Gln Phe Ala Pro Glu Lys Pro Gly Pro
    370                 375                 380

Gln Pro Ser Ala Glu Thr Thr Arg His Phe Leu Met Ser Asp Arg Ser
385                 390                 395                 400

Leu His Leu Glu Ala Ser Leu Asp Lys Glu Leu Tyr Tyr His Gly Glu
                405                 410                 415
```

```
Pro Leu Asn Val Asn Val His Val Thr Asn Asn Ser Thr Lys Thr Val
            420                 425                 430

Lys Lys Ile Lys Val Ser Val Arg Gln Tyr Ala Asp Ile Cys Leu Phe
        435                 440                 445

Ser Thr Ala Gln Tyr Lys Cys Pro Val Ala Gln Leu Glu Gln Asp Asp
    450                 455                 460

Gln Val Ser Pro Ser Ser Thr Phe Cys Lys Val Tyr Thr Ile Thr Pro
465                 470                 475                 480

Leu Leu Ser Asp Asn Arg Glu Lys Arg Gly Leu Ala Leu Asp Gly Lys
                485                 490                 495

Leu Lys His Glu Asp Thr Asn Leu Ala Ser Ser Thr Ile Val Lys Glu
            500                 505                 510

Gly Ala Asn Lys Glu Val Leu Gly Ile Leu Val Ser Tyr Arg Val Lys
        515                 520                 525

Val Lys Leu Val Val Ser Arg Gly Gly Asp Val Ser Val Glu Leu Pro
530                 535                 540

Phe Val Leu Met His Pro Lys Pro His Asp His Ile Pro Leu Pro Arg
545                 550                 555                 560

Pro Gln Ser Ala Ala Pro Glu Thr Asp Val Pro Val Asp Thr Asn Leu
                565                 570                 575

Ile Glu Phe Asp Thr Asn Tyr Ala Thr Asp Asp Ile Val Phe Glu
            580                 585                 590

Asp Phe Ala Arg Leu Arg Leu Lys Gly Met Lys Asp Asp Tyr Asp
        595                 600                 605

Asp Gln Leu Cys
    610

<210> SEQ ID NO 7
<211> LENGTH: 1187
<212> TYPE: PRT
<213> ORGANISM: Artificial Sequence
<220> FEATURE:
<223> OTHER INFORMATION: ERN1-gp130 fusion construct

<400> SEQUENCE: 7

Met Asp Tyr Lys Asp Asp Asp Lys Ile Ser Glu Phe Thr Met Pro
1               5                   10                  15

Ala Arg Arg Leu Leu Leu Leu Leu Thr Leu Leu Leu Pro Gly Leu Gly
            20                  25                  30

Ile Phe Gly Ser Thr Ser Thr Val Thr Leu Pro Glu Thr Leu Leu Phe
        35                  40                  45

Val Ser Thr Leu Asp Gly Ser Leu His Ala Val Ser Lys Arg Thr Gly
    50                  55                  60

Ser Ile Lys Trp Thr Leu Lys Glu Asp Pro Val Leu Gln Val Pro Thr
65                  70                  75                  80

His Val Glu Glu Pro Ala Phe Leu Pro Asp Pro Asn Asp Gly Ser Leu
                85                  90                  95

Tyr Thr Leu Gly Ser Lys Asn Asn Glu Gly Leu Thr Lys Leu Pro Phe
            100                 105                 110

Thr Ile Pro Glu Leu Val Gln Ala Ser Pro Cys Arg Ser Ser Asp Gly
        115                 120                 125

Ile Leu Tyr Met Gly Lys Lys Gln Asp Ile Trp Tyr Val Ile Asp Leu
    130                 135                 140

Leu Thr Gly Glu Lys Gln Gln Thr Leu Ser Ser Ala Phe Ala Asp Ser
145                 150                 155                 160
```

```
Leu Cys Pro Ser Thr Ser Leu Leu Tyr Leu Gly Arg Thr Glu Tyr Thr
                165                 170                 175
Ile Thr Met Tyr Asp Thr Lys Thr Arg Glu Leu Arg Trp Asn Ala Thr
            180                 185                 190
Tyr Phe Asp Tyr Ala Ala Ser Leu Pro Glu Asp Val Asp Tyr Lys
        195                 200                 205
Met Ser His Phe Val Ser Asn Gly Asp Gly Leu Val Val Thr Val Asp
    210                 215                 220
Ser Glu Ser Gly Asp Val Leu Trp Ile Gln Asn Tyr Ala Ser Pro Val
225                 230                 235                 240
Val Ala Phe Tyr Val Trp Gln Arg Glu Gly Leu Arg Lys Val Met His
            245                 250                 255
Ile Asn Val Ala Val Glu Thr Leu Arg Tyr Leu Thr Phe Met Ser Gly
        260                 265                 270
Glu Val Gly Arg Ile Thr Lys Trp Lys Tyr Pro Phe Pro Lys Glu Thr
    275                 280                 285
Glu Ala Lys Ser Lys Leu Thr Pro Thr Leu Tyr Val Gly Lys Tyr Ser
290                 295                 300
Thr Ser Leu Tyr Ala Ser Pro Ser Met Val His Glu Gly Val Ala Val
305                 310                 315                 320
Val Pro Arg Gly Ser Thr Leu Pro Leu Leu Glu Gly Pro Gln Thr Asp
            325                 330                 335
Gly Val Thr Ile Gly Asp Lys Gly Glu Cys Val Ile Thr Pro Ser Thr
        340                 345                 350
Asp Val Lys Phe Asp Pro Gly Leu Lys Ser Lys Asn Lys Leu Asn Tyr
    355                 360                 365
Leu Arg Asn Tyr Trp Leu Leu Ile Gly His His Glu Thr Pro Leu Ser
370                 375                 380
Ala Ser Thr Lys Met Leu Glu Arg Phe Pro Asn Asn Leu Pro Lys His
385                 390                 395                 400
Arg Glu Asn Val Ile Pro Ala Asp Ser Glu Lys Lys Ser Phe Glu Glu
            405                 410                 415
Val Ile Asn Leu Val Asp Gln Thr Ser Glu Asn Ala Pro Thr Thr Val
        420                 425                 430
Ser Arg Asp Val Glu Glu Lys Pro Ala His Ala Pro Ala Arg Pro Glu
    435                 440                 445
Ala Pro Val Asp Ser Met Leu Lys Asp Met Ala Thr Ile Ile Leu Ser
450                 455                 460
Thr Phe Leu Leu Ile Gly Trp Val Ala Phe Ile Ile Thr Tyr Pro Leu
465                 470                 475                 480
Ser Met His Gln Gln Gln Leu Gln His Gln Gln Phe Gln Lys Glu
            485                 490                 495
Leu Glu Lys Ile Gln Leu Leu Gln Gln Gln Gln Gln Leu Pro Phe
        500                 505                 510
His Pro Pro Gly Asp Thr Ala Gln Asp Gly Glu Leu Leu Asp Thr Ser
    515                 520                 525
Gly Pro Tyr Ser Glu Ser Ser Gly Thr Ser Ser Pro Ser Thr Ser Pro
530                 535                 540
Arg Ala Ser Asn His Ser Leu Cys Ser Gly Ser Ser Ala Ser Lys Ala
545                 550                 555                 560
Gly Ser Ser Pro Ser Leu Glu Gln Asp Asp Gly Asp Glu Glu Thr Ser
            565                 570                 575
```

-continued

```
Val Val Ile Val Gly Lys Ile Ser Phe Cys Pro Lys Asp Val Leu Gly
            580                 585                 590

His Gly Ala Glu Gly Thr Ile Val Tyr Arg Gly Met Phe Asp Asn Arg
            595                 600                 605

Asp Val Ala Val Lys Arg Ile Leu Pro Glu Cys Phe Ser Phe Ala Asp
            610                 615                 620

Arg Glu Val Gln Leu Leu Arg Glu Ser Asp Glu His Pro Asn Val Ile
625                 630                 635                 640

Arg Tyr Phe Cys Thr Glu Lys Asp Arg Gln Phe Gln Tyr Ile Ala Ile
            645                 650                 655

Glu Leu Cys Ala Ala Thr Leu Gln Glu Tyr Val Glu Gln Lys Asp Phe
            660                 665                 670

Ala His Leu Gly Leu Glu Pro Ile Thr Leu Leu Gln Gln Thr Thr Ser
            675                 680                 685

Gly Leu Ala His Leu His Ser Leu Asn Ile Val His Arg Asp Leu Lys
            690                 695                 700

Pro His Asn Ile Leu Ile Ser Met Pro Asn Ala His Gly Lys Ile Lys
705                 710                 715                 720

Ala Met Ile Ser Asp Phe Gly Leu Cys Lys Lys Leu Ala Val Gly Arg
            725                 730                 735

His Ser Phe Ser Arg Arg Ser Gly Val Pro Gly Thr Glu Gly Trp Ile
            740                 745                 750

Ala Pro Glu Met Leu Ser Glu Asp Cys Lys Glu Asn Pro Thr Tyr Thr
            755                 760                 765

Val Asp Ile Phe Ser Ala Gly Cys Val Phe Tyr Tyr Val Ile Ser Glu
            770                 775                 780

Gly Ser His Pro Phe Gly Lys Ser Leu Gln Arg Gln Ala Asn Ile Leu
785                 790                 795                 800

Leu Gly Ala Cys Ser Leu Asp Cys Leu His Pro Glu Lys His Glu Asp
            805                 810                 815

Val Ile Ala Arg Glu Leu Ile Glu Lys Met Ile Ala Met Asp Pro Gln
            820                 825                 830

Lys Arg Pro Ser Ala Lys His Val Leu Lys His Pro Phe Phe Trp Ser
            835                 840                 845

Leu Glu Lys Gln Leu Gln Phe Phe Gln Asp Val Ser Asp Arg Ile Glu
            850                 855                 860

Lys Glu Ser Leu Asp Gly Pro Ile Val Lys Gln Leu Glu Arg Gly Gly
865                 870                 875                 880

Arg Ala Val Val Lys Met Asp Trp Arg Glu Asn Ile Thr Val Pro Leu
            885                 890                 895

Gln Thr Asp Leu Arg Lys Phe Arg Thr Tyr Lys Gly Gly Ser Val Arg
            900                 905                 910

Asp Leu Leu Arg Ala Met Arg Asn Lys Lys His His Tyr Arg Glu Leu
            915                 920                 925

Pro Ala Glu Val Arg Glu Thr Leu Gly Ser Leu Pro Asp Asp Phe Val
            930                 935                 940

Cys Tyr Phe Thr Ser Arg Phe Pro His Leu Leu Ala His Thr Tyr Arg
945                 950                 955                 960

Ala Met Glu Leu Cys Ser His Glu Arg Leu Phe Gln Pro Tyr Tyr Phe
            965                 970                 975

His Glu Pro Pro Glu Pro Gln Pro Pro Val Thr Pro Asp Ala Leu Ser
            980                 985                 990

Arg Gly Ser Gly Gly Ser Gly Gly  Ser Thr Val Val His  Ser Gly Tyr
```

-continued

```
                    995                 1000                1005
Arg  His  Gln  Val  Pro  Ser  Val  Gln  Val  Phe  Ser  Arg  Ser  Glu  Ser
        1010                1015                1020

Thr  Gln  Pro  Leu  Leu  Asp  Ser  Glu  Arg  Pro  Glu  Asp  Leu  Gln
        1025                1030                1035

Leu  Val  Asp  His  Val  Asp  Gly  Asp  Gly  Ile  Leu  Pro  Arg  Gln
        1040                1045                1050

Gln  Tyr  Phe  Lys  Gln  Asn  Cys  Ser  Gln  His  Glu  Ser  Ser  Pro  Asp
        1055                1060                1065

Ile  Ser  His  Phe  Glu  Arg  Ser  Lys  Gln  Val  Ser  Ser  Val  Asn  Glu
        1070                1075                1080

Glu  Asp  Phe  Val  Arg  Leu  Lys  Gln  Gln  Ile  Ser  Asp  His  Ile  Ser
        1085                1090                1095

Gln  Ser  Cys  Gly  Ser  Gly  Gln  Met  Lys  Met  Phe  Gln  Glu  Val  Ser
        1100                1105                1110

Ala  Ala  Asp  Ala  Phe  Gly  Pro  Gly  Thr  Glu  Gly  Gln  Val  Glu  Arg
        1115                1120                1125

Phe  Glu  Thr  Val  Gly  Met  Glu  Ala  Ala  Thr  Asp  Glu  Gly  Met  Pro
        1130                1135                1140

Lys  Ser  Tyr  Leu  Pro  Gln  Thr  Val  Arg  Gln  Gly  Gly  Tyr  Met  Pro
        1145                1150                1155

Gln  Gly  Gly  Ser  Glu  Leu  Ser  Thr  Ser  Leu  Tyr  Lys  Lys  Ala  Gly
        1160                1165                1170

Tyr  Leu  Pro  Gln  Thr  Val  Arg  Gln  Gly  Gly  Tyr  Met  Pro  Gln
        1175                1180                1185
```

<210> SEQ ID NO 8
<211> LENGTH: 522
<212> TYPE: PRT
<213> ORGANISM: Homo sapiens

<400> SEQUENCE: 8

```
Gly  Ser  Asn  Lys  Ser  Lys  Pro  Lys  Asp  Ala  Ser  Gln  Arg  Arg  Arg  Ser
1                 5                   10                  15

Leu  Glu  Pro  Ala  Glu  Asn  Val  His  Gly  Ala  Gly  Gly  Gly  Ala  Phe  Pro
            20                  25                  30

Ala  Ser  Gln  Thr  Pro  Ser  Lys  Pro  Ala  Ser  Ala  Asp  Gly  His  Arg  Gly
        35                  40                  45

Pro  Ser  Ala  Ala  Phe  Ala  Pro  Ala  Ala  Glu  Pro  Lys  Leu  Phe  Gly
    50                  55                  60

Gly  Phe  Asn  Ser  Ser  Asp  Thr  Val  Thr  Ser  Pro  Gln  Arg  Ala  Gly  Pro
65                  70                  75                  80

Leu  Ala  Gly  Gly  Val  Thr  Thr  Phe  Val  Ala  Leu  Tyr  Asp  Tyr  Glu  Ser
                85                  90                  95

Arg  Thr  Glu  Thr  Asp  Leu  Ser  Phe  Lys  Lys  Gly  Glu  Arg  Leu  Gln  Ile
            100                 105                 110

Val  Asn  Asn  Thr  Glu  Gly  Asp  Trp  Trp  Leu  Ala  His  Ser  Leu  Ser  Thr
        115                 120                 125

Gly  Gln  Thr  Gly  Tyr  Ile  Pro  Ser  Asn  Tyr  Val  Ala  Pro  Ser  Asp  Ser
    130                 135                 140

Ile  Gln  Ala  Glu  Glu  Trp  Tyr  Phe  Gly  Lys  Ile  Thr  Arg  Arg  Glu  Ser
145                 150                 155                 160

Glu  Arg  Leu  Leu  Leu  Asn  Ala  Glu  Asn  Pro  Arg  Gly  Thr  Phe  Leu  Val
                165                 170                 175
```

Arg Glu Ser Glu Thr Thr Lys Gly Ala Tyr Cys Leu Ser Val Ser Asp
                180                 185                 190

Phe Asp Asn Ala Lys Gly Leu Asn Val Lys His Tyr Lys Ile Arg Lys
            195                 200                 205

Leu Asp Ser Gly Gly Phe Tyr Ile Thr Ser Arg Thr Gln Phe Asn Ser
        210                 215                 220

Leu Gln Gln Leu Val Ala Tyr Tyr Ser Lys His Ala Asp Gly Leu Cys
225                 230                 235                 240

His Arg Leu Thr Thr Val Cys Pro Thr Ser Lys Pro Gln Thr Gln Gly
                245                 250                 255

Leu Ala Lys Asp Ala Trp Glu Ile Pro Arg Glu Ser Leu Arg Leu Glu
            260                 265                 270

Val Lys Leu Gly Gln Gly Cys Phe Gly Glu Val Trp Met Gly Thr Trp
        275                 280                 285

Asn Gly Thr Thr Arg Val Ala Ile Lys Thr Leu Lys Pro Gly Thr Met
        290                 295                 300

Ser Pro Glu Ala Phe Leu Gln Glu Ala Gln Val Met Lys Lys Leu Arg
305                 310                 315                 320

His Glu Lys Leu Val Gln Leu Tyr Ala Val Val Ser Glu Glu Pro Ile
                325                 330                 335

Tyr Ile Val Thr Glu Tyr Met Ser Lys Gly Ser Leu Leu Asp Phe Leu
            340                 345                 350

Lys Gly Glu Thr Gly Lys Tyr Leu Arg Leu Pro Gln Leu Val Asp Met
        355                 360                 365

Ala Ala Gln Ile Ala Ser Gly Met Ala Tyr Val Glu Arg Met Asn Tyr
        370                 375                 380

Val His Arg Asp Leu Arg Ala Ala Asn Ile Leu Val Gly Glu Asn Leu
385                 390                 395                 400

Val Cys Lys Val Ala Asp Phe Gly Leu Ala Arg Leu Ile Glu Asp Asn
                405                 410                 415

Glu Tyr Thr Ala Arg Gln Gly Ala Lys Phe Pro Ile Lys Trp Thr Ala
            420                 425                 430

Pro Glu Ala Ala Leu Tyr Gly Arg Phe Thr Ile Lys Ser Asp Val Trp
        435                 440                 445

Ser Phe Gly Ile Leu Leu Thr Glu Leu Thr Thr Lys Gly Arg Val Pro
450                 455                 460

Tyr Pro Gly Met Val Asn Arg Glu Val Leu Asp Gln Val Glu Arg Gly
465                 470                 475                 480

Tyr Arg Met Pro Cys Pro Pro Glu Cys Pro Glu Ser Leu His Asp Leu
                485                 490                 495

Met Cys Gln Cys Trp Arg Lys Glu Pro Glu Glu Arg Pro Thr Phe Glu
            500                 505                 510

Tyr Leu Gln Ala Phe Leu Glu Asp Tyr Phe
        515                 520

<210> SEQ ID NO 9
<211> LENGTH: 38
<212> TYPE: DNA
<213> ORGANISM: Artificial Sequence
<220> FEATURE:
<223> OTHER INFORMATION: Primer

<400> SEQUENCE: 9
cccaccggtc cggaattgac aagtttgtac aaaaaagc                              38

```
<210> SEQ ID NO 10
<211> LENGTH: 31
<212> TYPE: DNA
<213> ORGANISM: Artificial Sequence
<220> FEATURE:
<223> OTHER INFORMATION: Primer

<400> SEQUENCE: 10 gggggggcccc aaccactttg tacaagaaag c                                    31

<210> SEQ ID NO 11
<211> LENGTH: 43
<212> TYPE: DNA
<213> ORGANISM: Artificial Sequence
<220> FEATURE:
<223> OTHER INFORMATION: Primer

<400> SEQUENCE: 11
cccgcggccg ctggcggttc gatcacccag ctgtcccact tgg                        43

<210> SEQ ID NO 12
<211> LENGTH: 63
<212> TYPE: DNA
<213> ORGANISM: Artificial Sequence
<220> FEATURE:
<223> OTHER INFORMATION: Primer

<400> SEQUENCE: 12
tctagactaa gcataatctg aacatcata tggatactcg aggcacacgc tgaacactga       60
agg                                                                    63

<210> SEQ ID NO 13
<211> LENGTH: 73
<212> TYPE: DNA
<213> ORGANISM: Artificial Sequence
<220> FEATURE:
<223> OTHER INFORMATION: Primer

<400> SEQUENCE: 13
ccccaattga ccatgtatcc atatgatgtt ccagattatg ctttaattaa aatcacccag      60
ctgtcccact tgg                                                         73

<210> SEQ ID NO 14
<211> LENGTH: 64
<212> TYPE: DNA
<213> ORGANISM: Artificial Sequence
<220> FEATURE:
<223> OTHER INFORMATION: Primer

<400> SEQUENCE: 14
gggtctagag cggccgcacc ggtcttaatt aagtcgacga attcgcacac gctgaacact      60
gaag                                                                   64

<210> SEQ ID NO 15
<211> LENGTH: 38
<212> TYPE: DNA
<213> ORGANISM: Artificial Sequence
<220> FEATURE:
<223> OTHER INFORMATION: Primer

<400> SEQUENCE: 15
cccaagcttg aattcaccat gggggagaaa cccgggac                              38

<210> SEQ ID NO 16
```

```
<211> LENGTH: 33
<212> TYPE: DNA
<213> ORGANISM: Artificial Sequence
<220> FEATURE:
<223> OTHER INFORMATION: Primer

<400> SEQUENCE: 16
ggggcggccg cctagcagag ttgatcatca tag                              33

<210> SEQ ID NO 17
<211> LENGTH: 39
<212> TYPE: DNA
<213> ORGANISM: Artificial Sequence
<220> FEATURE:
<223> OTHER INFORMATION: Primer

<400> SEQUENCE: 17
cccaagcttg gtaccaccat gccggcccgg cggctgctg                        39

<210> SEQ ID NO 18
<211> LENGTH: 38
<212> TYPE: DNA
<213> ORGANISM: Artificial Sequence
<220> FEATURE:
<223> OTHER INFORMATION: Primer

<400> SEQUENCE: 18
cccgcggccg cgctagcgag ggcgtctgga gtcactgg                         38

<210> SEQ ID NO 19
<211> LENGTH: 43
<212> TYPE: DNA
<213> ORGANISM: Artificial Sequence
<220> FEATURE:
<223> OTHER INFORMATION: Primer

<400> SEQUENCE: 19
cccgcggccg ctggcggttc gatcacccag ctgtcccact tgg                   43

<210> SEQ ID NO 20
<211> LENGTH: 63
<212> TYPE: DNA
<213> ORGANISM: Artificial Sequence
<220> FEATURE:
<223> OTHER INFORMATION: Primer

<400> SEQUENCE: 20
gggcccctaa gcataatctg gaacatcata tggatactcg aggcacacgc tgaacactga  60
agg                                                                63

<210> SEQ ID NO 21
<211> LENGTH: 30
<212> TYPE: DNA
<213> ORGANISM: Artificial Sequence
<220> FEATURE:
<223> OTHER INFORMATION: Primer

<400> SEQUENCE: 21
cccgaattca tgccggcccg gcggctgctg                                  30

<210> SEQ ID NO 22
<211> LENGTH: 32
<212> TYPE: DNA
<213> ORGANISM: Artificial Sequence
<220> FEATURE:
<223> OTHER INFORMATION: Primer
```

```
<400> SEQUENCE: 22
cccctcgagg ggagggcgtc tggagtcact gg                                    32

<210> SEQ ID NO 23
<211> LENGTH: 30
<212> TYPE: DNA
<213> ORGANISM: Artificial Sequence
<220> FEATURE:
<223> OTHER INFORMATION: Primer

<400> SEQUENCE: 23
cccgaattct tctgtcccaa ggatgtcctg                                       30

<210> SEQ ID NO 24
<211> LENGTH: 35
<212> TYPE: DNA
<213> ORGANISM: Artificial Sequence
<220> FEATURE:
<223> OTHER INFORMATION: Primer

<400> SEQUENCE: 24
gggtaaaaag cagccatct ggtatgttat tgacc                                  35

<210> SEQ ID NO 25
<211> LENGTH: 35
<212> TYPE: DNA
<213> ORGANISM: Artificial Sequence
<220> FEATURE:
<223> OTHER INFORMATION: Primer

<400> SEQUENCE: 25
ggtcaataac ataccagatg ggctgctttt taccc                                 35

<210> SEQ ID NO 26
<211> LENGTH: 30
<212> TYPE: DNA
<213> ORGANISM: Artificial Sequence
<220> FEATURE:
<223> OTHER INFORMATION: Primer

<400> SEQUENCE: 26
cccgatatct atggagacga cgcccttgaa                                       30

<210> SEQ ID NO 27
<211> LENGTH: 31
<212> TYPE: DNA
<213> ORGANISM: Artificial Sequence
<220> FEATURE:
<223> OTHER INFORMATION: Primer

<400> SEQUENCE: 27
ggggcggccg cttacacagc attcaagcgg a                                     31

<210> SEQ ID NO 28
<211> LENGTH: 1177
<212> TYPE: PRT
<213> ORGANISM: Artificial Sequence
<220> FEATURE:
<223> OTHER INFORMATION: HA-Tyk2(C)-RTp66 construct

<400> SEQUENCE: 28

Met Tyr Pro Tyr Asp Val Pro Asp Tyr Ala Leu Ile Lys Ile Thr Gln
  1               5                  10                  15

Leu Ser His Leu Gly Gln Gly Thr Arg Thr Asn Val Tyr Glu Gly Arg
```

```
            20                  25                  30
Leu Arg Val Glu Gly Ser Gly Asp Pro Glu Gly Lys Met Asp Asp
            35                  40                  45
Glu Asp Pro Leu Val Pro Gly Arg Asp Arg Gly Gln Glu Leu Arg Val
        50                  55                  60
Val Leu Lys Val Leu Asp Pro Ser His His Asp Ile Ala Leu Ala Phe
65                  70                  75                  80
Tyr Glu Thr Ala Ser Leu Met Ser Gln Val Ser His Thr His Leu Ala
                85                  90                  95
Phe Val His Gly Val Cys Val Arg Gly Pro Glu Asn Ser Met Val Thr
            100                 105                 110
Glu Tyr Val Glu His Gly Pro Leu Asp Val Trp Leu Arg Arg Glu Arg
            115                 120                 125
Gly His Val Pro Met Ala Trp Lys Met Val Val Ala Gln Gln Leu Ala
            130                 135                 140
Ser Ala Leu Ser Tyr Leu Glu Asn Lys Asn Leu Val His Gly Asn Val
145                 150                 155                 160
Cys Gly Arg Asn Ile Leu Leu Ala Arg Leu Gly Leu Ala Glu Gly Thr
                165                 170                 175
Ser Pro Phe Ile Lys Leu Ser Asp Pro Gly Val Gly Leu Gly Ala Leu
            180                 185                 190
Ser Arg Glu Glu Arg Val Glu Arg Ile Pro Trp Leu Ala Pro Glu Cys
        195                 200                 205
Leu Pro Gly Gly Ala Asn Ser Leu Ser Thr Ala Met Asp Lys Trp Gly
        210                 215                 220
Phe Gly Ala Thr Leu Leu Glu Ile Cys Phe Asp Gly Glu Ala Pro Leu
225                 230                 235                 240
Gln Ser Arg Ser Pro Ser Glu Lys Glu His Phe Tyr Gln Arg Gln His
                245                 250                 255
Arg Leu Pro Glu Pro Ser Cys Pro Gln Leu Ala Thr Leu Thr Ser Gln
            260                 265                 270
Cys Leu Thr Tyr Glu Pro Thr Gln Arg Pro Ser Phe Arg Thr Ile Leu
        275                 280                 285
Arg Asp Leu Thr Arg Val Gln Pro His Asn Leu Ala Asp Val Leu Thr
        290                 295                 300
Val Asn Arg Asp Ser Pro Ala Val Gly Pro Thr Thr Phe His Lys Arg
305                 310                 315                 320
Tyr Leu Lys Lys Ile Arg Asp Leu Gly Glu Gly His Phe Gly Lys Val
                325                 330                 335
Ser Leu Tyr Cys Tyr Asp Pro Thr Asn Asp Gly Thr Gly Glu Met Val
            340                 345                 350
Ala Val Lys Ala Leu Lys Ala Asp Cys Gly Pro Gln His Arg Ser Gly
            355                 360                 365
Trp Lys Gln Glu Ile Asp Ile Leu Arg Thr Leu Tyr His Glu His Ile
            370                 375                 380
Ile Lys Tyr Lys Gly Cys Cys Glu Asp Gln Gly Glu Lys Ser Leu Gln
385                 390                 395                 400
Leu Val Met Glu Tyr Val Pro Leu Gly Ser Leu Arg Asp Tyr Leu Pro
                405                 410                 415
Arg His Ser Ile Gly Leu Ala Gln Leu Leu Leu Phe Ala Gln Gln Ile
            420                 425                 430
Cys Glu Gly Met Ala Tyr Leu His Ala His Asp Tyr Ile His Arg Asp
            435                 440                 445
```

```
Leu Ala Ala Arg Asn Val Leu Leu Asp Asn Asp Arg Leu Val Lys Ile
        450                 455                 460

Gly Asp Phe Gly Leu Ala Lys Ala Val Pro Glu Gly His Glu Tyr Tyr
465                 470                 475                 480

Arg Val Arg Glu Asp Gly Asp Ser Pro Val Phe Trp Tyr Ala Pro Glu
                485                 490                 495

Cys Leu Lys Glu Tyr Lys Phe Tyr Tyr Ala Ser Asp Val Trp Ser Phe
                500                 505                 510

Gly Val Thr Leu Tyr Glu Leu Leu Thr His Cys Asp Ser Ser Gln Ser
            515                 520                 525

Pro Pro Thr Lys Phe Leu Glu Leu Ile Gly Ile Ala Gln Gly Gln Met
530                 535                 540

Thr Val Leu Arg Leu Thr Glu Leu Leu Glu Arg Gly Glu Arg Leu Pro
545                 550                 555                 560

Arg Pro Asp Lys Cys Pro Cys Glu Val Tyr His Leu Met Lys Asn Cys
                565                 570                 575

Trp Glu Thr Glu Ala Ser Phe Arg Pro Thr Phe Glu Asn Leu Ile Pro
                580                 585                 590

Ile Leu Lys Thr Val His Glu Lys Tyr Gln Gly Gln Ala Pro Ser Val
            595                 600                 605

Phe Ser Val Cys Glu Phe Gly Ser Ser Pro Ile Ser Pro Ile Glu Thr
610                 615                 620

Val Pro Val Lys Leu Lys Pro Gly Met Asp Gly Pro Lys Val Lys Gln
625                 630                 635                 640

Trp Pro Leu Thr Glu Glu Lys Ile Lys Ala Leu Val Glu Ile Cys Thr
                645                 650                 655

Glu Met Glu Lys Glu Gly Lys Ile Ser Lys Ile Gly Pro Glu Asn Pro
                660                 665                 670

Tyr Asn Thr Pro Val Phe Ala Ile Lys Lys Lys Asp Ser Thr Lys Trp
            675                 680                 685

Arg Lys Leu Val Asp Phe Arg Glu Leu Asn Lys Arg Thr Gln Asp Phe
690                 695                 700

Trp Glu Val Gln Leu Gly Ile Pro His Pro Ala Gly Leu Lys Gln Lys
705                 710                 715                 720

Lys Ser Val Thr Val Leu Asp Val Gly Asp Ala Tyr Phe Ser Val Pro
                725                 730                 735

Leu Asp Lys Asp Phe Arg Lys Tyr Thr Ala Phe Thr Ile Pro Ser Ile
            740                 745                 750

Asn Asn Glu Thr Pro Gly Ile Arg Tyr Gln Tyr Asn Val Leu Pro Gln
            755                 760                 765

Gly Trp Lys Gly Ser Pro Ala Ile Phe Gln Cys Ser Met Thr Lys Ile
770                 775                 780

Leu Glu Pro Phe Arg Lys Gln Asn Pro Asp Ile Val Ile Tyr Gln Tyr
785                 790                 795                 800

Met Asp Asp Leu Tyr Val Gly Ser Asp Leu Glu Ile Gly Gln His Arg
                805                 810                 815

Thr Lys Ile Glu Glu Leu Arg Gln His Leu Leu Arg Trp Gly Phe Thr
            820                 825                 830

Thr Pro Asp Lys Lys His Gln Lys Glu Pro Pro Phe Leu Trp Met Gly
                835                 840                 845

Tyr Glu Leu His Pro Asp Lys Trp Thr Val Gln Pro Ile Val Leu Pro
850                 855                 860
```

```
Glu Lys Asp Ser Trp Thr Val Asn Asp Ile Gln Lys Leu Val Gly Lys
865                 870                 875                 880

Leu Asn Trp Ala Ser Gln Ile Tyr Ala Gly Ile Lys Val Arg Gln Leu
                885                 890                 895

Cys Lys Leu Leu Arg Gly Thr Lys Ala Leu Thr Glu Val Val Pro Leu
                900                 905                 910

Thr Glu Glu Ala Glu Leu Glu Leu Ala Glu Asn Arg Glu Ile Leu Lys
            915                 920                 925

Glu Pro Val His Gly Val Tyr Tyr Asp Pro Ser Lys Asp Leu Ile Ala
        930                 935                 940

Glu Ile Gln Lys Gln Gly Gln Gly Gln Trp Thr Tyr Gln Ile Tyr Gln
945                 950                 955                 960

Glu Pro Phe Lys Asn Leu Lys Thr Gly Lys Tyr Ala Arg Met Lys Gly
                965                 970                 975

Ala His Thr Asn Asp Val Lys Gln Leu Thr Glu Ala Val Gln Lys Ile
                980                 985                 990

Ala Thr Glu Ser Ile Val Ile Trp Gly Lys Thr Pro Lys Phe Lys Leu
            995                 1000                1005

Pro Ile Gln Lys Glu Thr Trp Glu Ala Trp Trp Thr Glu Tyr Trp
    1010                1015                1020

Gln Ala Thr Trp Ile Pro Glu Trp Glu Phe Val Asn Thr Pro Pro
    1025                1030                1035

Leu Val Lys Leu Trp Tyr Gln Leu Glu Lys Glu Pro Ile Ile Gly
    1040                1045                1050

Ala Glu Thr Phe Tyr Val Asp Gly Ala Ala Asn Arg Glu Thr Lys
    1055                1060                1065

Leu Gly Lys Ala Gly Tyr Val Thr Asp Arg Gly Arg Gln Lys Val
    1070                1075                1080

Val Pro Leu Thr Asp Thr Thr Asn Gln Lys Thr Glu Leu Gln Ala
    1085                1090                1095

Ile His Leu Ala Leu Gln Asp Ser Gly Leu Glu Val Asn Ile Val
    1100                1105                1110

Thr Asp Ser Gln Tyr Ala Leu Gly Ile Ile Gln Ala Gln Pro Asp
    1115                1120                1125

Lys Ser Glu Ser Glu Leu Val Ser Gln Ile Ile Glu Gln Leu Ile
    1130                1135                1140

Lys Lys Glu Lys Val Tyr Leu Ala Trp Val Pro Ala His Lys Gly
    1145                1150                1155

Ile Gly Gly Asn Glu Gln Val Asp Gly Leu Val Ser Ala Gly Ile
    1160                1165                1170

Arg Lys Val Leu
    1175

<210> SEQ ID NO 29
<211> LENGTH: 1245
<212> TYPE: PRT
<213> ORGANISM: Artificial Sequence
<220> FEATURE:
<223> OTHER INFORMATION: HA-Tyk2(C)-SERT construct

<400> SEQUENCE: 29

Met Tyr Pro Tyr Asp Val Pro Asp Tyr Ala Leu Ile Lys Ile Thr Gln
1               5                   10                  15

Leu Ser His Leu Gly Gln Gly Thr Arg Thr Asn Val Tyr Glu Gly Arg
            20                  25                  30
```

```
Leu Arg Val Glu Gly Ser Gly Asp Pro Glu Gly Lys Met Asp Asp
         35                  40                  45
Glu Asp Pro Leu Val Pro Gly Arg Asp Arg Gly Gln Glu Leu Arg Val
 50                  55                  60
Val Leu Lys Val Leu Asp Pro Ser His His Asp Ile Ala Leu Ala Phe
65                   70                  75                  80
Tyr Glu Thr Ala Ser Leu Met Ser Gln Val Ser His Thr His Leu Ala
                 85                  90                  95
Phe Val His Gly Val Cys Val Arg Gly Pro Glu Asn Ser Met Val Thr
             100                 105                 110
Glu Tyr Val Glu His Gly Pro Leu Asp Val Trp Leu Arg Arg Glu Arg
         115                 120                 125
Gly His Val Pro Met Ala Trp Lys Met Val Val Ala Gln Gln Leu Ala
130                 135                 140
Ser Ala Leu Ser Tyr Leu Glu Asn Lys Asn Leu Val His Gly Asn Val
145                 150                 155                 160
Cys Gly Arg Asn Ile Leu Leu Ala Arg Leu Gly Leu Ala Glu Gly Thr
                 165                 170                 175
Ser Pro Phe Ile Lys Leu Ser Asp Pro Gly Val Gly Leu Gly Ala Leu
             180                 185                 190
Ser Arg Glu Glu Arg Val Glu Arg Ile Pro Trp Leu Ala Pro Glu Cys
         195                 200                 205
Leu Pro Gly Gly Ala Asn Ser Leu Ser Thr Ala Met Asp Lys Trp Gly
210                 215                 220
Phe Gly Ala Thr Leu Leu Glu Ile Cys Phe Asp Gly Glu Ala Pro Leu
225                 230                 235                 240
Gln Ser Arg Ser Pro Ser Glu Lys Glu His Phe Tyr Gln Arg Gln His
                 245                 250                 255
Arg Leu Pro Glu Pro Ser Cys Pro Gln Leu Ala Thr Leu Thr Ser Gln
             260                 265                 270
Cys Leu Thr Tyr Glu Pro Thr Gln Arg Pro Ser Phe Arg Thr Ile Leu
         275                 280                 285
Arg Asp Leu Thr Arg Val Gln Pro His Asn Leu Ala Asp Val Leu Thr
290                 295                 300
Val Asn Arg Asp Ser Pro Ala Val Gly Pro Thr Thr Phe His Lys Arg
305                 310                 315                 320
Tyr Leu Lys Lys Ile Arg Asp Leu Gly Glu Gly His Phe Gly Lys Val
                 325                 330                 335
Ser Leu Tyr Cys Tyr Asp Pro Thr Asn Asp Gly Thr Gly Glu Met Val
             340                 345                 350
Ala Val Lys Ala Leu Lys Ala Asp Cys Gly Pro Gln His Arg Ser Gly
         355                 360                 365
Trp Lys Gln Glu Ile Asp Ile Leu Arg Thr Leu Tyr His Glu His Ile
370                 375                 380
Ile Lys Tyr Lys Gly Cys Cys Glu Asp Gln Gly Glu Lys Ser Leu Gln
385                 390                 395                 400
Leu Val Met Glu Tyr Val Pro Leu Gly Ser Leu Arg Asp Tyr Leu Pro
                 405                 410                 415
Arg His Ser Ile Gly Leu Ala Gln Leu Leu Phe Ala Gln Gln Ile
             420                 425                 430
Cys Glu Gly Met Ala Tyr Leu His Ala His Asp Tyr Ile His Arg Asp
         435                 440                 445
Leu Ala Ala Arg Asn Val Leu Leu Asp Asn Asp Arg Leu Val Lys Ile
```

```
                450             455             460
Gly Asp Phe Gly Leu Ala Lys Ala Val Pro Glu Gly His Glu Tyr Tyr
465                 470                 475                 480

Arg Val Arg Glu Asp Gly Asp Ser Pro Val Phe Trp Tyr Ala Pro Glu
                485                 490                 495

Cys Leu Lys Glu Tyr Lys Phe Tyr Tyr Ala Ser Asp Val Trp Ser Phe
            500                 505                 510

Gly Val Thr Leu Tyr Glu Leu Leu Thr His Cys Asp Ser Ser Gln Ser
            515                 520                 525

Pro Pro Thr Lys Phe Leu Glu Leu Ile Gly Ile Ala Gln Gly Gln Met
        530                 535                 540

Thr Val Leu Arg Leu Thr Glu Leu Leu Glu Arg Gly Glu Arg Leu Pro
545                 550                 555                 560

Arg Pro Asp Lys Cys Pro Cys Glu Val Tyr His Leu Met Lys Asn Cys
                565                 570                 575

Trp Glu Thr Glu Ala Ser Phe Arg Pro Thr Phe Glu Asn Leu Ile Pro
            580                 585                 590

Ile Leu Lys Thr Val His Glu Lys Tyr Gln Gly Gln Ala Pro Ser Val
            595                 600                 605

Phe Ser Val Cys Glu Leu Ser Met Glu Thr Thr Pro Leu Asn Ser Gln
        610                 615                 620

Lys Gln Leu Ser Ala Cys Glu Asp Gly Glu Asp Cys Gln Glu Asn Gly
625                 630                 635                 640

Val Leu Gln Lys Val Val Pro Thr Pro Gly Asp Lys Val Glu Ser Gly
                645                 650                 655

Gln Ile Ser Asn Gly Tyr Ser Ala Val Pro Ser Pro Gly Ala Gly Asp
            660                 665                 670

Asp Thr Arg His Ser Ile Pro Ala Thr Thr Thr Leu Val Ala Glu
            675                 680                 685

Leu His Gln Gly Glu Arg Glu Thr Trp Gly Lys Lys Val Asp Phe Leu
        690                 695                 700

Leu Ser Val Ile Gly Tyr Ala Val Asp Leu Gly Asn Val Trp Arg Phe
705                 710                 715                 720

Pro Tyr Ile Cys Tyr Gln Asn Gly Gly Ala Phe Leu Leu Pro Tyr
                725                 730                 735

Thr Ile Met Ala Ile Phe Gly Gly Ile Pro Leu Phe Tyr Met Glu Leu
            740                 745                 750

Ala Leu Gly Gln Tyr His Arg Asn Gly Cys Ile Ser Ile Trp Arg Lys
            755                 760                 765

Ile Cys Pro Ile Phe Lys Gly Ile Gly Tyr Ala Ile Cys Ile Ile Ala
        770                 775                 780

Phe Tyr Ile Ala Ser Tyr Tyr Asn Thr Ile Met Ala Trp Ala Leu Tyr
785                 790                 795                 800

Tyr Leu Ile Ser Ser Phe Thr Asp Gln Leu Pro Trp Thr Ser Cys Lys
                805                 810                 815

Asn Ser Trp Asn Thr Gly Asn Cys Thr Asn Tyr Phe Ser Glu Asp Asn
            820                 825                 830

Ile Thr Trp Thr Leu His Ser Thr Ser Pro Ala Glu Glu Phe Tyr Thr
            835                 840                 845

Arg His Val Leu Gln Ile His Arg Ser Lys Gly Leu Gln Asp Leu Gly
        850                 855                 860

Gly Ile Ser Trp Gln Leu Ala Leu Cys Ile Met Leu Ile Phe Thr Val
865                 870                 875                 880
```

Ile Tyr Phe Ser Ile Trp Lys Gly Val Lys Thr Ser Gly Lys Val Val
               885                 890                 895

Trp Val Thr Ala Thr Phe Pro Tyr Ile Ile Leu Ser Val Leu Leu Val
            900                 905                 910

Arg Gly Ala Thr Leu Pro Gly Ala Trp Arg Gly Val Leu Phe Tyr Leu
            915                 920                 925

Lys Pro Asn Trp Gln Lys Leu Leu Glu Thr Gly Val Trp Ile Asp Ala
            930                 935                 940

Ala Ala Gln Ile Phe Phe Ser Leu Gly Pro Gly Phe Gly Val Leu Leu
945                 950                 955                 960

Ala Phe Ala Ser Tyr Asn Lys Phe Asn Asn Asn Cys Tyr Gln Asp Ala
                965                 970                 975

Leu Val Thr Ser Val Val Asn Cys Met Thr Ser Phe Val Ser Gly Phe
            980                 985                 990

Val Ile Phe Thr Val Leu Gly Tyr Met Ala Glu Met Arg Asn Glu Asp
            995                 1000                1005

Val Ser Glu Val Ala Lys Asp Ala Gly Pro Ser Leu Leu Phe Ile
        1010                1015                1020

Thr Tyr Ala Glu Ala Ile Ala Asn Met Pro Ala Ser Thr Phe Phe
        1025                1030                1035

Ala Ile Ile Phe Phe Leu Met Leu Ile Thr Leu Gly Leu Asp Ser
        1040                1045                1050

Thr Phe Ala Gly Leu Glu Gly Val Ile Thr Ala Val Leu Asp Glu
        1055                1060                1065

Phe Pro His Val Trp Ala Lys Arg Arg Glu Arg Phe Val Leu Ala
        1070                1075                1080

Val Val Ile Thr Cys Phe Phe Gly Ser Leu Val Thr Leu Thr Phe
        1085                1090                1095

Gly Gly Ala Tyr Val Val Lys Leu Leu Glu Glu Tyr Ala Thr Gly
        1100                1105                1110

Pro Ala Val Leu Thr Val Ala Leu Ile Glu Ala Val Ala Val Ser
        1115                1120                1125

Trp Phe Tyr Gly Ile Thr Gln Phe Cys Arg Asp Val Lys Glu Met
        1130                1135                1140

Leu Gly Phe Ser Pro Gly Trp Phe Trp Arg Ile Cys Trp Val Ala
        1145                1150                1155

Ile Ser Pro Leu Phe Leu Leu Phe Ile Ile Cys Ser Phe Leu Met
        1160                1165                1170

Ser Pro Pro Gln Leu Arg Leu Phe Gln Tyr Asn Tyr Pro Tyr Trp
        1175                1180                1185

Ser Ile Ile Leu Gly Tyr Cys Ile Gly Thr Ser Ser Phe Ile Cys
        1190                1195                1200

Ile Pro Thr Tyr Ile Ala Tyr Arg Leu Ile Ile Thr Pro Gly Thr
        1205                1210                1215

Phe Lys Glu Arg Ile Ile Lys Ser Ile Thr Pro Glu Thr Pro Thr
        1220                1225                1230

Glu Ile Pro Cys Gly Asp Ile Arg Leu Asn Ala Val
        1235                1240                1245

<210> SEQ ID NO 30
<211> LENGTH: 1593
<212> TYPE: PRT
<213> ORGANISM: Artificial Sequence
<220> FEATURE:

<223> OTHER INFORMATION: ERN1(K599A)-Tyk2(C)-HA fusion protein

<400> SEQUENCE: 30

```
Met Pro Ala Arg Arg Leu Leu Leu Leu Thr Leu Leu Leu Pro Gly
1               5                   10                  15

Leu Gly Ile Phe Gly Ser Thr Ser Thr Val Thr Leu Pro Glu Thr Leu
            20                  25                  30

Leu Phe Val Ser Thr Leu Asp Gly Ser Leu His Ala Val Ser Lys Arg
        35                  40                  45

Thr Gly Ser Ile Lys Trp Thr Leu Lys Glu Asp Pro Val Leu Gln Val
    50                  55                  60

Pro Thr His Val Glu Glu Pro Ala Phe Leu Pro Asp Pro Asn Asp Gly
65                  70                  75                  80

Ser Leu Tyr Thr Leu Gly Ser Lys Asn Asn Glu Gly Leu Thr Lys Leu
                85                  90                  95

Pro Phe Thr Ile Pro Glu Leu Val Gln Ala Ser Pro Cys Arg Ser Ser
            100                 105                 110

Asp Gly Ile Leu Tyr Met Gly Lys Lys Gln Asp Ile Trp Tyr Val Ile
        115                 120                 125

Asp Leu Leu Thr Gly Glu Lys Gln Gln Thr Leu Ser Ser Ala Phe Ala
130                 135                 140

Asp Ser Leu Cys Pro Ser Thr Ser Leu Leu Tyr Leu Gly Arg Thr Glu
145                 150                 155                 160

Tyr Thr Ile Thr Met Tyr Asp Thr Lys Thr Arg Glu Leu Arg Trp Asn
                165                 170                 175

Ala Thr Tyr Phe Asp Tyr Ala Ala Ser Leu Pro Glu Asp Asp Val Asp
            180                 185                 190

Tyr Lys Met Ser His Phe Val Ser Asn Gly Asp Gly Leu Val Val Thr
        195                 200                 205

Val Asp Ser Glu Ser Gly Asp Val Leu Trp Ile Gln Asn Tyr Ala Ser
210                 215                 220

Pro Val Val Ala Phe Tyr Val Trp Gln Arg Glu Gly Leu Arg Lys Val
225                 230                 235                 240

Met His Ile Asn Val Ala Val Glu Thr Leu Arg Tyr Leu Thr Phe Met
                245                 250                 255

Ser Gly Glu Val Gly Arg Ile Thr Lys Trp Lys Tyr Pro Phe Pro Lys
            260                 265                 270

Glu Thr Glu Ala Lys Ser Lys Leu Thr Pro Thr Leu Tyr Val Gly Lys
        275                 280                 285

Tyr Ser Thr Ser Leu Tyr Ala Ser Pro Ser Met Val His Glu Gly Val
    290                 295                 300

Ala Val Val Pro Arg Gly Ser Thr Leu Pro Leu Leu Glu Gly Pro Gln
305                 310                 315                 320

Thr Asp Gly Val Thr Ile Gly Asp Lys Gly Glu Cys Val Ile Thr Pro
                325                 330                 335

Ser Thr Asp Val Lys Phe Asp Pro Gly Leu Lys Ser Lys Asn Lys Leu
            340                 345                 350

Asn Tyr Leu Arg Asn Tyr Trp Leu Leu Ile Gly His His Glu Thr Pro
        355                 360                 365

Leu Ser Ala Ser Thr Lys Met Leu Glu Arg Phe Pro Asn Asn Leu Pro
    370                 375                 380

Lys His Arg Glu Asn Val Ile Pro Ala Asp Ser Glu Lys Lys Ser Phe
385                 390                 395                 400
```

```
Glu Glu Val Ile Asn Leu Val Asp Gln Thr Ser Glu Asn Ala Pro Thr
                405                 410                 415
Thr Val Ser Arg Asp Val Glu Glu Lys Pro Ala His Ala Pro Ala Arg
            420                 425                 430
Pro Glu Ala Pro Val Asp Ser Met Leu Lys Asp Met Ala Thr Ile Ile
        435                 440                 445
Leu Ser Thr Phe Leu Leu Ile Gly Trp Val Ala Phe Ile Ile Thr Tyr
450                 455                 460
Pro Leu Ser Met His Gln Gln Gln Leu Gln His Gln Gln Phe Gln
465                 470                 475                 480
Lys Glu Leu Glu Lys Ile Gln Leu Leu Gln Gln Gln Gln Gln Leu
                485                 490                 495
Pro Phe His Pro Pro Gly Asp Thr Ala Gln Asp Gly Glu Leu Leu Asp
            500                 505                 510
Thr Ser Gly Pro Tyr Ser Glu Ser Ser Gly Thr Ser Ser Pro Ser Thr
        515                 520                 525
Ser Pro Arg Ala Ser Asn His Ser Leu Cys Ser Gly Ser Ser Ala Ser
    530                 535                 540
Lys Ala Gly Ser Ser Pro Ser Leu Glu Gln Asp Asp Gly Asp Glu Glu
545                 550                 555                 560
Thr Ser Val Val Ile Val Gly Lys Ile Ser Phe Cys Pro Lys Asp Val
                565                 570                 575
Leu Gly His Gly Ala Glu Gly Thr Ile Val Tyr Arg Gly Met Phe Asp
            580                 585                 590
Asn Arg Asp Val Ala Val Ala Arg Ile Leu Pro Glu Cys Phe Ser Phe
        595                 600                 605
Ala Asp Arg Glu Val Gln Leu Leu Arg Glu Ser Asp Glu His Pro Asn
    610                 615                 620
Val Ile Arg Tyr Phe Cys Thr Glu Lys Asp Arg Gln Phe Gln Tyr Ile
625                 630                 635                 640
Ala Ile Glu Leu Cys Ala Ala Thr Leu Gln Glu Tyr Val Glu Gln Lys
                645                 650                 655
Asp Phe Ala His Leu Gly Leu Glu Pro Ile Thr Leu Leu Gln Gln Thr
            660                 665                 670
Thr Ser Gly Leu Ala His Leu His Ser Leu Asn Ile Val His Arg Asp
        675                 680                 685
Leu Lys Pro His Asn Ile Leu Ile Ser Met Pro Asn Ala His Gly Lys
    690                 695                 700
Ile Lys Ala Met Ile Ser Asp Phe Gly Leu Cys Lys Lys Leu Ala Val
705                 710                 715                 720
Gly Arg His Ser Phe Ser Arg Arg Ser Gly Val Pro Gly Thr Glu Gly
                725                 730                 735
Trp Ile Ala Pro Glu Met Leu Ser Glu Asp Cys Lys Glu Asn Pro Thr
            740                 745                 750
Tyr Thr Val Asp Ile Phe Ser Ala Gly Cys Val Phe Tyr Tyr Val Ile
        755                 760                 765
Ser Glu Gly Ser His Pro Phe Gly Lys Ser Leu Gln Arg Gln Ala Asn
    770                 775                 780
Ile Leu Leu Gly Ala Cys Ser Leu Asp Cys Leu His Pro Glu Lys His
785                 790                 795                 800
Glu Asp Val Ile Ala Arg Glu Leu Ile Glu Lys Met Ile Ala Met Asp
                805                 810                 815
Pro Gln Lys Arg Pro Ser Ala Lys His Val Leu Lys His Pro Phe Phe
```

```
                820             825             830
Trp Ser Leu Glu Lys Gln Leu Gln Phe Phe Gln Asp Val Ser Asp Arg
            835             840             845
Ile Glu Lys Glu Ser Leu Asp Gly Pro Ile Val Lys Gln Leu Glu Arg
850             855             860
Gly Gly Arg Ala Val Val Lys Met Asp Trp Arg Glu Asn Ile Thr Val
865             870             875             880
Pro Leu Gln Thr Asp Leu Arg Lys Phe Arg Thr Tyr Lys Gly Gly Ser
            885             890             895
Val Arg Asp Leu Leu Arg Ala Met Arg Asn Lys Lys His His Tyr Arg
            900             905             910
Glu Leu Pro Ala Glu Val Arg Glu Thr Leu Gly Ser Leu Pro Asp Asp
            915             920             925
Phe Val Cys Tyr Phe Thr Ser Arg Phe Pro His Leu Leu Ala His Thr
            930             935             940
Tyr Arg Ala Met Glu Leu Cys Ser His Glu Arg Leu Phe Gln Pro Tyr
945             950             955             960
Tyr Phe His Glu Pro Pro Glu Pro Gln Pro Pro Val Thr Pro Asp Ala
            965             970             975
Leu Ala Ala Ala Gly Gly Ser Ile Thr Gln Leu Ser His Leu Gly Gln
            980             985             990
Gly Thr Arg Thr Asn Val Tyr Glu  Gly Arg Leu Arg Val  Glu Gly Ser
            995             1000            1005
Gly Asp  Pro Glu Glu Gly Lys  Met Asp Asp Glu Asp  Pro Leu Val
    1010            1015            1020
Pro Gly  Arg Asp Arg Gly Gln  Glu Leu Arg Val Val  Leu Lys Val
    1025            1030            1035
Leu Asp  Pro Ser His His Asp  Ile Ala Leu Ala Phe  Tyr Glu Thr
    1040            1045            1050
Ala Ser  Leu Met Ser Gln Val  Ser His Thr His Leu  Ala Phe Val
    1055            1060            1065
His Gly  Val Cys Val Arg Gly  Pro Glu Asn Ser Met  Val Thr Glu
    1070            1075            1080
Tyr Val  Glu His Gly Pro Leu  Asp Val Trp Leu Arg  Arg Glu Arg
    1085            1090            1095
Gly His  Val Pro Met Ala Trp  Lys Met Val Val Ala  Gln Gln Leu
    1100            1105            1110
Ala Ser  Ala Leu Ser Tyr Leu  Glu Asn Lys Asn Leu  Val His Gly
    1115            1120            1125
Asn Val  Cys Gly Arg Asn Ile  Leu Leu Ala Arg Leu  Gly Leu Ala
    1130            1135            1140
Glu Gly  Thr Ser Pro Phe Ile  Lys Leu Ser Asp Pro  Gly Val Gly
    1145            1150            1155
Leu Gly  Ala Leu Ser Arg Glu  Glu Arg Val Glu Arg  Ile Pro Trp
    1160            1165            1170
Leu Ala  Pro Glu Cys Leu Pro  Gly Gly Ala Asn Ser  Leu Ser Thr
    1175            1180            1185
Ala Met  Asp Lys Trp Gly Phe  Gly Ala Thr Leu Leu  Glu Ile Cys
    1190            1195            1200
Phe Asp  Gly Glu Ala Pro Leu  Gln Ser Arg Ser Pro  Ser Glu Lys
    1205            1210            1215
Glu His  Phe Tyr Gln Arg Gln  His Arg Leu Pro Glu  Pro Ser Cys
    1220            1225            1230
```

Pro Gln Leu Ala Thr Leu Thr Ser Gln Cys Leu Thr Tyr Glu Pro
    1235                1240                1245

Thr Gln Arg Pro Ser Phe Arg Thr Ile Leu Arg Asp Leu Thr Arg
    1250                1255                1260

Val Gln Pro His Asn Leu Ala Asp Val Leu Thr Val Asn Arg Asp
    1265                1270                1275

Ser Pro Ala Val Gly Pro Thr Phe His Lys Arg Tyr Leu Lys
    1280                1285                1290

Lys Ile Arg Asp Leu Gly Glu Gly His Phe Gly Lys Val Ser Leu
    1295                1300                1305

Tyr Cys Tyr Asp Pro Thr Asn Asp Gly Thr Gly Glu Met Val Ala
    1310                1315                1320

Val Lys Ala Leu Lys Ala Asp Cys Gly Pro Gln His Arg Ser Gly
    1325                1330                1335

Trp Lys Gln Glu Ile Asp Ile Leu Arg Thr Leu Tyr His Glu His
    1340                1345                1350

Ile Ile Lys Tyr Lys Gly Cys Cys Glu Asp Gln Gly Glu Lys Ser
    1355                1360                1365

Leu Gln Leu Val Met Glu Tyr Val Pro Leu Gly Ser Leu Arg Asp
    1370                1375                1380

Tyr Leu Pro Arg His Ser Ile Gly Leu Ala Gln Leu Leu Leu Phe
    1385                1390                1395

Ala Gln Gln Ile Cys Glu Gly Met Ala Tyr Leu His Ala His Asp
    1400                1405                1410

Tyr Ile His Arg Asp Leu Ala Ala Arg Asn Val Leu Leu Asp Asn
    1415                1420                1425

Asp Arg Leu Val Lys Ile Gly Asp Phe Gly Leu Ala Lys Ala Val
    1430                1435                1440

Pro Glu Gly His Glu Tyr Tyr Arg Val Arg Glu Asp Gly Asp Ser
    1445                1450                1455

Pro Val Phe Trp Tyr Ala Pro Glu Cys Leu Lys Glu Tyr Lys Phe
    1460                1465                1470

Tyr Tyr Ala Ser Asp Val Trp Ser Phe Gly Val Thr Leu Tyr Glu
    1475                1480                1485

Leu Leu Thr His Cys Asp Ser Ser Gln Ser Pro Pro Thr Lys Phe
    1490                1495                1500

Leu Glu Leu Ile Gly Ile Ala Gln Gly Gln Met Thr Val Leu Arg
    1505                1510                1515

Leu Thr Glu Leu Leu Glu Arg Gly Glu Arg Leu Pro Arg Pro Asp
    1520                1525                1530

Lys Cys Pro Cys Glu Val Tyr His Leu Met Lys Asn Cys Trp Glu
    1535                1540                1545

Thr Glu Ala Ser Phe Arg Pro Thr Phe Glu Asn Leu Ile Pro Ile
    1550                1555                1560

Leu Lys Thr Val His Glu Lys Tyr Gln Gly Gln Ala Pro Ser Val
    1565                1570                1575

Phe Ser Val Cys Leu Glu Tyr Pro Tyr Asp Val Pro Asp Tyr Ala
    1580                1585                1590

<210> SEQ ID NO 31
<211> LENGTH: 1595
<212> TYPE: PRT
<213> ORGANISM: Artificial Sequence
<220> FEATURE:

<223> OTHER INFORMATION: ERN1(D123P)-Tyk2(K)-HA fusion protein

<400> SEQUENCE: 31

```
Met Pro Ala Arg Arg Leu Leu Leu Leu Thr Leu Leu Pro Gly
1               5                   10                  15
Leu Gly Ile Phe Gly Ser Thr Ser Thr Val Thr Leu Pro Glu Thr Leu
            20                  25                  30
Leu Phe Val Ser Thr Leu Asp Gly Ser Leu His Ala Val Ser Lys Arg
        35                  40                  45
Thr Gly Ser Ile Lys Trp Thr Leu Lys Glu Asp Pro Val Leu Gln Val
    50                  55                  60
Pro Thr His Val Glu Glu Pro Ala Phe Leu Pro Asp Pro Asn Asp Gly
65                  70                  75                  80
Ser Leu Tyr Thr Leu Gly Ser Lys Asn Asn Glu Gly Leu Thr Lys Leu
                85                  90                  95
Pro Phe Thr Ile Pro Glu Leu Val Gln Ala Ser Pro Cys Arg Ser Ser
            100                 105                 110
Asp Gly Ile Leu Tyr Met Gly Lys Lys Gln Pro Ile Trp Tyr Val Ile
        115                 120                 125
Asp Leu Leu Thr Gly Glu Lys Gln Gln Thr Leu Ser Ser Ala Phe Ala
    130                 135                 140
Asp Ser Leu Cys Pro Ser Thr Ser Leu Leu Tyr Leu Gly Arg Thr Glu
145                 150                 155                 160
Tyr Thr Ile Thr Met Tyr Asp Thr Lys Thr Arg Glu Leu Arg Trp Asn
                165                 170                 175
Ala Thr Tyr Phe Asp Tyr Ala Ala Ser Leu Pro Glu Asp Asp Val Asp
            180                 185                 190
Tyr Lys Met Ser His Phe Val Ser Asn Gly Asp Gly Leu Val Val Thr
        195                 200                 205
Val Asp Ser Glu Ser Gly Asp Val Leu Trp Ile Gln Asn Tyr Ala Ser
    210                 215                 220
Pro Val Val Ala Phe Tyr Val Trp Gln Arg Glu Gly Leu Arg Lys Val
225                 230                 235                 240
Met His Ile Asn Val Ala Val Glu Thr Leu Arg Tyr Leu Thr Phe Met
                245                 250                 255
Ser Gly Glu Val Gly Arg Ile Thr Lys Trp Lys Tyr Pro Phe Pro Lys
            260                 265                 270
Glu Thr Glu Ala Lys Ser Lys Leu Thr Pro Thr Leu Tyr Val Gly Lys
        275                 280                 285
Tyr Ser Thr Ser Leu Tyr Ala Ser Pro Ser Met Val His Glu Gly Val
    290                 295                 300
Ala Val Val Pro Arg Gly Ser Thr Leu Pro Leu Leu Glu Gly Pro Gln
305                 310                 315                 320
Thr Asp Gly Val Thr Ile Gly Asp Lys Gly Glu Cys Val Ile Thr Pro
                325                 330                 335
Ser Thr Asp Val Lys Phe Asp Pro Gly Leu Lys Ser Lys Asn Lys Leu
            340                 345                 350
Asn Tyr Leu Arg Asn Tyr Trp Leu Leu Ile Gly His His Glu Thr Pro
        355                 360                 365
Leu Ser Ala Ser Thr Lys Met Leu Glu Arg Phe Pro Asn Asn Leu Pro
    370                 375                 380
Lys His Arg Glu Asn Val Ile Pro Ala Asp Ser Glu Lys Lys Ser Phe
385                 390                 395                 400
```

```
Glu Glu Val Ile Asn Leu Val Asp Gln Thr Ser Glu Asn Ala Pro Thr
                405                 410                 415
Thr Val Ser Arg Asp Val Glu Glu Lys Pro Ala His Ala Pro Ala Arg
            420                 425                 430
Pro Glu Ala Pro Val Asp Ser Met Leu Lys Asp Met Ala Thr Ile Ile
        435                 440                 445
Leu Ser Thr Phe Leu Leu Ile Gly Trp Val Ala Phe Ile Ile Thr Tyr
    450                 455                 460
Pro Leu Ser Met His Gln Gln Gln Leu Gln His Gln Gln Phe Gln
465                 470                 475                 480
Lys Glu Leu Glu Lys Ile Gln Leu Leu Gln Gln Gln Gln Gln Leu
                485                 490                 495
Pro Phe His Pro Pro Gly Asp Thr Ala Gln Asp Gly Glu Leu Leu Asp
            500                 505                 510
Thr Ser Gly Pro Tyr Ser Glu Ser Ser Gly Thr Ser Ser Pro Ser Thr
        515                 520                 525
Ser Pro Arg Ala Ser Asn His Ser Leu Cys Ser Gly Ser Ser Ala Ser
    530                 535                 540
Lys Ala Gly Ser Ser Pro Ser Leu Glu Gln Asp Asp Gly Asp Glu Glu
545                 550                 555                 560
Thr Ser Val Val Ile Val Gly Lys Ile Ser Phe Cys Pro Lys Asp Val
                565                 570                 575
Leu Gly His Gly Ala Glu Gly Thr Ile Val Tyr Arg Gly Met Phe Asp
            580                 585                 590
Asn Arg Asp Val Ala Val Lys Arg Ile Leu Pro Glu Cys Phe Ser Phe
        595                 600                 605
Ala Asp Arg Glu Val Gln Leu Leu Arg Glu Ser Asp Glu His Pro Asn
    610                 615                 620
Val Ile Arg Tyr Phe Cys Thr Glu Lys Asp Arg Gln Phe Gln Tyr Ile
625                 630                 635                 640
Ala Ile Glu Leu Cys Ala Ala Thr Leu Gln Glu Tyr Val Glu Gln Lys
                645                 650                 655
Asp Phe Ala His Leu Gly Leu Glu Pro Ile Thr Leu Leu Gln Gln Thr
            660                 665                 670
Thr Ser Gly Leu Ala His Leu His Ser Leu Asn Ile Val His Arg Asp
        675                 680                 685
Leu Lys Pro His Asn Ile Leu Ile Ser Met Pro Asn Ala His Gly Lys
    690                 695                 700
Ile Lys Ala Met Ile Ser Asp Phe Gly Leu Cys Lys Lys Leu Ala Val
705                 710                 715                 720
Gly Arg His Ser Phe Ser Arg Arg Ser Gly Val Pro Gly Thr Glu Gly
                725                 730                 735
Trp Ile Ala Pro Glu Met Leu Ser Glu Asp Cys Lys Glu Asn Pro Thr
            740                 745                 750
Tyr Thr Val Asp Ile Phe Ser Ala Gly Cys Val Phe Tyr Tyr Val Ile
        755                 760                 765
Ser Glu Gly Ser His Pro Phe Gly Lys Ser Leu Gln Arg Gln Ala Asn
    770                 775                 780
Ile Leu Leu Gly Ala Cys Ser Leu Asp Cys Leu His Pro Glu Lys His
785                 790                 795                 800
Glu Asp Val Ile Ala Arg Glu Leu Ile Glu Lys Met Ile Ala Met Asp
                805                 810                 815
Pro Gln Lys Arg Pro Ser Ala Lys His Val Leu Lys His Pro Phe Phe
```

-continued

```
              820                825                830
Trp Ser Leu Glu Lys Gln Leu Gln Phe Phe Gln Asp Val Ser Asp Arg
              835                840                845
Ile Glu Lys Glu Ser Leu Asp Gly Pro Ile Val Lys Gln Leu Glu Arg
              850                855                860
Gly Gly Arg Ala Val Val Lys Met Asp Trp Arg Glu Asn Ile Thr Val
865                870                875                880
Pro Leu Gln Thr Asp Leu Arg Lys Phe Arg Thr Tyr Lys Gly Gly Ser
              885                890                895
Val Arg Asp Leu Leu Arg Ala Met Arg Asn Lys Lys His His Tyr Arg
              900                905                910
Glu Leu Pro Ala Glu Val Arg Glu Thr Leu Gly Ser Leu Pro Asp Asp
              915                920                925
Phe Val Cys Tyr Phe Thr Ser Arg Phe Pro His Leu Leu Ala His Thr
              930                935                940
Tyr Arg Ala Met Glu Leu Cys Ser His Glu Arg Leu Phe Gln Pro Tyr
945                950                955                960
Tyr Phe His Glu Pro Pro Glu Pro Gln Pro Val Thr Pro Asp Ala
              965                970                975
Leu Ala Ser Ala Ala Ala Gly Gly Ser Ile Thr Gln Leu Ser His Leu
              980                985                990
Gly Gln Gly Thr Arg Thr Asn Val Tyr Glu Gly Arg Leu Arg Val Glu
              995                1000               1005
Gly Ser Gly Asp Pro Glu Glu Gly Lys Met Asp Asp Glu Asp Pro
              1010               1015               1020
Leu Val Pro Gly Arg Asp Arg Gly Gln Glu Leu Arg Val Val Leu
              1025               1030               1035
Lys Val Leu Asp Pro Ser His His Asp Ile Ala Leu Ala Phe Tyr
              1040               1045               1050
Glu Thr Ala Ser Leu Met Ser Gln Val Ser His Thr His Leu Ala
              1055               1060               1065
Phe Val His Gly Val Cys Val Arg Gly Pro Glu Asn Ser Met Val
              1070               1075               1080
Thr Glu Tyr Val Glu His Gly Pro Leu Asp Val Trp Leu Arg Arg
              1085               1090               1095
Glu Arg Gly His Val Pro Met Ala Trp Lys Met Val Val Ala Gln
              1100               1105               1110
Gln Leu Ala Ser Ala Leu Ser Tyr Leu Glu Asn Lys Asn Leu Val
              1115               1120               1125
His Gly Asn Val Cys Gly Arg Asn Ile Leu Leu Ala Arg Leu Gly
              1130               1135               1140
Leu Ala Glu Gly Thr Ser Pro Phe Ile Lys Leu Ser Asp Pro Gly
              1145               1150               1155
Val Gly Leu Gly Ala Leu Ser Arg Glu Glu Arg Val Glu Arg Ile
              1160               1165               1170
Pro Trp Leu Ala Pro Glu Cys Leu Pro Gly Gly Ala Asn Ser Leu
              1175               1180               1185
Ser Thr Ala Met Asp Lys Trp Gly Phe Gly Ala Thr Leu Leu Glu
              1190               1195               1200
Ile Cys Phe Asp Gly Glu Ala Pro Leu Gln Ser Arg Ser Pro Ser
              1205               1210               1215
Glu Lys Glu His Phe Tyr Gln Arg Gln His Arg Leu Pro Glu Pro
              1220               1225               1230
```

Ser Cys Pro Gln Leu Ala Thr Leu Thr Ser Gln Cys Leu Thr Tyr
1235                1240                1245

Glu Pro Thr Gln Arg Pro Ser Phe Arg Thr Ile Leu Arg Asp Leu
1250                1255                1260

Thr Arg Val Gln Pro His Asn Leu Ala Asp Val Leu Thr Val Asn
1265                1270                1275

Arg Asp Ser Pro Ala Val Gly Pro Thr Thr Phe His Lys Arg Tyr
1280                1285                1290

Leu Lys Lys Ile Arg Asp Leu Gly Glu Gly His Phe Gly Lys Val
1295                1300                1305

Ser Leu Tyr Cys Tyr Asp Pro Thr Asn Asp Gly Thr Gly Glu Met
1310                1315                1320

Val Ala Val Lys Ala Leu Lys Ala Asp Cys Gly Pro Gln His Arg
1325                1330                1335

Ser Gly Trp Lys Gln Glu Ile Asp Ile Leu Arg Thr Leu Tyr His
1340                1345                1350

Glu His Ile Ile Lys Tyr Lys Gly Cys Cys Glu Asp Gln Gly Glu
1355                1360                1365

Lys Ser Leu Gln Leu Val Met Glu Tyr Val Pro Leu Gly Ser Leu
1370                1375                1380

Arg Asp Tyr Leu Pro Arg His Ser Ile Gly Leu Ala Gln Leu Leu
1385                1390                1395

Leu Phe Ala Gln Gln Ile Cys Glu Gly Met Ala Tyr Leu His Ala
1400                1405                1410

His Asp Tyr Ile His Arg Asp Leu Ala Ala Arg Asn Val Leu Leu
1415                1420                1425

Asp Asn Asp Arg Leu Val Lys Ile Gly Asp Phe Gly Leu Ala Lys
1430                1435                1440

Ala Val Pro Glu Gly His Glu Tyr Tyr Arg Val Arg Glu Asp Gly
1445                1450                1455

Asp Ser Pro Val Phe Trp Tyr Ala Pro Glu Cys Leu Lys Glu Tyr
1460                1465                1470

Lys Phe Tyr Tyr Ala Ser Asp Val Trp Ser Phe Gly Val Thr Leu
1475                1480                1485

Tyr Glu Leu Leu Thr His Cys Asp Ser Ser Gln Ser Pro Pro Thr
1490                1495                1500

Lys Phe Leu Glu Leu Ile Gly Ile Ala Gln Gly Gln Met Thr Val
1505                1510                1515

Leu Arg Leu Thr Glu Leu Leu Glu Arg Gly Glu Arg Leu Pro Arg
1520                1525                1530

Pro Asp Lys Cys Pro Cys Glu Val Tyr His Leu Met Lys Asn Cys
1535                1540                1545

Trp Glu Thr Glu Ala Ser Phe Arg Pro Thr Phe Glu Asn Leu Ile
1550                1555                1560

Pro Ile Leu Lys Thr Val His Glu Lys Tyr Gln Gly Gln Ala Pro
1565                1570                1575

Ser Val Phe Ser Val Cys Leu Glu Tyr Pro Tyr Asp Val Pro Asp
1580                1585                1590

Tyr Ala
1595

<210> SEQ ID NO 32
<211> LENGTH: 309

```
<212> TYPE: PRT
<213> ORGANISM: Artificial Sequence
<220> FEATURE:
<223> OTHER INFORMATION: flag tag-gp130-VAMP1 construct

<400> SEQUENCE: 32

Met Asp Tyr Lys Asp Asp Asp Lys Ile Ser Thr Val Val His Ser
1               5                   10                  15

Gly Tyr Arg His Gln Val Pro Ser Val Gln Val Phe Ser Arg Ser Glu
            20                  25                  30

Ser Thr Gln Pro Leu Leu Asp Ser Glu Glu Arg Pro Glu Asp Leu Gln
        35                  40                  45

Leu Val Asp His Val Asp Gly Gly Asp Gly Ile Leu Pro Arg Gln Gln
    50                  55                  60

Tyr Phe Lys Gln Asn Cys Ser Gln His Glu Ser Ser Pro Asp Ile Ser
65                  70                  75                  80

His Phe Glu Arg Ser Lys Gln Val Ser Val Asn Glu Glu Asp Phe
                85                  90                  95

Val Arg Leu Lys Gln Gln Ile Ser Asp His Ile Ser Gln Ser Cys Gly
                100                 105                 110

Ser Gly Gln Met Lys Met Phe Gln Glu Val Ser Ala Ala Asp Ala Phe
            115                 120                 125

Gly Pro Gly Thr Glu Gly Gln Val Glu Arg Phe Glu Thr Val Gly Met
130                 135                 140

Glu Ala Ala Thr Asp Glu Gly Met Pro Lys Ser Tyr Leu Pro Gln Thr
145                 150                 155                 160

Val Arg Gln Gly Gly Tyr Met Pro Gln Gly Gly Ser Glu Leu Ser Thr
                165                 170                 175

Ser Leu Tyr Lys Lys Val Gly Met Ser Ala Pro Ala Gln Pro Pro Ala
            180                 185                 190

Glu Gly Thr Glu Gly Thr Ala Pro Gly Gly Pro Gly Pro Pro
        195                 200                 205

Pro Asn Met Thr Ser Asn Arg Arg Leu Gln Gln Thr Gln Ala Gln Val
        210                 215                 220

Glu Glu Val Val Asp Ile Ile Arg Val Asn Val Asp Lys Val Leu Glu
225                 230                 235                 240

Arg Asp Gln Lys Leu Ser Glu Leu Asp Asp Arg Ala Asp Ala Leu Gln
                245                 250                 255

Ala Gly Ala Ser Gln Phe Glu Ser Ser Ala Ala Lys Leu Lys Arg Lys
            260                 265                 270

Tyr Trp Trp Lys Asn Cys Lys Met Met Ile Met Leu Gly Ala Ile Cys
                275                 280                 285

Ala Ile Ile Val Val Val Ile Val Ser Lys Tyr Arg Cys Pro Thr Phe
290                 295                 300

Leu Tyr Lys Val Val
305

<210> SEQ ID NO 33
<211> LENGTH: 308
<212> TYPE: PRT
<213> ORGANISM: Artificial Sequence
<220> FEATURE:
<223> OTHER INFORMATION: flag tag-gp130-VAMP2 fusion construct

<400> SEQUENCE: 33

Met Asp Tyr Lys Asp Asp Asp Lys Ile Ser Thr Val Val His Ser
1               5                   10                  15
```

Gly Tyr Arg His Gln Val Pro Ser Val Gln Val Phe Ser Arg Ser Glu
            20                  25                  30

Ser Thr Gln Pro Leu Leu Asp Ser Glu Glu Arg Pro Glu Asp Leu Gln
        35                  40                  45

Leu Val Asp His Val Asp Gly Asp Gly Ile Leu Pro Arg Gln Gln
50                  55                  60

Tyr Phe Lys Gln Asn Cys Ser Gln His Glu Ser Ser Pro Asp Ile Ser
65                  70                  75                  80

His Phe Glu Arg Ser Lys Gln Val Ser Val Asn Glu Glu Asp Phe
                85                  90                  95

Val Arg Leu Lys Gln Gln Ile Ser Asp His Ile Ser Gln Ser Cys Gly
                100                 105                 110

Ser Gly Gln Met Lys Met Phe Gln Glu Val Ser Ala Ala Asp Ala Phe
            115                 120                 125

Gly Pro Gly Thr Glu Gly Gln Val Glu Arg Phe Glu Thr Val Gly Met
130                 135                 140

Glu Ala Ala Thr Asp Glu Gly Met Pro Lys Ser Tyr Leu Pro Gln Thr
145                 150                 155                 160

Val Arg Gln Gly Gly Tyr Met Pro Gln Gly Gly Ser Glu Leu Ser Thr
                165                 170                 175

Ser Leu Tyr Lys Lys Val Gly Met Ser Ala Thr Ala Ala Thr Ala Pro
            180                 185                 190

Pro Ala Ala Pro Ala Gly Glu Gly Gly Pro Ala Pro Pro Asn
            195                 200                 205

Leu Thr Ser Asn Arg Arg Leu Gln Gln Thr Gln Ala Gln Val Asp Glu
            210                 215                 220

Val Val Asp Ile Met Arg Val Asn Val Asp Lys Val Leu Glu Arg Asp
225                 230                 235                 240

Gln Lys Leu Ser Glu Leu Asp Asp Arg Ala Asp Ala Leu Gln Ala Gly
                245                 250                 255

Ala Ser Gln Phe Glu Thr Ser Ala Ala Lys Leu Lys Arg Lys Tyr Trp
            260                 265                 270

Trp Lys Asn Leu Lys Met Met Ile Ile Leu Gly Val Ile Cys Ala Ile
            275                 280                 285

Ile Leu Ile Ile Ile Ile Val Tyr Phe Ser Thr Tyr Pro Thr Phe Leu
290                 295                 300

Tyr Lys Val Val
305

<210> SEQ ID NO 34
<211> LENGTH: 617
<212> TYPE: PRT
<213> ORGANISM: Artificial Sequence
<220> FEATURE:
<223> OTHER INFORMATION: flag-tag-ERN1cyt-gp130 fusion construct

<400> SEQUENCE: 34

Met Asp Tyr Lys Asp Asp Asp Asp Lys Ile Ser Glu Phe Phe Cys Pro
1               5                   10                  15

Lys Asp Val Leu Gly His Gly Ala Glu Gly Thr Ile Val Tyr Arg Gly
            20                  25                  30

Met Phe Asp Asn Arg Asp Val Ala Val Lys Arg Ile Leu Pro Glu Cys
        35                  40                  45

Phe Ser Phe Ala Asp Arg Glu Val Gln Leu Leu Arg Glu Ser Asp Glu
50                  55                  60

```
His Pro Asn Val Ile Arg Tyr Phe Cys Thr Glu Lys Asp Arg Gln Phe
 65                  70                  75                  80

Gln Tyr Ile Ala Ile Glu Leu Cys Ala Ala Thr Leu Gln Glu Tyr Val
                 85                  90                  95

Glu Gln Lys Asp Phe Ala His Leu Gly Leu Glu Pro Ile Thr Leu Leu
            100                 105                 110

Gln Gln Thr Thr Ser Gly Leu Ala His Leu His Ser Leu Asn Ile Val
            115                 120                 125

His Arg Asp Leu Lys Pro His Asn Ile Leu Ile Ser Met Pro Asn Ala
        130                 135                 140

His Gly Lys Ile Lys Ala Met Ile Ser Asp Phe Gly Leu Cys Lys Lys
145                 150                 155                 160

Leu Ala Val Gly Arg His Ser Phe Ser Arg Arg Ser Gly Val Pro Gly
                165                 170                 175

Thr Glu Gly Trp Ile Ala Pro Glu Met Leu Ser Glu Asp Cys Lys Glu
            180                 185                 190

Asn Pro Thr Tyr Thr Val Asp Ile Phe Ser Ala Gly Cys Val Phe Tyr
        195                 200                 205

Tyr Val Ile Ser Glu Gly Ser His Pro Phe Gly Lys Ser Leu Gln Arg
210                 215                 220

Gln Ala Asn Ile Leu Leu Gly Ala Cys Ser Leu Asp Cys Leu His Pro
225                 230                 235                 240

Glu Lys His Glu Asp Val Ile Ala Arg Glu Leu Ile Glu Lys Met Ile
            245                 250                 255

Ala Met Asp Pro Gln Lys Arg Pro Ser Ala Lys His Val Leu Lys His
        260                 265                 270

Pro Phe Phe Trp Ser Leu Glu Lys Gln Leu Gln Phe Phe Gln Asp Val
        275                 280                 285

Ser Asp Arg Ile Glu Lys Glu Ser Leu Asp Gly Pro Ile Val Lys Gln
290                 295                 300

Leu Glu Arg Gly Gly Arg Ala Val Val Lys Met Asp Trp Arg Glu Asn
305                 310                 315                 320

Ile Thr Val Pro Leu Gln Thr Asp Leu Arg Lys Phe Arg Thr Tyr Lys
                325                 330                 335

Gly Gly Ser Val Arg Asp Leu Leu Arg Ala Met Arg Asn Lys Lys His
            340                 345                 350

His Tyr Arg Glu Leu Pro Ala Glu Val Arg Glu Thr Leu Gly Ser Leu
        355                 360                 365

Pro Asp Asp Phe Val Cys Tyr Phe Thr Ser Arg Phe Pro His Leu Leu
        370                 375                 380

Ala His Thr Tyr Arg Ala Met Glu Leu Cys Ser His Glu Arg Leu Phe
385                 390                 395                 400

Gln Pro Tyr Tyr Phe His Glu Pro Pro Glu Pro Gln Pro Pro Val Thr
                405                 410                 415

Pro Asp Ala Leu Pro Ser Arg Gly Ser Gly Ser Gly Gly Ser Gly Ser Thr
            420                 425                 430

Val Val His Ser Gly Tyr Arg His Gln Val Pro Ser Val Gln Val Phe
            435                 440                 445

Ser Arg Ser Glu Ser Thr Gln Pro Leu Leu Asp Ser Glu Glu Arg Pro
        450                 455                 460

Glu Asp Leu Gln Leu Val Asp His Val Asp Gly Gly Asp Gly Ile Leu
465                 470                 475                 480
```

```
Pro Arg Gln Gln Tyr Phe Lys Gln Asn Cys Ser Gln His Glu Ser Ser
                485                 490                 495

Pro Asp Ile Ser His Phe Glu Arg Ser Lys Gln Val Ser Val Asn
            500                 505                 510

Glu Glu Asp Phe Val Arg Leu Lys Gln Gln Ile Ser Asp His Ile Ser
                515                 520                 525

Gln Ser Cys Gly Ser Gly Gln Met Lys Met Phe Gln Glu Val Ser Ala
            530                 535                 540

Ala Asp Ala Phe Gly Pro Gly Thr Glu Gly Gln Val Glu Arg Phe Glu
545                 550                 555                 560

Thr Val Gly Met Glu Ala Ala Thr Asp Glu Gly Met Pro Lys Ser Tyr
                565                 570                 575

Leu Pro Gln Thr Val Arg Gln Gly Gly Tyr Met Pro Gln Gly Gly Ser
            580                 585                 590

Glu Leu Ser Thr Ser Leu Tyr Lys Lys Ala Gly Tyr Leu Pro Gln Thr
                595                 600                 605

Val Arg Gln Gly Gly Tyr Met Pro Gln
        610                 615

<210> SEQ ID NO 35
<211> LENGTH: 645
<212> TYPE: PRT
<213> ORGANISM: Artificial Sequence
<220> FEATURE:
<223> OTHER INFORMATION: flag tag-gp130-RTp51 fusion construct

<400> SEQUENCE: 35

Met Asp Tyr Lys Asp Asp Asp Asp Lys Ile Ser Thr Val Val His Ser
1               5                   10                  15

Gly Tyr Arg His Gln Val Pro Ser Val Gln Val Phe Ser Arg Ser Glu
                20                  25                  30

Ser Thr Gln Pro Leu Leu Asp Ser Glu Glu Arg Pro Glu Asp Leu Gln
            35                  40                  45

Leu Val Asp His Val Asp Gly Asp Gly Ile Leu Pro Arg Gln Gln
        50                  55                  60

Tyr Phe Lys Gln Asn Cys Ser Gln His Glu Ser Ser Pro Asp Ile Ser
65                  70                  75                  80

His Phe Glu Arg Ser Lys Gln Val Ser Val Asn Glu Glu Asp Phe
                85                  90                  95

Val Arg Leu Lys Gln Gln Ile Ser Asp His Ile Ser Gln Ser Cys Gly
            100                 105                 110

Ser Gly Gln Met Lys Met Phe Gln Glu Val Ser Ala Ala Asp Ala Phe
        115                 120                 125

Gly Pro Gly Thr Glu Gly Gln Val Glu Arg Phe Glu Thr Val Gly Met
    130                 135                 140

Glu Ala Ala Thr Asp Glu Gly Met Pro Lys Ser Tyr Leu Pro Gln Thr
145                 150                 155                 160

Val Arg Gln Gly Gly Tyr Met Pro Gln Gly Gly Ser Glu Leu Ser Thr
                165                 170                 175

Ser Leu Tyr Lys Lys Ala Gly Tyr Leu Pro Gln Thr Val Arg Gln Gly
            180                 185                 190

Gly Tyr Met Pro Gln Gly Gly Ser Glu Phe Gly Ser Ser Pro Ile Ser
        195                 200                 205

Pro Ile Glu Thr Val Pro Val Lys Leu Lys Pro Gly Met Asp Gly Pro
    210                 215                 220
```

-continued

Lys Val Lys Gln Trp Pro Leu Thr Glu Glu Lys Ile Lys Ala Leu Val
225                 230                 235                 240

Glu Ile Cys Thr Glu Met Glu Lys Glu Gly Lys Ile Ser Lys Ile Gly
            245                 250                 255

Pro Glu Asn Pro Tyr Asn Thr Pro Val Phe Ala Ile Lys Lys Lys Asp
        260                 265                 270

Ser Thr Lys Trp Arg Lys Leu Val Asp Phe Arg Glu Leu Asn Lys Arg
    275                 280                 285

Thr Gln Asp Phe Trp Glu Val Gln Leu Gly Ile Pro His Pro Ala Gly
    290                 295                 300

Leu Lys Gln Lys Lys Ser Val Thr Val Leu Asp Val Gly Asp Ala Tyr
305                 310                 315                 320

Phe Ser Val Pro Leu Asp Lys Asp Phe Arg Lys Tyr Thr Ala Phe Thr
            325                 330                 335

Ile Pro Ser Ile Asn Asn Glu Thr Pro Gly Ile Arg Tyr Gln Tyr Asn
            340                 345                 350

Val Leu Pro Gln Gly Trp Lys Gly Ser Pro Ala Ile Phe Gln Cys Ser
            355                 360                 365

Met Thr Lys Ile Leu Glu Pro Phe Arg Lys Gln Asn Pro Asp Ile Val
    370                 375                 380

Ile Tyr Gln Tyr Met Asp Asp Leu Tyr Val Gly Ser Asp Leu Glu Ile
385                 390                 395                 400

Gly Gln His Arg Thr Lys Ile Glu Glu Leu Arg Gln His Leu Leu Arg
            405                 410                 415

Trp Gly Phe Thr Thr Pro Asp Lys Lys His Gln Lys Glu Pro Pro Phe
            420                 425                 430

Leu Trp Met Gly Tyr Glu Leu His Pro Asp Lys Trp Thr Val Gln Pro
            435                 440                 445

Ile Val Leu Pro Glu Lys Asp Ser Trp Thr Val Asn Asp Ile Gln Lys
            450                 455                 460

Leu Val Gly Lys Leu Asn Trp Ala Ser Gln Ile Tyr Ala Gly Ile Lys
465                 470                 475                 480

Val Arg Gln Leu Cys Lys Leu Leu Arg Gly Thr Lys Ala Leu Thr Glu
            485                 490                 495

Val Val Pro Leu Thr Glu Glu Ala Glu Leu Glu Leu Ala Glu Asn Arg
            500                 505                 510

Glu Ile Leu Lys Glu Pro Val His Gly Val Tyr Tyr Asp Pro Ser Lys
            515                 520                 525

Asp Leu Ile Ala Glu Ile Gln Lys Gln Gly Gln Gly Gln Trp Thr Tyr
    530                 535                 540

Gln Ile Tyr Gln Glu Pro Phe Lys Asn Leu Lys Thr Gly Lys Tyr Ala
545                 550                 555                 560

Arg Met Lys Gly Ala His Thr Asn Asp Val Lys Gln Leu Thr Glu Ala
            565                 570                 575

Val Gln Lys Ile Ala Thr Glu Ser Ile Val Ile Trp Gly Lys Thr Pro
            580                 585                 590

Lys Phe Lys Leu Pro Ile Gln Lys Glu Thr Trp Glu Ala Trp Trp Thr
            595                 600                 605

Glu Tyr Trp Gln Ala Thr Trp Ile Pro Glu Trp Glu Phe Val Asn Thr
            610                 615                 620

Pro Pro Leu Val Lys Leu Trp Tyr Gln Leu Glu Lys Glu Pro Ile Ile
625                 630                 635                 640

Gly Ala Glu Thr Phe

<210> SEQ ID NO 36
<211> LENGTH: 174
<212> TYPE: PRT
<213> ORGANISM: Artificial Sequence
<220> FEATURE:
<223> OTHER INFORMATION: polypeptide encoded by pMG1 plasmid

<400> SEQUENCE: 36

Met Asp Tyr Lys Asp Asp Asp Lys Ile Ser Thr Val Val His Ser
1               5                   10                  15

Gly Tyr Arg His Gln Val Pro Ser Val Gln Val Phe Ser Arg Ser Glu
                20                  25                  30

Ser Thr Gln Pro Leu Leu Asp Ser Glu Glu Arg Pro Glu Asp Leu Gln
            35                  40                  45

Leu Val Asp His Val Asp Gly Gly Asp Gly Ile Leu Pro Arg Gln Gln
        50                  55                  60

Tyr Phe Lys Gln Asn Cys Ser Gln His Glu Ser Ser Pro Asp Ile Ser
65                  70                  75                  80

His Phe Glu Arg Ser Lys Gln Val Ser Ser Val Asn Glu Glu Asp Phe
                85                  90                  95

Val Arg Leu Lys Gln Gln Ile Ser Asp His Ile Ser Gln Ser Cys Gly
            100                 105                 110

Ser Gly Gln Met Lys Met Phe Gln Glu Val Ser Ala Ala Asp Ala Phe
        115                 120                 125

Gly Pro Gly Thr Glu Gly Gln Val Glu Arg Phe Glu Thr Val Gly Met
    130                 135                 140

Glu Ala Ala Thr Asp Glu Gly Met Pro Lys Ser Tyr Leu Pro Gln Thr
145                 150                 155                 160

Val Arg Gln Gly Gly Tyr Met Pro Gln Gly Gly Ser Glu Phe
                165                 170

<210> SEQ ID NO 37
<211> LENGTH: 202
<212> TYPE: PRT
<213> ORGANISM: Artificial Sequence
<220> FEATURE:
<223> OTHER INFORMATION: polypeptide encoded by pMG2 plasmid

<400> SEQUENCE: 37

Met Asp Tyr Lys Asp Asp Asp Lys Ile Ser Thr Val Val His Ser
1               5                   10                  15

Gly Tyr Arg His Gln Val Pro Ser Val Gln Val Phe Ser Arg Ser Glu
                20                  25                  30

Ser Thr Gln Pro Leu Leu Asp Ser Glu Glu Arg Pro Glu Asp Leu Gln
            35                  40                  45

Leu Val Asp His Val Asp Gly Gly Asp Gly Ile Leu Pro Arg Gln Gln
        50                  55                  60

Tyr Phe Lys Gln Asn Cys Ser Gln His Glu Ser Ser Pro Asp Ile Ser
65                  70                  75                  80

His Phe Glu Arg Ser Lys Gln Val Ser Ser Val Asn Glu Glu Asp Phe
                85                  90                  95

Val Arg Leu Lys Gln Gln Ile Ser Asp His Ile Ser Gln Ser Cys Gly
            100                 105                 110

Ser Gly Gln Met Lys Met Phe Gln Glu Val Ser Ala Ala Asp Ala Phe
        115                 120                 125

-continued

```
Gly Pro Gly Thr Glu Gly Gln Val Glu Arg Phe Glu Thr Val Gly Met
    130                 135                 140
Glu Ala Ala Thr Asp Glu Gly Met Pro Lys Ser Tyr Leu Pro Gln Thr
145             150                 155                 160
Val Arg Gln Gly Gly Tyr Met Pro Gln Gly Gly Ser Glu Leu Ser Thr
                165                 170                 175
Ser Leu Tyr Lys Lys Ala Gly Tyr Leu Pro Gln Thr Val Arg Gln Gly
            180                 185                 190
Gly Tyr Met Pro Gln Gly Gly Ser Glu Phe
            195                 200
```